(12) United States Patent
Heywood et al.

(10) Patent No.: US 10,383,900 B2
(45) Date of Patent: Aug. 20, 2019

(54) SYSTEMS AND METHODS FOR STORAGE AND DELIVERY OF AMMONIA OXIDIZING BACTERIA

(71) Applicant: AOBIOME LLC, Cambridge, MA (US)

(72) Inventors: James Heywood, Newton, MA (US); Spiros Jamas, Cambridge, MA (US); David R. Whitlock, Cambridge, MA (US); Larry Weiss, San Francisco, CA (US)

(73) Assignee: AOBIOME LLC, Cambridge, MA (US)

( * ) Notice: Subject to any disclaimer, the term of this patent is extended or adjusted under 35 U.S.C. 154(b) by 0 days.

(21) Appl. No.: 15/313,178

(22) PCT Filed: May 21, 2015

(86) PCT No.: PCT/US2015/032007
§ 371 (c)(1),
(2) Date: Nov. 22, 2016

(87) PCT Pub. No.: WO2015/179664
PCT Pub. Date: Nov. 26, 2015

(65) Prior Publication Data
US 2017/0189454 A1 Jul. 6, 2017

Related U.S. Application Data

(60) Provisional application No. 62/002,056, filed on May 22, 2014.

(51) Int. Cl.
*A61K 35/74* (2015.01)
*C12M 1/34* (2006.01)
(Continued)

(52) U.S. Cl.
CPC ............... *A61K 35/74* (2013.01); *A61J 1/20* (2013.01); *A61J 1/202* (2015.05); *A61J 1/2003* (2015.05);
(Continued)

(58) Field of Classification Search
None
See application file for complete search history.

(56) References Cited

U.S. PATENT DOCUMENTS 5,700,486 A * 12/1997 Canal .................. A61K 9/1617
264/4.1
5,725,499 A * 3/1998 Silverstein ............. A61M 5/19
222/145.1
2004/0014188 A1* 1/2004 Whitlock ............. A61K 8/0208
435/170

FOREIGN PATENT DOCUMENTS

WO 0213982 A1 2/2002
WO 03057380 A2 7/2003
WO 2005030147 A2 4/2005

OTHER PUBLICATIONS

Ioannis Gryllos et al., "Ammonia-oxidizing bacteria accelerate wound closure in diabetic mice", Nitric Oxide, vol. 42, p. 111-112, Nov. 1, 2014, XP055201871, ISSN 1089-8603, DOI 10.1016/j.niox.2014.09.041.
(Continued)

*Primary Examiner* — David W Berke-Schlessel
(74) *Attorney, Agent, or Firm* — Lando & Anastasi, LLP

(57) ABSTRACT

This disclosure provides, inter alia, systems and methods for storage and delivery of ammonia oxidizing bacteria, and preparations comprising ammonia oxidizing bacteria. The ammonia oxidizing bacteria may be provided in a container or a kit, with one or more other components that may enhance delivery. The systems and methods herein may be used, for instance, to treat diseases associated with low
(Continued)

nitrite levels, skin diseases, and diseases caused by pathogenic bacteria.

18 Claims, 27 Drawing Sheets

(51) Int. Cl.
    *B65D 81/32*     (2006.01)
    *A61K 8/64*     (2006.01)
    *C12Q 1/12*     (2006.01)
    *A61J 1/20*     (2006.01)
    *A61K 8/99*     (2017.01)
    *A61K 35/741*     (2015.01)

(52) U.S. Cl.
    CPC ............. *A61J 1/2089* (2013.01); *A61K 8/645* (2013.01); *A61K 8/99* (2013.01); *A61K 35/741* (2013.01); *B65D 81/32* (2013.01); *C12M 41/00* (2013.01); *C12Q 1/12* (2013.01)

(56) References Cited

OTHER PUBLICATIONS

Ioannis Gryllos et al., "Ammonia-oxidizing bacteria for the generation and delivery of acidified nitrite and nitric oxide in vivo", Nitric Oxide, vol. 42, p. 124, Nov. 1, 2014, XP055201872, ISSN 1089-8603, DOI 10.1016/j.niox.2014.09.076.

* cited by examiner

Incubation of 1x *N. eutropha* D23 with various concentrations of ColaTerric COAB

**Incubation of different densities of *N. eutropha* D23 with increasing concentrations of surfactant ColaTeric COAB**

Incubation of 1x *N. eutropha* D23 with various concentrations of ColaTerric COAB Incubation of 1x *N. eutropha* D23 with various concentrations of
Dr. Bronners Castille soap

**Recovery of 0.1x *N. eutropha* D23 after incubation with various concentrations of Dr. Bronners Castille soap**

Incubation of 1x *N. eutropha* D23 with various concentrations of Plantaren 2000 N UP

**Incubation of 1x *N. eutropha* D23 with various concentrations of Plantaren 2000 N UP**

Incubation of different densities of *N. eutropha* D23
with increasing concentrations of SDS

**Response of *N. eutropha* D23 cells to various concentrations of Sodium dodecyl sulfate (SDS), an anionic surfactant**

**Incubation of 1x *N. eutropha* D23 with various concentrations of PolySufanate 160P**

**Recovery of 0.1x *N. eutropha* D23 after incubation with various concentrations of PolySufanate 160P**

**Incubation of 1x *N. eutropha* D23 with various concentrations of Stepanol WA – Extra K**

Incubation of different densities of *N. eutropha* D23 with increasing concentrations of surfactant Stepanol WA

**Recovery of 0.1x *N. eutropha* D23 after incubation with various concentrations of Stepanol WA – Extra K**

**Incubation of 1x *N. eutropha* D23 with various concentrations of Plantapon 611 L UP**

Incubation of different densities of *N. eutropha* D23 with increasing concentrations of surfactant Plantapon 611L

**Recovery of 0.1x *N. eutropha* D23 after incubation with various concentrations of Plantapon 611 L UP**

**Incubation of different densities of *N. eutropha* D23 with increasing concentrations of surfactant Tween 80**

Incubation of different densities of *N. eutropha* D23
with increasing concentrations of surfactant Colalux LO

Incubation of different densities of *N. eutropha* D23 with increasing concentrations of surfactant Plantaren 200

Incubation of different densities of *N. eutropha* D23 with increasing concentrations of surfactant RhodaSurf 6

SYSTEMS AND METHODS FOR STORAGE AND DELIVERY OF AMMONIA OXIDIZING BACTERIA

CROSS-REFERENCE TO RELATED APPLICATIONS

This application is a U.S. national phase application under 35 U.S.C. § 371 of International (PCT) Patent Application Serial No. PCT/US2015/032007, filed May 21, 2015 which, in turn, claims priority to U.S. Provisional Application No. 62/002,056, filed May 22, 2014, the contents of which are incorporated herein by reference in their entirety.

BACKGROUND

Beneficial bacteria can be used to suppress the growth of pathogenic bacteria. Bacteria and other microorganisms are ubiquitous in the environment. The discovery of pathogenic bacteria and the germ theory of disease have had a tremendous effect on health and disease states. Bacteria are a normal part of the environment of all living things. In the gut, these bacteria are not pathogenic under normal conditions, and in fact improve health by rendering the normal intestinal contents less hospitable for disease causing organisms. Disease prevention is accomplished in a number of ways: nutrients are consumed, leaving less for pathogens; conditions are produced, such as pH and oxygen tension, which are not hospitable for pathogens; compounds are produced that are toxic to pathogens; pathogens are consumed as food by these microorganisms; less physical space remains available for pathogens; and specific binding sites are occupied leaving fewer binding sites available for pathogens. The presence of these desirable bacteria is seen as useful in preventing disease states.

There is a need in the art for improved beneficial bacteria that can suppress the growth of pathogenic bacteria.

SUMMARY

This disclosure provides, inter alia, a container. The container may comprise a first chamber in which is disposed a preparation of an ammonia oxidizing bacteria. The container may comprise a second chamber in which is disposed an activator, wherein the first chamber and the second chamber are separated by a bather provided to prevent fluid communication between the first chamber and the second chamber.

In some embodiments, the activator comprises a buffer solution. In some embodiments the activator may comprise at least one of ammonia, ammonium ions, and urea. The container may be configured such that upon actuation of the container, the preparation of ammonia oxidizing bacteria and the activator are mixed. The container may comprise a delivery system. The delivery system may comprise a pump.

In some embodiments, the first chamber and the second chamber may be disposed within the other. In certain aspects, the second chamber may be disposed within a compartment, and the compartment is disposed within the first chamber. In certain other aspects, the first chamber may be disposed within a compartment, and the compartment is disposed within the second chamber.

In some embodiments, the second chamber may comprise a controlled release material, e.g., slow release material, and the activator comprising at least one of ammonia, ammonium ions, and urea, to provide a controlled release, e.g., slow release, of the at least one of ammonia, ammonium ions, and urea to the preparation of ammonia oxidizing bacteria upon delivery.

In some embodiments, the container comprises a single-use container. In other embodiments, the container comprises a multiple-use container. In yet other embodiments, the container comprises a two-compartment syringe. In yet other embodiments, the container comprises a two-compartment bottle. In yet other embodiments, the container comprises a two-compartment ampule. In yet other embodiments, the container comprises a deodorant applicator.

In some embodiments, the container further comprises a mixing chamber. In some embodiments, upon actuation the ammonia oxidizing bacteria and the activator mix or contact one another in the mixing chamber.

In some embodiments, the first chamber, or the preparation of ammonia oxidizing bacteria, further comprises an excipient, e.g., one of a pharmaceutically acceptable excipient or a cosmetically acceptable excipient. The excipient, e.g., one of the pharmaceutically acceptable excipient and the cosmetically acceptable excipient, may be suitable for one of topical, nasal, pulmonary, and gastrointestinal administration. The excipient, e.g., one of the pharmaceutically acceptable excipient and the cosmetically acceptable excipient may be a surfactant.

In some embodiments, the surfactant may be selected from the group consisting of cocamidopropyl betaine (Cola-Teric COAB), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g., Rhoda-Pex ESB 70 NAT), alkyl polyglucoside (e.g., Plantaren 2000 N UP), sodium laureth sulfate (Plantaren 200), Dr. Bronner's Castile soap, Lauramine oxide (ColaLux Lo), sodium dodecyl sulfate (SDS), polysulfonate alkyl polyglucoside (PolySufanate 160 P), sodium lauryl sulfate (Stepanol-WA Extra K), and combinations thereof.

In some embodiments, the container may be substantially free of other organisms. The container may be disposed in a powder, cosmetic, cream, stick, aerosol, salve, wipe, or bandage. The container may be provided as a powder, cosmetic, cream, stick, aerosol, salve, wipe, or bandage. In some embodiments, the preparation of ammonia oxidizing bacteria may comprise a moisturizing agent, deodorizing agent, scent, colorant, insect repellant, cleansing agent, or UV-blocking agent. In some embodiments, the container may further comprise a moisturizing agent, deodorizing agent, scent, colorant, insect repellant, cleansing agent, or UV-blocking agent. In some embodiments, a container is provided in which at least one of the moisturizing agent, deodorizing agent, scent, colorant, insect repellant, cleansing agent, or UV-blocking agent is disposed in one or more of the first chamber, the second chamber and a third chamber.

In some embodiments the excipient, e.g., the pharmaceutically acceptable excipient or the cosmetically acceptable excipient, comprises an anti-adherent, binder, coat, disintegrant, filler, flavor, color, lubricant, glidant, sorbent, preservative, or sweetener.

In some embodiments, the preparation of ammonia oxidizing bacteria comprises about $10^9$ to about $10^{13}$ CFU/L. In some embodiments, the preparation of ammonia oxidizing bacteria comprises about $10^{10}$ to about $10^{13}$ CFU/L. In some embodiments, the preparation of ammonia oxidizing bacteria comprises between about 0.1 milligrams (mg) and about 1000 mg of ammonia oxidizing bacteria. The mass ratio of ammonia oxidizing bacteria to the pharmaceutically acceptable excipient or the cosmetically acceptable excipient may be in a range of about 0.1 grams per liter to about 1 gram per liter.

In some embodiments, the contents of the container may be useful for treating or preventing a skin disorder, a treatment or prevention of a disease or condition associated with low nitrite levels, a treatment or prevention of body odor, a treatment to supply nitric oxide to a subject, or a treatment to inhibit microbial growth.

In some embodiments, at least one of the first chamber and the second chamber comprises at least one mixing indicator component to indicate mixing of the preparation of ammonia oxidizing bacteria and the activator. In some embodiments, the container, e.g., at least one of the first chamber and the second chamber, comprises at least one activation indicator component to indicate activation of the preparation of ammonia oxidizing bacteria and the activator. At least one mixing indicator component or the at least one activation indicator may comprise a color marker. The first color marker may be positioned in the first chamber and a second color marker may be positioned in the second chamber, wherein, upon mixing, a third color is generated.

In some embodiments, the container may be configured to deliver the preparation of ammonia oxidizing bacteria from the first chamber to a surface prior to the activator of the second chamber. In some embodiments, the container may be configured to deliver the activator of the second chamber to a surface prior to the preparation of ammonia oxidizing bacteria from the first chamber. In some embodiments, the container may be configured to deliver the preparation of ammonia oxidizing bacteria from the first chamber and the activator of the second chamber substantially simultaneously.

In some embodiments the container may comprise a third chamber configured to provide a diluting solution to at least one of the first chamber and the second chamber. In some embodiments, the container is constructed to be at least partially resistant to at least one of gaseous exchange, water, and light.

In some embodiments the ammonia oxidizing bacteria is selected from the group consisting of *Nitrosomonas, Nitrosococcus, Nitrosospira, Nitrosocystis, Nitrosolobus, Nitrosovibrio*, and combinations thereof. In some embodiments a container is provided wherein one of the first chamber and the second chamber further comprises an organism selected from the group consisting of *Lactobacillus, Streptococcus, Bifidobacter*, and combinations thereof. In some embodiments, the preparation of ammonia oxidizing bacteria comprises ammonia oxidizing bacteria in a growth state. In some embodiments, the preparation of ammonia oxidizing bacteria comprises ammonia oxidizing bacteria in a storage state. In some embodiments, the preparation of ammonia oxidizing bacteria comprises ammonia oxidizing bacteria in a polyphosphate loading state.

In some embodiments, upon actuation, at least one of ammonia oxidizing bacteria in a storage state and a polyphosphate loading state are mixed with the activator, e.g., to provide activated ammonia oxidizing bacteria, e.g., ammonia oxidizing bacteria in a growth state.

In some embodiments, the container may be adapted to deliver a cosmetic product. In some embodiments, the container may be adapted to deliver a therapeutic product.

In some embodiments, contents of the container may be useful for treatment of at least one of HIV dermatitis, infection in an ulcer, e.g., venous ulcer, e.g., leg ulcer, e.g., venous leg ulcer, e.g. infection in a diabetic foot ulcer, atopic dermatitis, acne, e.g., acne vulgaris, eczema, contact dermatitis, allergic reaction, psoriasis, uticaria, rosacea, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, pneumonia, primary immunodeficiency, epidermal lysis bulosa or cancer. In embodiments, the condition is a venous leg ulcer.

In some embodiments a container is provided wherein a weight of the container is less than about 50, 100, 200, 300, 400, 500, 600, 700, 800, 900, 1000, 1500, or 2000 grams.

In some embodiments, the first chamber and the second chamber are configured such that the barrier is not fixed relative to the first chamber and the second chamber. In some embodiments, the first chamber and the second chamber are configured such that the barrier is at least partially common to the first chamber and the second chamber. In some embodiments, the first chamber comprises a first housing and a first lumen, and the second chamber comprises a second housing and a second lumen. In some embodiments, the first housing and the second housing are fixed relative to each other. In some embodiments, a portion of the first housing and the second housing is shared by the first chamber and the second chamber. In some embodiments, the portion comprises a bather. In some embodiments, the first housing and the second housing move independently from one another.

This disclosure provides, inter alia, a kit. The kit may comprise a preparation of an ammonia oxidizing bacteria, and an activator for activating the ammonia oxidizing bacteria. The kit may comprise a delivery device for delivering at least one of the preparation of ammonia oxidizing bacteria and the activator to a subject. The kit may comprise a container as described herein. The delivery device may be the container as described herein.

The delivery device may comprise a first chamber and a second chamber, wherein the first chamber and the second chamber are separated by a barrier provided to prevent fluid communication between the first chamber and the second chamber. The preparation of the ammonia oxidizing bacteria may be disposed in the first chamber, and the activator may be disposed in the second chamber. The activator may comprise at least one of ammonia, ammonium ions, and urea.

In some embodiments, the kit may comprise a wash solution or wipe provided to clean the surface to which the preparation of ammonia oxidizing bacteria is applied. The kit may further comprise a diluting solution to allow dilution of at least one of the preparation of ammonia oxidizing bacteria and the activator.

In some embodiments, the kit may comprise an assay to determine a viability of the preparation of ammonia oxidizing bacteria. In some embodiments, the kit may further comprise an assay to determine a characteristic of the surface to which the preparation of ammonia oxidizing bacteria is applied.

In some embodiments the activator may comprise a buffer solution. In some embodiments, the activator may comprise a media.

In some embodiments, the delivery device may be configured such that upon actuation, the preparation of ammonia oxidizing bacteria and the activator are mixed. The delivery device may comprise a pump.

In some embodiments, one of the first chamber and the second chamber is disposed within each other. In some embodiments, the second chamber is disposed within a compartment, and the compartment is disposed within the first chamber. In some embodiments, the first chamber is disposed within a compartment and the compartment is disposed within the second chamber. In some embodiments, the second chamber comprises a controlled release material, e.g., slow release material, and the activator comprising at least one of ammonia, ammonium ions, and urea, to provide a controlled release, e.g., slow release, of the at least one of ammonia, ammonium ions, and urea to the preparation of ammonia oxidizing bacteria upon delivery.

In some embodiments, the delivery device may comprise a single-use delivery device. In some embodiments, the delivery device may comprise a multiple-use delivery device. In some embodiments, the delivery device may comprise a two-compartment syringe. In some embodiments, the delivery device may comprise a two-compartment bottle. In some embodiments, the delivery device may comprise a two-compartment ampule. In some embodiments, the delivery device may comprise a deodorant applicator.

In some embodiments, the delivery device may comprise a mixing chamber. In some embodiments, upon actuation the ammonia oxidizing bacteria and the activator may mix or contact one another in the mixing chamber. In some embodiments, the first chamber, or the preparation of ammonia oxidizing bacteria, may further comprise an excipient, e.g., one of a pharmaceutically acceptable excipient and a cosmetically acceptable excipient. In some embodiments, the excipient, e.g., one of the pharmaceutically acceptable excipient or the cosmetically acceptable excipient may be suitable for one of topical, nasal, and pulmonary administration.

In some embodiments, the excipient, e.g., one of the pharmaceutically acceptable excipient and the cosmetically acceptable excipient, is a surfactant. In some embodiments, the surfactant may be selected from the group consisting of cocamidopropyl betaine (ColaTeric COAB), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g., RhodaPex ESB 70 NAT), alkyl polyglucoside (e.g., Plantaren 2000 N UP), sodium laureth sulfate (Plantaren 200), Dr. Bronner's Castile soap, Lauramine oxide (ColaLux Lo), sodium dodecyl sulfate (SDS), polysulfonate alkyl polyglucoside (PolySufanate 160 P), sodium lauryl sulfate (Stepanol-WA Extra K). and combinations thereof.

In some embodiments, at least one of the preparation of ammonia oxidizing bacteria and the activator may be substantially free of other organisms. In some embodiments the preparation of ammonia oxidizing bacteria may be disposed in a powder, cosmetic, cream, stick, aerosol, salve, wipe, or bandage. In some embodiments, the preparation of ammonia oxidizing bacteria may be provided as a powder, cosmetic, cream, stick, aerosol, salve, wipe, or bandage. In some embodiments, the kit may further comprise a moisturizing agent, deodorizing agent, scent, colorant, insect repellant, cleansing agent, or UV-blocking agent. At least one of the moisturizing agent, deodorizing agent, scent, colorant, insect repellant, cleansing agent, and UV-blocking agent may be disposed in one or more of the first chamber, the second chamber, and a third chamber.

In some embodiments, the excipient, e.g., the pharmaceutically acceptable excipient or the cosmetically acceptable excipient may comprise an anti-adherent, binder, coat, disintegrant, filler, flavor, color, lubricant, glidant, sorbent, preservative, or sweetener.

In some embodiments, the kit is provided with a preparation of ammonia oxidizing bacteria that may comprise about $10^{10}$ to about $10^{13}$ CFU/L. In some embodiments, the preparation of ammonia oxidizing bacteria may comprise between about 0.1 milligrams (mg) and about 1000 mg of ammonia oxidizing bacteria. In some embodiments, the mass ratio of ammonia oxidizing bacteria to the excipient, e.g., the pharmaceutically acceptable excipient or the cosmetically acceptable excipient is in a range of about 0.1 grams per liter to about 1 gram per liter.

In some embodiments, the contents of the kit are useful for treating or preventing a skin disorder, a treatment or prevention of a disease or condition associated with low nitrite levels, a treatment or prevention of body odor, a treatment to supply nitric oxide to a subject, or a treatment to inhibit microbial growth. In some embodiments the kit may further comprise at least one mixing indicator component to indicate mixing of the preparation of ammonia oxidizing bacteria and the activator. In some embodiments, at least one of the first chamber and the second chamber may comprise at least one activation indicator component to indicate activation of the preparation of ammonia oxidizing bacteria and the activator. In some embodiments, the kit may comprise at least one activation indicator component to indicate activation of the preparation of ammonia oxidizing bacteria and the activator. In some embodiments, at least one mixing indicator component or the at least one activation indicator component may comprise a color marker. In some embodiments, a first color marker is positioned in the first chamber and a second color marker is positioned in the second chamber, wherein, upon mixing, a third color is generated.

In some embodiments, the delivery device may be configured to deliver the preparation of ammonia oxidizing bacteria to a surface prior to the activator. In some embodiments, the delivery device may be configured to deliver the activator to a surface prior to the preparation of ammonia oxidizing bacteria. The delivery device may be configured to deliver the preparation of ammonia oxidizing bacteria and the activator substantially simultaneously.

In some embodiments, the delivery device may comprise a third chamber. In some embodiments, the third chamber comprises a diluting solution.

In some embodiments, the delivery device is constructed to be at least partially resistant to at least one of gaseous exchange, water, and light.

In some embodiments, the ammonia oxidizing bacteria of the kit is selected from the group consisting of *Nitrosomonas, Nitrosococcus, Nitrosospira, Nitrosocystis, Nitrosolobus, Nitrosovibrio*, and combinations thereof. In some embodiments, the kit may further comprise an organism selected from the group consisting of *Lactobacillus, Streptococcus, Bifidobacter*, and combinations thereof.

In some embodiments, the preparation of ammonia oxidizing bacteria comprises ammonia oxidizing bacteria in a growth state. In some embodiments, the preparation of ammonia oxidizing bacteria comprises ammonia oxidizing bacteria in a storage state. In some embodiments, the preparation of ammonia oxidizing bacteria comprises ammonia oxidizing bacteria in a polyphosphate loading state.

In some embodiments, the kit may be adapted to deliver a cosmetic product. In some embodiments, the kit may be adapted to deliver a therapeutic product.

In some embodiments, the contents of the kit may be useful for the treatment of at least one of HIV, dermatitis, infection in an ulcer, e.g., venous ulcer, e.g., leg ulcer, e.g., venous leg ulcer, e.g. infection in a diabetic foot ulcer, atopic dermatitis, acne, e.g., acne vulgaris, eczema, contact dermatitis, allergic reaction, psoriasis, uticaria, rosacea, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, pneumonia, primary immunodeficiency, epidermal lysis bulosa or cancer. In embodiments, the condition is a venous leg ulcer.

In some embodiments, the kit may further comprise instructions for delivering at least one of the preparation of ammonia oxidizing bacteria and the activator to the subject. In some embodiments, the weight of the delivery device is less than about 50, 100, 200, 300, 400, 500, 600, 700, 800, 900, 1000, 1500, or 2000 grams.

In some embodiments, the kit may comprise a delivery device, wherein the first chamber and the second chamber are configured such that the barrier is not fixed relative to the first chamber and the second chamber. In some embodiments, the kit may comprise a delivery device, wherein the first chamber and the second chamber are configured such that the barrier is at least partially common to the first chamber and the second chamber. In some embodiments, the kit may comprise a delivery device, wherein the first chamber comprises a first housing and a first lumen, and the second chamber comprises a second housing and a second lumen. In some embodiments, the first housing and the second housing are fixed relative to each other. In some embodiments, a portion of the first housing and the second housing is shared by the first chamber and the second chamber. In some embodiments, the portion comprises a barrier. In some embodiments, the first housing and the second housing move independently from one another.

In some embodiments, a kit is provided comprising a first cosmetic and a second cosmetic, wherein the first cosmetic comprises ammonia oxidizing bacteria. In some embodiments, the second cosmetic comprises ammonia oxidizing bacteria.

In some embodiments, the kit may comprise at least one of a first cosmetic and a second cosmetic comprising at least one of a baby product, e.g., a baby shampoo, a baby lotion, a baby oil, a baby powder, a baby cream; a bath preparation, e.g., a bath oil, a tablet, a salt, a bubble bath, a bath capsule; an eye makeup preparation, e.g., an eyebrow pencil, an eyeliner, an eye shadow, an eye lotion, an eye makeup remover, a mascara; a fragrance preparation, e.g., a colognes, a toilet water, a perfume, a powder (dusting and talcum), a sachet; hair preparations, e.g., hair conditioners, hair sprays, hair straighteners, permanent waves, rinses, shampoos, tonics, dressings, hair grooming aids, wave sets; hair coloring preparations, e.g., hair dyes and colors, hair tints, coloring hair rinses, coloring hair shampoos, hair tighteners with color, hair bleaches; makeup preparations, e.g., face powders, foundations, leg and body paints, lipstick, makeup bases, rouges, makeup fixatives; manicuring preparations, e.g., basecoats and undercoats, cuticle softeners, nail creams and lotions, nail extenders, nail polish and enamel, nail polish and enamel removers; oral hygiene products, e.g., dentrifices, mouthwashes and breath fresheners; bath soaps and detergents, deodorants, douches, feminine hygiene deodorants; shaving preparations, e.g., aftershave lotions, beard softeners, talcum, preshave lotions, shaving cream, shaving soap; skin care preparations, e.g., cleansing, depilatories, face and neck, body and hand, foot powders and sprays, moisturizing, night preparations, paste masks, skin fresheners; and suntan preparations, e.g., gels, creams, and liquids, and indoor tanning preparations.

In some embodiments, this disclosure provides, inter alia, a method of providing a preparation of ammonia oxidizing bacteria, or preserving a preparation of ammonia oxidizing bacteria, comprising. The method may comprise culturing ammonia oxidizing bacteria under a carbon dioxide concentration sufficiently low, and an oxygen concentration and an amino acid concentration sufficiently high such that the ammonia oxidizing bacteria accumulate polyphosphate, thereby providing a preparation of ammonia oxidizing bacteria, or preserving a preparation of ammonia oxidizing bacteria.

In some embodiments, culturing may comprise contacting a sample of ammonia oxidizing bacteria with a culture medium having a pH of about 7.4 or less, a concentration of at least one of ammonia, ammonium ions, and urea of between about 10 micromolar and about 200 millimolar, in an environment having a carbon dioxide concentration of less than about 200 ppm, and an oxygen concentration of between about 5% to about 100% saturation In some embodiments, culturing may comprise contacting the sample of ammonia oxidizing bacteria with a culture medium having greater than 10 micromolar phosphate. In some embodiments, culturing comprises contacting the sample of ammonia oxidizing bacteria with a culture medium having between about 0.1 micromolar and 20 micromolar iron.

In some embodiments, contacting the sample may comprise contacting the sample for a pre-determined period of time. The pre-determined period of time may be at least partially based on a period of time of about 0.2-10 times, 0.3-5 times, 0.5-3 times, 0.5-1.5 times, or 0.5 to 1 times the doubling time for the ammonia oxidizing bacteria. The pre-determined period of time may be at least partially based on a period of time of about one doubling time for the ammonia oxidizing bacteria. In some embodiments, the pre-determined period of time is between about 8 hours and 12 hours. In some embodiments, the pre-determined period of time is about 10 hours.

In some embodiments, the sample of ammonia oxidizing bacteria is in a growth state.

In some embodiments, the method may comprise further contacting the sample of ammonia oxidizing bacteria with a culture medium having a pH of about 7.4 or less, a concentration of at least one of ammonia, ammonium ions, and urea of between about 10 micromolar and about 100 micromolar, in an environment having a carbon dioxide concentration of less than about 400 ppm, and an oxygen concentration of between about 0% to about 100% saturation.

In some embodiments a composition may be provided ammonia oxidizing bacteria preserved by the methods as described herein.

In some embodiments, this disclosure provides, inter alia, a method of reviving ammonia oxidizing bacteria from a storage state for use comprising providing the composition as described above, and contacting a sample of the composition with a culture medium having a pH of at least about 7.6, a concentration of at least one of ammonia, ammonium ions, and urea of between about 10 micromolar and about 100 millimolar, in an environment having a carbon dioxide concentration of about 200 ppm to about 5% saturation, and an oxygen concentration of between about 5% saturation and about 100% saturation.

In some embodiments, contacting the sample comprises contacting the sample for a pre-determined period of time. In some embodiments, the pre-determined period of time is less than about 72 hours. In some embodiments, the pre-determined period of time is less than about 70, 65, 60, 55, 50, 45, 40, 35, 30, 25, 20, 15, 10, 5, 4, 3, 2, 1, 0.5, 0.25, 0.1 hours. In some embodiments the culture medium further comprises a buffer and/or a media and/or at least one of ammonia, ammonium ions, and urea.

In some embodiments, a composition is provided comprising ammonia oxidizing bacteria revived by the methods described above.

In some embodiments, this disclosure provides, inter alia, a method of delivering ammonia oxidizing bacteria to a subject comprising providing a preparation of ammonia oxidizing bacteria, providing an activator, and combining the preparation of ammonia oxidizing bacteria and the activator. The method may further comprise administering the preparation of ammonia oxidizing bacteria and the activator to the subject. In some embodiments, a method is provided wherein the combining of the preparation of ammonia oxidizing bacteria and the activator may occur prior to delivery, e.g., in a container or a delivery device, to the subject. In some embodiments, a method is provided wherein the combining of the preparation of ammonia oxidizing bacteria and the activator occurs at the time of delivery, e.g., at a surface of the subject. In some embodiments, the method comprises using the container as described herein or the composition as described herein. In some embodiments, the method comprises using the kit as described herein.

In some embodiments, this disclosure provides, inter alia, a method of providing a preparation of ammonia oxidizing bacteria comprising providing a container as described herein, and transferring the preparation of ammonia oxidizing bacteria and the activator to provide activated ammonia oxidizing bacteria, e.g., ammonia oxidizing bacteria in a growth state. The method may further comprise actuating a barrier. Actuating the barrier may comprise disrupting the barrier. In some embodiments, upon actuating, the preparation of ammonia oxidizing bacteria and the activator may mix or contact one another. In some embodiments, the preparation of ammonia oxidizing bacteria and the activator may mix or contact one another in a mixing chamber. In some embodiments, the activated ammonia oxidizing bacteria, upon actuation, is deposited on a surface of a body. In some embodiments, the preparation of ammonia oxidizing bacteria is delivered to the surface prior to delivery of the activator. In some embodiments, the activator is delivered to the surface prior to the preparation of ammonia oxidizing bacteria. In some embodiments, the preparation of ammonia oxidizing bacteria and the activator are delivered simultaneously.

In some embodiments, the surface of the body is a portion of skin. The portion may be a facial area. The portion may be a lip. The portion may be an underarm.

In some embodiments, the method may be used for the treatment of at least one of HIV, dermatitis, infection in an ulcer, e.g., venous ulcer, e.g., leg ulcer, e.g., venous leg ulcer, e.g. infection in a diabetic foot ulcer, atopic dermatitis, acne, e.g., acne vulgaris, eczema, contact dermatitis, allergic reaction, psoriasis, uticaria, rosacea, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, pneumonia, primary immunodeficiency, epidermal lysis bulosa or cancer. In embodiments, the condition is a venous leg ulcer.

In some embodiments, the method may be used for treating or preventing a skin disorder, a treatment or prevention of a disease or condition associated with low nitrite levels, a treatment or prevention of body odor, a treatment to supply nitric oxide to a subject, or a treatment to inhibit microbial growth.

In some embodiments, this disclosure provides, inter alia, a preparation comprising an ammonia oxidizing bacteria and formulated such that no more than 10%, 20%, 30%, 40%, 50%, 60%, or 70% of the ability to oxidize $NH_4^+$ is lost upon storage at selected conditions. The preparation may comprise the composition of ammonia oxidizing bacteria as described herein. The preparation may be prepared by the methods described herein. The selected conditions may comprise a culture medium having a pH of less than about 7.4. The preparation may be selected to provide a reduced level of carbon dioxide, or no carbon dioxide, e.g., conditions in a polyphosphate loading state, or a storage state.

In some embodiments, the selected conditions comprise a culture medium having a pH of about 7.4 or less, a concentration of at least one of ammonia, ammonium ions, and urea of between about 10 micromolar and about 100 micromolar, in an environment having a carbon dioxide concentration of less than about 400 ppm, and an oxygen concentration of between about 0% to about 100% saturation; or a culture medium having a pH of about 7.4 or less, a concentration of at least one of ammonia, ammonium ions, and urea of between about 10 micromolar and about 200 millimolar, in an environment having a carbon dioxide concentration of less than about 200 ppm, and an oxygen concentration of between about 5% to about 100% saturation.

In some embodiments, the preparation may have less than about 0.01% to about 10% of surfactant. In some embodiments, the preparation may be substantially free of surfactant. In some embodiments, the preparation may be substantially free of sodium dodecyl sulfate. In some embodiments, the preparation may comprise a chelator. In some embodiments, the preparation may be substantially free of chelator.

In some embodiments, the preparation may be adapted for use as a cosmetic product. In some embodiments, the preparation may be adapted for use as a therapeutic product. In some embodiments, the preparation may be disposed in at least one of a baby product, e.g., a baby shampoo, a baby lotion, a baby oil, a baby powder, a baby cream; a bath preparation, e.g., a bath oil, a tablet, a salt, a bubble bath, a bath capsule; an eye makeup preparation, e.g., an eyebrow pencil, an eyeliner, an eye shadow, an eye lotion, an eye makeup remover, a mascara; a fragrance preparation, e.g., a colognes, a toilet water, a perfume, a powder (dusting and talcum), a sachet; hair preparations, e.g., hair conditioners, hair sprays, hair straighteners, permanent waves, rinses, shampoos, tonics, dressings, hair grooming aids, wave sets; hair coloring preparations, e.g., hair dyes and colors, hair tints, coloring hair rinses, coloring hair shampoos, hair tighteners with color, hair bleaches; makeup preparations, e.g., face powders, foundations, leg and body paints, lipstick, makeup bases, rouges, makeup fixatives; manicuring preparations, e.g., basecoats and undercoats, cuticle softeners, nail creams and lotions, nail extenders, nail polish and enamel, nail polish and enamel removers; oral hygiene products, e.g., dentrifices, mouthwashes and breath fresheners; bath soaps and detergents, deodorants, douches, feminine hygiene deodorants; shaving preparations, e.g., aftershave lotions, beard softeners, talcum, preshave lotions, shaving cream, shaving soap; skin care preparations, e.g., cleansing, depilatories, face and neck, body and hand, foot powders and sprays, moisturizing, night preparations, paste masks, skin fresheners; and suntan preparations, e.g., gels, creams, and liquids, and indoor tanning preparations.

In some embodiments, the preparation may be used for treatment of at least one of HIV dermatitis, infection in an ulcer, e.g., venous ulcer, e.g., leg ulcer, e.g., venous leg ulcer, e.g. infection in a diabetic foot ulcer, atopic dermatitis, acne, e.g., acne vulgaris, eczema, contact dermatitis, allergic reaction, psoriasis, uticaria, rosacea, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, pneumonia, primary immunodeficiency, epidermal lysis bulosa or cancer. In embodiments, the condition is a venous leg ulcer.

In some embodiments, the preparation of ammonia oxidizing bacteria may comprise, consist essentially of, or consist of ammonia oxidizing bacteria in a buffer solution comprising, consisting essentially of, or consisting of disodium phosphate and magnesium chloride, for example, 50 mM $Na_2HPO_4$ and 2 mM $MgCl_2$. The preparation is provided in a container constructed to contain between about 0.1 and about 100 fluid ounces, about 0.2 and about 50 fluid ounces, about 0.5 and about 25 fluid ounces, about 1.0 and about 10 fluid ounces, about 2.0 and about 7 fluid ounces, about 3 and about 5 fluid ounces. In some embodiments, the preparation is a container constructed to contain about 3.4 fluid ounces. The container may be a one-chamber container, or any other container disclosed herein.

Ammonia oxidizing bacteria are ubiquitous Gram-negative obligate chemolithoautotrophic bacteria with a unique capacity to generate energy exclusively from the conversion of ammonia to nitrite.

In some embodiments, ammonia oxidizing bacteria catalyze the following reactions.

At a neutral pH, ammonia generated from ammonium around neutral pH conditions is the substrate of the initial reaction. The conversion of ammonia to nitrite takes place in two steps catalyzed respectively by ammonia monooxygenase (Amo) and hydroxylamine oxidoreductase (Hao), as follows:

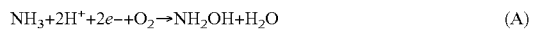  (A)

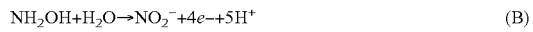  (B)

In some instances, reaction B is reported as follows, to indicate nitrous acid ($HNO_2$) formation at low pH:

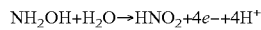

In certain embodiments, $NH_4^+$ and $NH_3$ may be used interchangeably throughout the disclosure.

The disclosure contemplates all combinations of any one or more of the foregoing aspects and/or embodiments, as well as combinations with any one or more of the embodiments set forth in the detailed description and examples.

DETAILED DESCRIPTION

Figure 1:
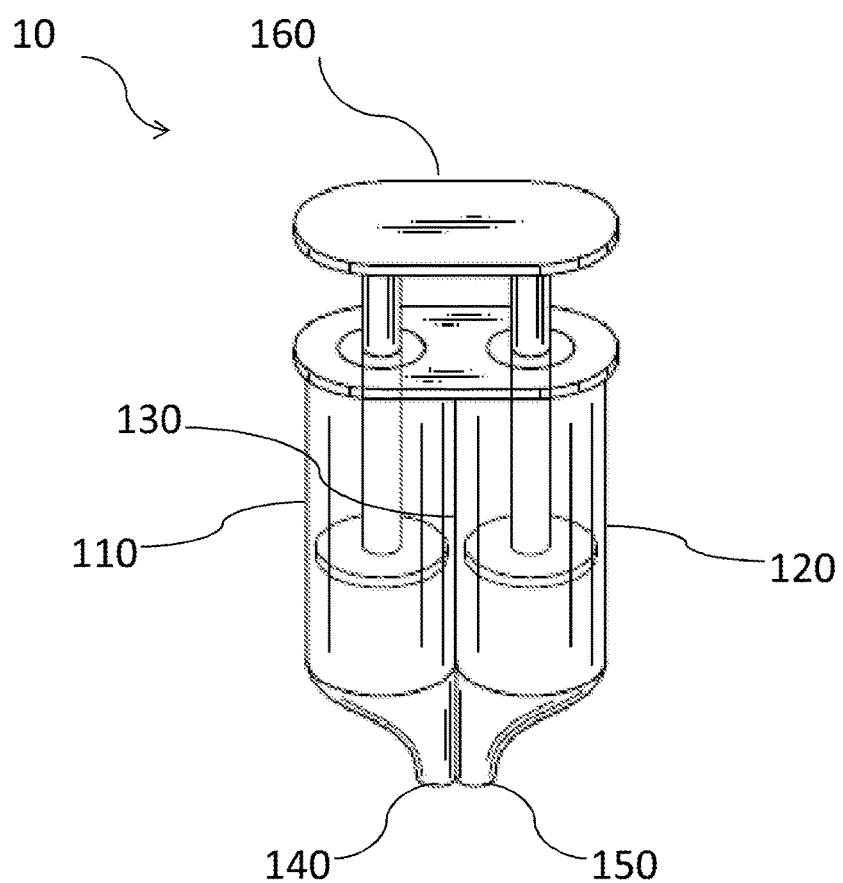
FIG. 1 shows a perspective view of a container in accordance with some embodiments of the disclosure.

The systems and methods of the disclosure provide, inter alia, for delivery of ammonia oxidizing bacteria with ammonia, ammonium ions, and urea. This may provide for optimized delivery to accelerate the availability of bacteria, e.g., activated bacteria, e.g., ammonia oxidizing bacteria in a growth state, and its products, e.g., nitrite and/or nitric oxide and/or nitric oxide precursors. The systems and methods may provide, inter alia, for establishment of a colony of ammonia oxidizing bacteria, e.g., providing a stable replicating colony of ammonia oxidizing bacteria, e.g., on a surface of a subject, e.g., topically. The systems and methods may provide an activator, e.g., one or more of ammonia, ammonium ions, and urea at or near a time of delivery of the ammonia oxidizing bacteria to an environment, e.g., a subject, e.g., a surface of a subject. This may promote efficiency of the delivery (application or administration), and help establish a colony in the environment to promote effective establishment of a colony. This may also provide enhanced abilities of the ammonia oxidizing bacteria to convert ammonia into nitrite, NO and precursors, as well as compete with other existing bacteria by providing an immediate environment that favors ammonia oxidizing bacteria.

1. Definitions

An ammonia oxidizing bacterium refers to a bacterium capable of oxidizing ammonia or ammonium to nitrite. This may be accomplished at a rate. The rate, e.g., a predetermined rate, may refer to the conversion of ammonium ions ($NH_4^+$) (e.g., at about 200 mM) to nitrite ($NO_2^-$) at a rate of at least 50, 75, 125, or 150 micromoles $NO_2^-$ per minute, e.g., about 100-150, 75-175, 75-125, 100-125, 125-150, or 125-175 micromoles/minute, e.g., about 125 micromoles $NO_2^-$ per minute. Examples of ammonia oxidizing bacteria include *Nitrosomonas eutropha* strains, e.g., D23 and C91, and other bacteria in the genera *Nitrosomonas, Nitrosococcus, Nitrosospira, Nitrosocystis, Nitrosolobus,* and *Nitrosovibrio*. D23 *Nitrosomonas eutropha* strain refers to the strain, designated AOB D23-100, deposited with the American Tissue Culture Collection (ATCC) (10801 University Blvd., Manassas, Va., USA) on Apr. 8, 2014 having accession number PTA-121157. The nucleic acid sequence(s), e.g., genome sequence, of accession number PTA-121157 are hereby incorporated by reference in their entireties. In certain embodiments, the *N. eutropha* is a strain described in PCT Application No. PCT/US2015/025909, filed Apr. 15, 2015, herein incorporated by reference in its entirety.

As used herein, "axenic" refers to a composition comprising an organism that is substantially free of other organisms. For example, an axenic culture of ammonia oxidizing bacteria is a culture that is substantially free of organisms other than ammonia oxidizing bacteria. In some embodiments, "substantially free" denotes undetectable by a method used to detect other organisms, e.g., plating the culture and examining colony morphology, or PCR for a conserved gene such as 16S RNA. An axenic composition may comprise elements that are not organisms, e.g., it may comprise nutrients or excipients. Any embodiment, preparation, composition, or formulation of ammonia oxidizing bacteria discussed herein may comprise, consist essentially of, or consist of optionally axenic ammonia oxidizing bacteria.

As used herein, an "autotroph", e.g., an autotrophic bacterium, is any organism capable of self-nourishment by using inorganic materials as a source of nutrients and using photosynthesis or chemosynthesis as a source of energy. Autotrophic bacteria may synthesize organic compounds from carbon dioxide and ATP derived from other sources, coxiation of ammonia to nitrite, oxidation of hydrogen sulfide, and oxidation of $Fe^{2+}$ to $Fe^{3+}$. Autotrophic bacteria of the present disclosure are incapable of causing infection.

To "culture" refers to a process of placing an amount of a desired bacterium under conditions that promote its growth, i.e., promoting cell division. The conditions can involve a specified culture medium, a set temperature range, and/or an agitation rate. Bacteria can be cultured in a liquid culture or on plates, e.g., agar plates.

"Activation," as used herein, is used relative to autotrophic bacteria, e.g., ammonia oxidizing bacteria. Activation refers to any action that may place the ammonia oxidizing bacteria in a potentially more active state, e.g., a growth state. Activation may relate to stimulation of autotrophic bacteria, e.g., ammonia oxidizing bacteria, to assist in some way in the conversion of at least one of ammonia, ammonium ions, and urea into nitrite, nitric oxide, or nitric oxide precursors. Activation may relate to helping establish a bacterial colony, e.g., to allow for the autotrophic bacteria, e.g., ammonia oxidizing bacteria, to compete with other existing bacteria. Activation may relate to providing an environment that may favor sustainability and/or growth of autotrophic bacteria, e.g., ammonia oxidizing bacteria. Activation may relate to accelerating availability of the autotrophic bacteria, e.g., ammonia oxidizing bacteria to an environment or a surface. "Activation" may provide for ammonia oxidizing bacteria to be in an "activated" or "growth state." "Activation" may take place with the use of an activator. The ammonia oxidizing bacteria may come into contact with the activator to provide an ammonia oxidizing bacteria in an "activated" or "growth" state. This may occur within or outside of a container, delivery device, or delivery system, e.g., within the first chamber, the second chamber, a mixing chamber, a third or additional chamber, or combinations thereof. The activator may be at least one of ammonia, ammonium ions, or urea. The activator may be an ammonium salt, e.g., ammonium chloride or ammonium sulfate. The concentration of the activator, e.g., ammonium salt, e.g., ammonium chloride or ammonium sulfate may be in a range of about 10 micromolar to about 100 millimolar. In certain aspects the concentration of the activator, e.g., ammonium salt, e.g., ammonium chloride or ammonium sulfate may be in a range of about 0.5 mM to about 50 mM. The activator may be in a solution, suspension, a powder, e.g., crystalline form, a media, a buffer, or disposed in or provide as a suitable carrier for maintaining the activator. The ammonia oxidizing bacteria may be in any suitable form for maintaining the AOB in a desired state, e.g., a storage state, e.g., an aqueous suspension, gel, or powder form. The at least one of ammonia, ammonium ions, or urea may be in a medium or a buffer to promote growth of ammonia oxidizing bacteria, e.g., an AOB media or a growth media. A time-release, or controlled release urea may be used as an activator.

"Actuation," as used herein, means that some action is being taken, e.g., a process is being started or something is being put into motion. In some embodiments, actuation may refer to the breaking of a barrier of a container, mixing of the contents of the container, or the initiation of movement of one or more contents of a container, e.g., delivery of one or more contents of the container to outside of the container, e.g., to a surface or an environment. In some embodiments, actuation may the barrier comprising one or more materials to degrade over time that will allow contact of contents of the first chamber and the second chamber, e.g., a controlled release of contents of the first chamber, or a controlled release of contents from the second chamber, or both.

A "barrier," as used herein, may mean any structure or configuration that may serve to obstruct passage or to maintain separation, e.g., between a first chamber and a second chamber of a container. The barrier may be in the form of a valve, e.g., a check valve, filtering material, film, wax, lipid, polymer, or controlled release material, e.g., slow release material. The barrier may be a material that upon actuation of a container, it may allow passage of contents from a first chamber into a second chamber, passage of contents from a second chamber into a first chamber, or both. The barrier may be disrupted upon actuation, e.g., through piercing, puncturing, stabbing, perforating, penetrating, splitting, opening or tearing the barrier. The barrier may be in a form of a valve, e.g., a check valve, a flexible or inflexible material that may not degrade upon contact with one or more contents of the container, or a flexible or inflexible material that may degrade upon contact with one or more contents of the container, a filter material. The barrier may be made of any material suitable for its purpose, e.g., a material that may serve to obstruct passage or to maintain separation, e.g., a polymeric material or metal material.

In some embodiments, the states most relevant to the present disclosure are the state of growth, e.g., maximal growth, characterized by a pH of at least about 7.6, ammonia, trace minerals, oxygen and carbon dioxide. Another state may be characterized by a pH of about 7.4 or less and characterized by an absence of carbon dioxide. Under low carbon dioxide conditions, ammonia oxidizing bacteria, e.g., *Nitrosomonas*, continues to oxidize ammonia into nitrite and generates ATP, but lacking carbon dioxide, e.g., lacking sufficient carbon dioxide, to fix and generate protein, it instead generates polyphosphate, which it uses as an energy storage medium. This may allow the ammonia oxidizing bacteria to remain in a "storage state" for a period of time, e.g., a pre-determined period of time, for example, at least 1, 2, 3, 4, 5, 6, 7, days, 1, 2, 3, 4 weeks, 1, 2, 3, 4, 5, 6, 7, 8, 9, 10, 11, 12 months, 1, 2, 3, 4, or 5 years. In some embodiments, the ammonia oxidizing bacteria may remain in a storage state for at least about 6 months to about 1 year.

As used herein, "growth state" refers to autotrophic bacteria, e.g., ammonia oxidizing bacteria, in a state or in an environment, e.g., a media, e.g., a culture media, e.g., a growth media, that may have a pH of at least about 7.6. Levels of at least one of ammonia, ammonium ions, and urea may be between about 1 micromolar and 1000 millimolar. Levels of trace materials are between about 0.01 micromolar iron and 200 micromolar iron. Levels of oxygen are between about 5% and 100% oxygen saturation (e.g., of media). Levels of carbon dioxide are between about 20 ppm and 10% saturation (e.g., of media). In certain aspects, levels of at least one of ammonia, ammonium ions, and urea may be between about 10 micromolar and 100 millimolar. Levels of trace materials are between about 0.1 micromolar iron and 20 micromolar iron. Levels of oxygen are between about 5% and 100% oxygen saturation. Levels of carbon dioxide are between about 200 ppm and 5% saturation (e.g., of media).

As used herein, "polyphosphate loading state" refers to autotrophic bacteria, e.g., ammonia oxidizing bacteria, in a state or in an environment, e.g., a media, e.g., a culture media, e.g., a growth media, that may have a pH of about 7.4, or less. Levels of at least one of ammonia, ammonium ions, and urea are between about 1 micromolar and 2000 millimolar. Levels of trace materials are between 0.01 micromolar iron and 200 micromolar iron. Levels of oxygen are between about 0% and 100% $O_2$ saturation (e.g., of media). Levels of carbon dioxide are between/less than about zero and 400 ppm, and phosphate levels greater than about 1 micromolar. In certain aspects, levels of at least one of ammonia, ammonium ions, and urea are between about 10 micromolar and 200 millimolar. Levels of trace materials are between 0.1 micromolar iron and 20 micromolar iron. Levels of oxygen are between about 5% and 100% $O_2$ saturation. Levels of carbon dioxide are between/less than about zero and 200 ppm, and phosphate levels greater than about 10 micromolar.

A purpose of the polyphosphate loading state may be to provide AOB with sufficient ammonia, ammonium ions, and/or urea, and $O_2$ such that ATP can be produced, but to deny them $CO_2$ and carbonate such that they are unable to use that ATP to fix $CO_2$ and instead use that ATP to generate polyphosphate which may be stored by the bacteria.

As used herein, the term "storage state" refers to autotrophic bacteria, e.g., ammonia oxidizing bacteria, in a state or in an environment, e.g., a media, e.g., a culture media, e.g., a growth media, having a pH of about 7.4 or less (in some embodiments, the pH may be 7.6 or less). Levels of at least one of ammonia, ammonium ions, and urea are between about 1 and 1000 micromolar. Levels of trace materials are between about 0.1 and 100 micromolar. Levels of oxygen are between about 0 and 100% saturation (e.g., of media). Levels of carbon dioxide are between about 0 and 800 ppm. In certain aspects, levels of at least one of ammonia, ammonium ions, and urea are between about 10 and 100 micromolar. Levels of trace materials are between about 1 and 10 micromolar. Levels of oxygen are between about 0 and 100% saturation (e.g., of media). Levels of carbon dioxide are between about 0 and 400 ppm.

AOB are produced according to some embodiments of the present disclosure by generating AOB biomass during a growth state, then exposing the AOB to a polyphosphate loading state and then removing the media and resuspending the AOB in a buffer, e.g., a storage buffer (i.e., the storage state).

Administered "in combination," as used herein, means that two (or more) different treatments are delivered to the subject during the course of the subject's affliction with the disorder, e.g., the two or more treatments are delivered after the subject has been diagnosed with the disorder and before the disorder has been cured or eliminated. In some embodiments, the delivery of one treatment is still occurring when the delivery of the second begins, so that there is overlap. This is sometimes referred to herein as "simultaneous" or "concomitant" or "concurrent delivery". In other embodiments, the delivery of one treatment ends before the delivery of the other treatment begins. This is sometimes referred to herein as "successive" or "sequential delivery" or "consecutive delivery." In embodiments of either case, the treatment is more effective because of combined administration. For example, the second treatment is a more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive (i.e., synergistic). The delivery can be such that an effect of the first treatment delivered is still detectable when the second is delivered.

A "natural product" is or may comprise a product that may be at least partially derived from nature. It may be anything or comprise anything produced by a living organism, and may include organisms themselves. Natural products may include or comprise an entire organism, and part of an organism (e.g., a leaf of a plant), an extract from an organism, an organic compound from an organism, a purified organic compound from an organism. Natural products may be or comprise organic substances found and cells, including primary metabolites (amino acids, carbohydrates, and nucleic acids) and secondary metabolites (organic compounds found in a limited range of species, e.g., polyketides, fatty acids, terpenoids, steroids, phenylpropanoids, alkaloids, specialized amino acids and peptides, specialized carbohydrates). Natural products may be or comprise polymeric organic materials such as cellulose, lignin, and proteins.

Natural products may be or comprise products for commercial purposes, and may refer to cosmetics, dietary supplements, and foods produced from natural sources. Natural products may have pharmacological or biological activity that may be of therapeutic benefit, e.g., in treating disease or conditions. Natural products may be included in traditional medicines, treatments for cosmetological purposes, and spa treatments. A natural product referred to herein may comprise any one or more of the components described as a natural product to be incorporated into a preparation or formulation comprising one or more other components, e.g., excipients. The preparation or formulation referred to as a natural product may comprise a natural product defined herein and one or more additional components or ingredients. Any of the compositions, preparations, or formulations discussed throughout this disclosure may be or comprise one or more natural products.

The terms "polypeptide", "peptide" and "protein" (if single chain) are used interchangeably herein to refer to amino acid polymers. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. The polypeptide can be isolated from natural sources, can be a produced by recombinant techniques from a eukaryotic or prokaryotic host, or can be a product of synthetic procedures.

As used herein, "presence" or "level" may refer to a qualitative or quantitative amount of a component, e.g., any one or more of an ammonia oxidizing bacteria, ammonia, ammonium ions, urea, nitrite, or nitric oxide. The presence or level may include a zero value or a lack of presence of a component.

As used herein, the term "surfactant", includes compounds that may lower the surface tension, or interfacial tension, between two liquids or between a liquid and a solid. Surfactants may act as detergents, wetting agents, emulsifiers, foaming agents, and dispersants. Surfactants may include one or more of the following, alone, or in combination with those listed, or other surfactants or surfactant-like compounds: cocamidopropyl betaine (ColaTeric COAB), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g., Rhoda-Pex ESB 70 NAT), alkyl polyglucoside (e.g., Plantaren 2000 N UP), sodium laureth sulfate (Plantaren 200), Dr. Bronner's Castile soap, Dr. Bronner's baby soap, Lauramine oxide (ColaLux Lo), sodium dodecyl sulfate (SDS), polysulfonate alkyl polyglucoside (PolySufanate 160 P), sodium lauryl sulfate (Stepanol-WA Extra K) and combinations thereof. Dr. Bronner's Castile soap and baby soap comprises water, organic coconut oil, potassium hydroxide, organic olive oil, organic fair deal hemp oil, organic jojoba oil, citric acid, and tocopherol.

As used herein, "transgenic" means comprising one or more exogenous portions of DNA. The exogenous DNA is derived from another organism, e.g., another bacterium, a bacteriophage, an animal, or a plant.

As used herein, "treatment of a disease or condition" refers to reducing the severity or frequency of at least one symptom of that disease or condition, compared to a similar but untreated patient. Treatment can also refer to halting, slowing, or reversing the progression of a disease or condition, compared to a similar but untreated patient. Treatment may comprise addressing the root cause of the disease and/or one or more symptoms.

As used herein a "therapeutically effective amount" refers to a dose sufficient to prevent advancement, or to cause regression of a disease or condition, or which is capable of relieving a symptom of a disease or condition, or which is capable of achieving a desired result. A therapeutically effective dose can be measured, for example, as a number of bacteria or number of viable bacteria (e.g., in CFUs) or a mass of bacteria (e.g., in milligrams, grams, or kilograms), or a volume of bacteria (e.g., in $mm^3$).

As used herein, the term "viability" refers to the autotrophic bacteria's, e.g., ammonia oxidizing bacteria's, ability to oxidize ammonia, ammonium, or urea to nitrite at a pre-determined rate. In some embodiments, the rate refers to the conversion of ammonium ions ($NH_4^+$) (e.g., at about 200 mM) to nitrite ($NO_2^-$) at a rate of at least 50, 75, 125, or 150 micromoles $NO_2^-$ per minute, e.g., about 100-150, 75-175, 75-125, 100-125, 125-150, or 125-175 micromoles/minute, e.g., about 125 micromoles $NO_2^-$ per minute.

"Growth media" or "AOB media," as referred to herein comprises the following components of Table 1 or Table 2:

TABLE 1

| | Weight/Volume (in~1.5 L) | Final Concentration (in~1.5 L) |
|---|---|---|
| $(NH_4)_2SO_4$ (MW 132.14) | 4.95 g | 50 mM $NH_4^+$ |
| $KH_2PO_4$ (MW 136.1) | 0.616 g | 3.0 mM |
| 1M $MgSO_4$ | 1.137 ml | 0.76 mM |
| 1M $CaCl_2$ | 0.3 ml | 0.2 mM |
| 30 mM $FeCl_3$/50 mM EDTA | 0.5 ml | 10 μM/16.7 μM |
| 50 mM $CuSO_4$ | 30 μl | 1.0 μM |
| Add 1400 ml dd$H_2O$ to flask. Autoclave. Store at room temperature. After autoclaving add: | | |
| Phosphate Buffer | 100 ml | 32 mM $KH_2PO_4$/ 2.7 mM $NaH_2PO_4 \cdot H_2O$ |
| 5% $Na_2CO_3$ | 12 ml | 0.04% |

TABLE 2

| | Batch medium Weight/Volume (1 L) (Final concentration) | Feeding solution Weight/Volume (1 L) (Final concentration) |
|---|---|---|
| $(NH_4)_2SO_4$ (MW 132.14) | 3.3 g (50 mM $NH_4^+$) | 13.2 g (200 mM $NH_4^+$) |
| $KH_2PO_4$ (MW 136.1) | 1.23 g (9.0 mM) | 0.41 g (3.0 mM) |
| 1M $MgSO_4$ | 0.758 ml (0.76 mM) | 0.758 ml (0.76 mM) |
| 1M $CaCl_2$ | 0.2 ml (0.2 mM) | 0.2 ml (0.2 mM) |

TABLE 2-continued

| | Batch medium Weight/Volume (1 L) (Final concentration) | Feeding solution Weight/Volume (1 L) (Final concentration) |
|---|---|---|
| 30 mM FeCl$_3$/50 mM EDTA | 0.333 ml (10 µM/16.7 µM) | 0.333 ml (10 µM/16.7 µM) |
| 50 mM CuSO$_4$ | 20 µl (1.0 µM) | 20 µl (1.0 µM) |
| ddH$_2$O | 1000 ml | 1000 ml |
| Autoclave each solution and store at room temperature. | | |

2. Ammonia Oxidizing Bacteria (AOBs)

Autotrophic ammonia oxidizing bacteria, which may be referred to herein as AOBs or AOB, are obligate autotrophic bacteria as noted by Alan B. Hooper and A. Krummel at al. Alan B. Hooper, Biochemical Basis of Obligate Autotrophy in *Nitrosomonas europaea*, Journal of Bacteriology, February 1969, p. 776-779. Antje Krummel et al., Effect of Organic Matter on Growth and Cell Yield of Ammonia-Oxidizing Bacteria, Arch Microbiol (1982) 133: 50-54. These bacteria derive all metabolic energy only from the oxidation of ammonia to nitrite with nitric oxide (NO) as an intermediate product in their respiration chain and derive virtually all carbon by fixing carbon dioxide. They are incapable of utilizing carbon sources other than a few simple molecules.

Ammonia oxidizing bacteria (AOB) are widely found in the environment, and in the presence of ammonia, oxygen and trace metals will fix carbon dioxide and proliferate. AOB may be slow growing and toxic levels of ammonia may kill fish and other organisms before AOB can proliferate and reduce ammonia to non-toxic levels. Slow growth of AOB also may delay the health benefits of the NO and nitrite the AOB produce when applied to the skin.

Supplementing the aquarium, skin, or process with sufficient viable AOB grown and stored for that purpose is desired. AOB do not form spores, so storage in the dry state with high viability is difficult, and storage in the wet state leaves them metabolically active.

Decay of nitrifying capacity during storage of AOB for wastewater treatment has been studied, as for example (Munz G, Lubello C, Oleszkiewicz J A. Modeling the decay of ammonium oxidizing bacteria. Water Res. 2011 January; 45(2): 557-64. Oi: 10.1016/j.watres.2010.09.022.)

Growth, prolonged storage, and restoration of activity of *Nitrosomonas* is discussed by Cassidy et al. (U.S. Pat. No. 5,314,542) where they disclose growing *Nitrosomonas*, removing toxic waste products, storing in sterile water of appropriate salinity for periods of time up to one year, and then reviving by adding buffer (CaCO$_3$) and 200 ppm, of ammonium, which reviving takes 72 hours.

The present disclosure provides that if AOB are kept under conditions of low carbon dioxide but with sufficient oxygen and ammonia, where they accumulate polyphosphate for a period of about one doubling time (~10 hours), then they accumulate sufficient polyphosphate to greatly extends their storage viability, storage time and accelerate their revival both with and without addition of buffer and ammonia.

The presence of sufficient stored polyphosphate allows AOB the ATP resources to maintain metabolic activity even in the absence of ammonia and oxygen, and to survive insults that would otherwise be fatal.

As obligate autotrophs, AOB synthesize protein via the fixing of CO$_2$ using the energy and reducing equivalents generated by the oxidation of ammonia to nitrite. Growth requires ammonia, oxygen, minerals and carbon dioxide.

*Nitrosomonas* may exist in several metabolic states, according to "Polyphosphate and Orthophosphate Content of *Nitrosomonas europaea* as a Function of Growth" by K. R. Terry and A. B. Hooper, Journal of Bacteriology, July 1970, p. 199-206, Vol. 103, No. I.

The AOBs contemplated in this disclosure may comprise mutations relative to wild-type AOBs. These mutations may, e.g., occur spontaneously, be introduced by random mutagenesis, or be introduced by targeted mutagenesis. For instance, the AOBs may lack one or more genes or regulatory DNA sequences that wild-type AOBs typically comprises. The AOBs may also comprise point mutations, substitutions, insertions, deletions, and/or rearrangements relative to the sequenced strain or a wild-type strain. The AOBs may be a purified preparation of optimized AOBs.

In certain embodiments, the AOBs are transgenic. For instance, it may comprise one or more genes or regulatory DNA sequences that wild-type ammonia oxidizing bacteria lacks. More particularly, the ammonia oxidizing bacteria may comprise, for instance, a reporter gene, a selective marker, a gene encoding an enzyme, or a promoter (including an inducible or repressible promoter). In some embodiments the additional gene or regulatory DNA sequence is integrated into the bacterial chromosome; in some embodiments the additional gene or regulatory DNA sequence is situated on a plasmid.

In some preferred embodiments, the AOBs differ by at least one nucleotide from naturally occurring bacteria. For instance, the AOBs may differ from naturally occurring bacteria in a gene or protein that is part of a relevant pathway, e.g., an ammonia metabolism pathway, a urea metabolism pathway, or a pathway for producing nitric oxide or nitric oxide precursors. More particularly, the AOBs may comprise a mutation that elevates activity of the pathway, e.g., by increasing levels or activity of an element of that pathway.

The above-mentioned mutations can be introduced using any suitable technique. Numerous methods are known for introducing mutations into a given position. For instance, one could use site-directed mutagenesis, oligonucleotide-directed mutagenesis, or site-specific mutagenesis. Non-limiting examples of specific mutagenesis protocols are described in, e.g., Mutagenesis, pp. 13.1-13.105 (Sambrook and Russell, eds., Molecular Cloning A Laboratory Manual, Vol. 3, 3.sup.rd ed. 2001). In addition, non-limiting examples of well-characterized mutagenesis protocols available from commercial vendors include, without limitation, Altered Sites® II in vitro Mutagenesis Systems (Promega Corp., Madison, Wis.); Erase-a-Base® System (Promega, Madison, Wis.); GeneTailor™ Site-Directed Mutagenesis System (Invitrogen, Inc., Carlsbad, Calif.); QuikChange® II Site-Directed Mutagenesis Kits (Stratagene, La Jolla, Calif.); and Transformer™ Site-Directed Mutagenesis Kit (BD-Clontech, Mountain View, Calif.).

In some embodiments of the disclosure, the ammonia oxidizing bacteria may be axenic. The preparation, e.g., formulation, e.g., composition) of ammonia oxidizing bacteria may comprise, consist essentially of, or consist of axenic ammonia oxidizing bacteria. The ammonia oxidizing bacteria may be from a genus selected from the group consisting of *Nitrosomonas, Nitrosococcus, Nitrosospira, Nitrosocystis, Nitrosolobus, Nitrosovibrio*, and combinations thereof.

In some embodiments, the preparation of ammonia oxidizing bacteria may comprise a concentration or amount of ammonia oxidizing bacteria in order to at least partially treat a condition or disease. The preparation of ammonia oxidizing bacteria may comprise a concentration or amount of ammonia oxidizing bacteria in order to alter, e.g., reduce or increase, an amount, concentration or proportion of a bacterium, or genus of bacteria, on a surface, e.g., a skin surface. The bacteria may be non-pathogenic or pathogenic, or potentially pathogenic.

In some embodiments, the preparation of ammonia oxidizing bacteria may comprise between about $10^8$ to about $10^{14}$ CFU/L. The preparation may comprise at least $10^8$, $10^9$, $10^{10}$, $10^{11}$, $2\times10^{11}$, $5\times10^{11}$, $10^{12}$, $2\times10^{12}$, $5\times10^{12}$, $10^{13}$, $2\times10^{13}$, $5\times10^{13}$, or $10^{14}$; or about $10^8$-$10^9$, $10^9$-$10^{10}$, $10^{10}$-$10^{11}$, $10^{11}$-$10^{12}$, $10^{12}$-$10^{13}$, or $10^{13}$-$10^{14}$ CFU/L. In some embodiments, the preparation may comprise at least $10^8$, $10^9$, $10^{10}$, $10^{11}$, $2\times10^{11}$, $5\times10^{11}$, $10^{12}$, $2\times10^{12}$, $5\times10^{12}$, $10^{13}$, $2\times10^{13}$, $5\times10^{13}$, or $10^{14}$; or about $10^8$-$10^9$, $10^9$-$10^{10}$, $10^{10}$-$10^{11}$, $10^{11}$-$10^{12}$, $10^{12}$-$10^{13}$, or $10^{13}$-$10^{14}$ CFU/ml.

In certain aspects, the preparation may comprise between about $1\times10^9$ CFU to about $10\times10^9$ CFU. In certain aspects, the preparation may comprise between about $1\times10^9$ CFU/L to about $10\times10^9$ CFU/L.

In some embodiments, the preparation of ammonia oxidizing bacteria may comprise between about 0.1 milligrams (mg) to about 1000 mg of ammonia oxidizing bacteria. In certain aspects, the preparation may comprise between about 50 mg and about 1000 mg of ammonia oxidizing bacteria. The preparation may comprise between about 0.1-0.5 mg, 0.2-0.7 mg, 0.5-1.0 mg, 0.5-2 mg, 0.5-5 mg, 2.5-5 mg, 2.5-7.0 mg, 5.0-10 mg, 7.5-15 mg, 10-15 mg, 15-20 mg, 15-25 mg, 20-30 mg, 25-50 mg, 25-75 mg, 50-75 mg, 50-100 mg, 75-100 mg, 100-200 mg, 200-300 mg, 300-400 mg, 400-500 mg, 500-600 mg, 600-700 mg, 700-800 mg, 800-900 mg, 900-1000 mg, 100-250 mg, 250-500 mg, 100-500 mg, 500-750 mg, 750-1000 mg, or 500-1000 mg.

In some embodiments, the preparation of ammonia oxidizing bacteria may comprise a mass ratio of ammonia oxidizing bacteria to an excipient, e.g., a pharmaceutically acceptable excipient or a cosmetically acceptable excipient in a range of about 0.1 grams per liter to about 1 gram per liter. The preparation may comprise a mass ratio of ammonia oxidizing bacteria to an excipient in a range of about 0.1-0.2, 0.2-0.3, 0.1-0.5, 0.2-0.7, 0.5-1.0, or 0.7-1.0 grams per liter.

In some embodiments, the preparation of ammonia oxidizing bacteria may comprise, consist essentially of, or consist of ammonia oxidizing bacteria in a buffer solution comprising, consisting essentially of, or consisting of disodium phosphate and magnesium chloride, for example, 50 mM $Na_2HPO_4$ and 2 mM $MgCl_2$.

The preparation may comprise a volume of between about 0.1 and about 100 fluid ounces, about 0.2 and about 50 fluid ounces, about 0.5 and about 25 fluid ounces, about 1.0 and about 10 fluid ounces, about 2.0 and about 7 fluid ounces, about 3 and about 5 fluid ounces. In some embodiments, the preparation may comprise a volume of about 3.4 fluid ounces.

The preparation may be provided in a container constructed to contain between about 0.1 and about 100 fluid ounces, about 0.2 and about 50 fluid ounces, about 0.5 and about 25 fluid ounces, about 1.0 and about 10 fluid ounces, about 2.0 and about 7 fluid ounces, about 3 and about 5 fluid ounces. In some embodiments, the preparation is a container constructed to contain about 3.4 fluid ounces. The container may be a one-chamber container, or any other container disclosed herein.

In some embodiments, the preparation of ammonia oxidizing bacteria may be in a growth state. A growth state may be provided by exposing ammonia oxidizing bacteria to an environment that may promote growth. The growth state may be a state, e.g., ammonia oxidizing bacteria in an environment that allows immediate availability of ammonia oxidizing bacteria to convert ammonium ions ($NH_4^+$) to nitrite ($NO_2^-$). The growth state may comprise providing ammonia oxidizing bacteria in an environment having a pH of greater than about 7.6. The growth state may also comprise providing ammonia oxidizing bacteria in an environment having ammonia, ammonium ions, and/or urea, trace minerals and sufficient oxygen and carbon dioxide, as described in Section 1.

In some embodiments, the preparation of ammonia oxidizing bacteria may be in a polyphosphate loading state, wherein the state or the environment, e.g., a media, e.g., a culture media, e.g., a growth media, may have a pH of less than about 7.4. Levels of at least one of ammonia, ammonium ions, and urea may be between about 10 micromolar and 200 millimolar. Levels of trace materials may be between 0.1 micromolar iron and 20 micromolar iron. Levels of oxygen may be between about 5% and 100% oxygen saturation. Levels of carbon dioxide may be between/less than about zero and 200 ppm, and phosphate levels greater than about 10 micromolar. The purpose of the polyphosphate loading state is to provide AOB with ammonia and oxygen such that ATP can be produced, but to deny them carbon dioxide and carbonate such that they are unable to use that ATP to fix carbon dioxide and instead use that ATP to generate polyphosphate which may be stored.

In some embodiments, the preparation of ammonia oxidizing bacteria may be in a storage state. A storage state may be defined as ammonia oxidizing bacteria in an environment in which they may be stored to be later revived. The storage state may be a state, e.g., ammonia oxidizing bacteria in an environment that allows availability of ammonia oxidizing bacteria after being revived, e.g., after being place in an environment promoting a growth state for a pre-determined period of time. The pre-determined period of time for revival may be less than 72 hours. For example, the pre-determined period of time may be less than about 75 hours, or less than about 72 hours. The pre-determined period of time may at least partially based on a period time of about 0.2-10 times, 0.3-5 times, 0.5-3 times, 0.5-1.5 times, or 0.5 to 1 times the doubling time for the ammonia oxidizing bacteria. The pre-determined period of time may be at least partially based on a period of time of about one doubling time for the ammonia oxidizing bacteria. The pre-determined period of time may be between about 8 hours and 12 hours. The pre-determined period of time may be about 10 hours. The pre-determined time may be less than about 75 hours, 72 hours, 70 hours, 68 hours, 65 hours, 60 hours, 55 hours, 50 hours, 45 hours, 40 hours, 35 hours, 30 hours, 25 hours, 20 hours, 15 hours, 10 hours, 5 hours, 4 hours, 3, hours, 2 hours, or 1 hour. The pre-determined period of time may be between about 5 minutes and 5 hours. The pre-determined period of time may be about 5-10 minutes, 10-15 minutes, 15-20 minutes, 20-25 minutes, 25-30 minutes, 30-45 minutes, 45-60 minutes, 60 minutes-1.5 hours, 1.5 hours-2 hours, 2 hours-2.5 hours, 2.5 hours-3 hours, 3 hours-3.5 hours, 3.5 hours-4 hours, 4 hours-4.5 hours, 4.5 hours-5 hours. In some embodiments, the pre-determined period of time may be about 2 hours.

The storage state may comprise providing ammonia oxidizing bacteria in an environment having a pH of less than about 7.4. The storage state may also comprise providing ammonia oxidizing bacteria in an environment having ammonia, ammonia ions, and/or urea, trace minerals, oxygen, and low concentrations of carbon dioxide, as described in Section 1.

Storage may also be accomplished by storing at 4° C. for up to several months. The storage buffer in some embodiments may comprise 50 mM $Na_2HPO_4$-2 mM $MgCl_2$ (pH 7.6).

In some embodiments, ammonia oxidizing bacteria may be cyropreserved. A 1.25 ml of ammonia oxidizing bacteria mid-log culture may be added to a 2 ml cryotube and 0.75 ml of sterile 80% glycerol. Tubes may be shaken gently, and incubate at room temperature for 15 min to enable uptake of the cryoprotective agents by the cells. The tubes may be directly stored in a −80° C. freezer for freezing and storage.

For resuscitation of cultures, frozen stocks may be thawed on ice for 10-20 minutes, and then centrifuged at 8,000×g for 3 minutes at 4° C. The pellet may be washed by suspending it in 2 ml AOB medium followed by another centrifugation at 8,000×g for 3 minutes at 4° C. to reduce potential toxicity of the cryoprotective agents. The pellet may be resuspended in 2 ml of AOB medium, inoculated into 50 ml of AOB medium containing 50 mM $NH_4^+$, and incubated in dark at 30° C. by shaking at 200 rpm.

In some embodiments, the preparation of ammonia oxidizing bacteria may comprise ammonia oxidizing bacteria in a storage state and/or ammonia oxidizing bacteria in a polyphosphate loading state, and/or ammonia oxidizing bacteria in a growth state.

In some embodiments, upon actuation of the container, delivery system or device, ammonia oxidizing bacteria in a storage state or a polyphosphate loading state may be mixed with an activator. The activator may be in a form to provide a pH of at least about 7.6. The activator may be in a form to provide an environment having ammonia, ammonium ions, and/or urea, trace minerals and sufficient oxygen and carbon dioxide. The activator may revive or at least partially revive the ammonia oxidizing bacteria in a storage state or a polyphosphate loading state to a growth state. The time that it takes to revive the ammonia oxidizing bacteria from a storage state (or a polyphosphate loading state) may be a pre-determined period of time. For example, the pre-determined period of time may be less than about 75 hours, or less than about 72 hours. The pre-determined period of time may at least partially based on a period time of about 0.2-10 times, 0.3-5 times, 0.5-3 times, 0.5-1.5 times, or 0.5 to 1 times the doubling time for the ammonia oxidizing bacteria. The pre-determined period of time may be at least partially based on a period of time of about one doubling time for the ammonia oxidizing bacteria. The pre-determined period of time may be between about 8 hours and 12 hours. The pre-determined period of time may be about 10 hours. The pre-determined time may be less than about 75 hours, 72 hours, 70 hours, 68 hours, 65 hours, 60 hours, 55 hours, 50 hours, 45 hours, 40 hours, 35 hours, 30 hours, 25 hours, 20 hours, 15 hours, 10 hours, 5 hours, 4 hours, 3, hours, 2 hours, or 1 hour.

In some embodiments, the container may comprise ammonia oxidizing bacteria in a growth state, and in at least one of a storage state and a polyphosphate loading state, so as to provide ammonia oxidizing bacteria immediately to an environment to begin converting at least one of ammonia, ammonium ions, and urea to nitrite, while allowing for revival of the ammonia oxidizing bacteria in at least one of the storage state and the polyphosphate loading state over a period of time. This may allow for a controlled release of the stored ammonia oxidizing bacteria over a period of time.

Without wishing to be bound by theory, by maintaining ammonia oxidizing bacteria under conditions or in an environment of low carbon dioxide, with sufficient oxygen and ammonia, they may accumulate polyphosphate for a pre-determined period, e.g., for a period of about one doubling time, e.g., for about 8-12 hours, e.g., for about 10 hours. The ammonia oxidizing bacteria may accumulate sufficient polyphosphate to extend their storage viability, storage time, and accelerate their revival. This may occur with or without the addition of buffer and ammonia.

The presence of sufficient stored polyphosphate may allow the ammonia oxidizing bacteria the ATP resources to maintain metabolic activity even in the absence of ammonia and oxygen, and to survive insults that would otherwise be fatal.

The process of oxidation of ammonia to generate ATP has two steps. The first step is the oxidation of ammonia to hydroxylamine by ammonia monoxoygenase (Amo), followed by the conversion of hydroxylamine to nitrite by hydroxylamine oxidoreductase (Hao). Electrons from the second step (conversion of hydroxylamine to nitrite) are used to power the first step (oxidation of ammonia to hydroxylamine).

If an ammonia oxidizing bacteria does not have hydroxylamine to generate electrons for Amo, then hydroxylamine is not available for Hao. For example, acetylene irreversibly inhibits the enzyme crucial for the first step in the oxidation of ammonia to nitrite, the oxidation of ammonia to hydroxylamine. Once AOB are exposed to acetylene, Amo is irreversibly inhibited and new enzyme must be synthesized before hydroxylamine can be generated. In a normal consortium biofilm habitat, AOB may share and receive hydroxylamine form other AOB (even different strains with different susceptibilities to inhibitors) and so the biofilm tends to be more resistant to inhibitors such as acetylene than an individual organism. AOB can use stored polyphosphate to synthesize new Amo, even in the absence of hydroxylamine.

Any embodiment, preparation, composition, or formulation of ammonia oxidizing bacteria discussed herein may comprise, consist essentially of, or consist of optionally axenic ammonia oxidizing bacteria.

3. Methods of Producing Ammonia Oxidizing Bacteria

Methods of culturing various ammonia oxidizing bacteria, e.g., *Nitrosomonas* species are known in the art Ammonia oxidizing bacteria may be cultured, for example, using the media described in Table 1 or Table 2, above.

Ammonia oxidizing bacteria may be grown, for example, in a liquid culture or on plates. Suitable plates include 1.2% R2A agar, 1.2% agar, 1.2% agarose, and 1.2% agarose with 0.3 g/L pyruvate.

In some embodiments, ammonia oxidizing bacteria may be cultured in organic free media. One advantage of using organic free media is that it lacks substrate for heterotrophic bacteria to metabolize except for that produced by the autotrophic bacteria. Another advantage of using the as-grown culture is that substantial nitrite accumulates in the culture media, and this nitrite is also inhibitory of heterotrophic bacteria and so acts as a preservative during storage.

In some embodiments, an ammonia oxidizing bacteria with improved, e.g. optimized, properties is produced by an iterative process of propagation and selecting for desired properties. In some embodiments, the selection and propagation are carried out simultaneously. In some embodiments, the selection is carried out in a reaction medium (e.g., complete *N. europaea* medium) comprising 50 mM, 75 mM, 100 mM, 125 mM, 150 mM, 175 mM, 200 mM, 225 mM, 250 mM, 275 mM, or 300 mM $NH_4^+$, e.g., at least 200 mM NH$_4^+$. In some embodiments, the period of propagation and/or selection is at least 1, 2, 3, or 6 months. In embodiments, the period of propagation and/or selection is at least 1, 2, 4, 6, 8, or 10 years.

In some aspects, the ammonia oxidizing bacteria are manufactured on a commercial scale. In some embodiments, commercial scale refers to a liquid culturing method with a culture medium volume of at least 10,000, 20,000, 30,000, 50,000, or 100,000 liters (L). In some embodiments, the bacteria are produced in a bioreactor. The bioreactor may maintain the bacteria at a constant temperature, e.g., about 26-30 degrees Celsius using, for example a thermal jacket for insulation, a temperature sensor, and a heating or cooling element. The bioreactor may have an apparatus for stirring the culture to improve distribution of nutrients like ammonia, urea, oxygen, carbon dioxide, and various minerals. The bioreactor may also have an inlet tube for addition of new medium, and an outlet tube for collection of cells. The bioreactor may also have an aerator for distributing oxygen and/or carbon dioxide to the culture. The bioreactor may be, e.g., a batch reactor, a fed batch reactor, or a continuous reactor. In some embodiments, commercial scale production of ammonia oxidizing bacteria yields a batch of 1,000 to 100,000 L per day at about $10^{12}$ CFU/liter. The commercial scale production may yield e.g., a batch of 1,000-5,000, 5,000-10,000, 10,000-50,000, or 50,000-100,000 L/day. The commercial scale production may yield e.g., a batch of 1,000-5,000, 5,000-10,000, 10,000-50,000, or 50,000-100,000 L per batch. In some embodiments, the yield is at a concentration of at least $10^8$, $10^9$, $10^{10}$, $10^{11}$, $2\times10^{11}$, $5\times10^{11}$, or $10^{12}$, or about $10^{10}$-$10^{11}$, $10^{11}$-$10^{12}$, $10^{12}$-$10^{13}$, or $10^{13}$-$10^{14}$ CFU/L. In some embodiments, the yield is at a concentration of at least $10^8$, $10^9$, $10^{10}$, $10^{11}$, $2\times10^{11}$, $5\times10^{11}$, or $10^{12}$, or about $10^{10}$-$10^{11}$, $10^{11}$-$10^{12}$, $10^{12}$-$10^{13}$, or $10^{13}$-$10^{14}$ CFU/ml.

In some embodiments, typically including commercial scale production, quality control (QC) testing steps are carried out. The general steps of QC may comprise, 1) culturing ammonia oxidizing bacteria, 2) performing a testing step on the culture or an aliquot thereof, and 3) obtaining a value from the testing step, and optionally: 4) comparing the obtained value to a reference value or range of acceptable values, and 5) if the obtained value meets the acceptable reference value or range, then classifying the culture as acceptable, and if the obtained value does not meet the acceptable reference value or range, then classifying the culture as unacceptable. If the culture is classified as acceptable, the culture may, e.g., be allowed to continue growing and/or may be harvested and added to a commercial product. If the culture is classified as unacceptable, the culture may, e.g., be safely disposed of or the defect may be remedied.

The testing step may comprise measuring the optical density (OD) of the culture. OD is measured in a spectrophotometer, and provides information on the amount of light transmitted through the sample as distinguished from light absorbed or scattered. In some embodiments, the OD600 (e.g., optical density of light with a wavelength of 600 nm) may be determined. This measurement typically indicates the concentration of cells in the medium, where a higher optical density corresponds to a higher cell density.

The testing step may comprise measuring the pH of the culture. The pH of an ammonia oxidizing bacteria culture indicates the rate of nitrogen oxidation, and can also indicate whether the culture comprises a contaminating organism. pH may be measured using, e.g., a pH-sensing device comprising a electrode (such as a hydrogen electrode, quinhydron-Electrode, antimony electrode, glass electrode), a pH-sensing device comprising a semiconductor, or a color indicator reagent such as pH paper.

In certain embodiments, producing the ammonia oxidizing bacteria comprises carrying out various quality control steps. For instance, one may test the medium in which the ammonia oxidizing bacteria is grown, e.g., to determine whether it has an appropriate pH, whether it has a sufficiently low level of waste products, and/or whether it has a sufficiently high level of nutrients. One may also test for the presence of contaminating organisms. A contaminating organism is typically an organism other than ammonia oxidizing bacteria, for instance an organism selected from *Microbacterium* sp., *Alcaligenaceae* bacterium, *Caulobacter* sp., *Burkodelia multivorans*, *Escherichia coli*, *Klebsiella pneumoniae*, and *Staphylococcus aureus*. One may test for contaminants by, e.g., extracting DNA, amplifying it, and sequencing a conserved gene such as 16S rRNA. One may also test for contaminants by plating culture on agar plates and observing colony morphology. Ammonia oxidizing bacteria typically forms red colonies, so non-red colonies are often indicative of contaminating organisms.

4. Containers and Delivery Devices

Containers and/or delivery devices, e.g., containers, e.g., delivery devices, are provided as a housing for ammonia oxidizing bacteria, e.g., a preparation of ammonia oxidizing bacteria, e.g., a composition comprising ammonia oxidizing bacteria. In some embodiments, the container, or delivery device may also serve the purpose of delivering ammonia oxidizing bacteria, e.g., a preparation of ammonia oxidizing bacteria, e.g., a composition comprising ammonia oxidizing bacteria. The ammonia oxidizing bacteria may be from a genus selected from the group consisting of *Nitrosomonas*, *Nitrosococcus*, *Nitrosospira*, *Nitrosocystis*, *Nitrosolobus*, *Nitrosovibrio*, and combinations thereof. The container and/or delivery device may be configured to store and/or deliver ammonia oxidizing bacteria. The ammonia oxidizing bacteria, preparation, or composition, may be delivered to a site, and environment, or a surface, with or without additional components. In certain embodiments, other components may be delivered simultaneously or consecutively, e.g., at least partially before or at least partially after, the delivery of ammonia oxidizing bacteria commences. In certain embodiments, the container or delivery device may comprise or be referred to as a delivery system. In some embodiments, the delivery of one component is still occurring when the delivery of the second begins, so that there is overlap. This is sometimes referred to herein as "simultaneous" or "concomitant" or "concurrent delivery". In other embodiments, the delivery of one component ends before the delivery of the other treatment begins. This is sometimes referred to herein as "successive" or "sequential delivery" or "consecutive delivery."

In some embodiments, a container is provided. The container may comprise a first chamber, and a second chamber. Ammonia oxidizing bacteria, e.g., a preparation of ammonia oxidizing bacteria, e.g., a composition comprising ammonia oxidizing bacteria may be disposed in the first chamber. The ammonia oxidizing bacteria, e.g., a preparation of ammonia oxidizing bacteria, e.g., a composition comprising ammonia oxidizing bacteria may comprise at least one of ammonia oxidizing bacteria in a growth state, ammonia oxidizing bacteria in a storage state, and ammonia oxidizing bacteria in a polyphosphate loading state. One or more other components may be disposed in the second chamber. For example, an activator may be disposed in the second chamber. The activator may comprise one or more components that may provide, upon contact with ammonia oxidizing bacteria in the first chamber, ammonia oxidizing bacteria in a growth state.

Additional chambers are contemplated by this disclosure, in which one or more additional chambers comprise the same or different components or contents discussed throughout this disclosure. For example, the container may comprise a third chamber. The third chamber may comprise a diluting solution. The diluting solution may provide for diluting at least one of the contents of the first chamber, e.g., ammonia oxidizing bacteria, and the contents of the second chamber, e.g., an activator.

One or more of the chambers of the container, e.g., the first chamber and/or the second chamber may comprise a controlled release material, e.g., slow release material, which may be provided as part of the activator and/or the ammonia oxidizing bacteria preparation, or may be provided separately in one or more of the chambers. The material may to provide a controlled release, e.g., slow release, of, e.g., ammonia oxidizing bacteria, e.g., the at least one of ammonia, ammonium ions, and urea to the environment. In some embodiments, the material may provide a controlled release, e.g., slow release, of at least one of ammonia, ammonium ions, and urea to the environment to the preparation of ammonia oxidizing bacteria. This may occur within the container, at a delivery site, or upon delivery.

A barrier may be provided as part of or within the container to prevent fluid communication between the first chamber and the second chamber. The bather may be in the form of a valve, e.g., check valve, filtering material, film, wax, lipid, polymer, control release material, e.g., a gel, and other materials that may either provide a permanent or temporary barrier between the first chamber and the second chamber.

In some embodiments, one of the first chamber and the second chamber may be disposed within the other, e.g., a first chamber of the container may be disposed in the second chamber, e.g., a second chamber of the container may be disposed in the first chamber. In some embodiments, a plurality of first chambers may be disposed in the second chamber, or a plurality of second chambers may be disposed in the first chamber. Upon actuation of the container, the barrier may be disrupted to allow contact of the contents of the first chamber with the contents of the second chamber.

In some embodiments, the second chamber is disposed within a compartment, and the compartment is disposed within the first chamber. In other embodiments, the first chamber is disposed within a compartment, and the compartment is disposed with the first chamber. The compartment may be a bead, carrier, or other encapsulation system. One or both of the ammonia oxidizing bacteria or activator may be in this form. The encapsulation system may comprise a material that may provide for a controlled release of a component as described herein.

The container may also comprise an activator that may comprise a buffer solution and/or media. The buffer solution and/or media may provide conditions that may provide for activated ammonia oxidizing bacteria (e.g., ammonia oxidizing bacteria in a growth state) upon contact with ammonia oxidizing bacteria.

In some embodiments, the activator may comprise at least one of ammonia, ammonium ions, and urea. In certain embodiments, the activator may comprise, consist essentially of, or consist of ammonia. In certain other embodiments, the activator may comprise, consist essentially of, or consist of ammonium ions. In certain other embodiments, the activator may comprise, consist essentially of, or consist of urea.

Upon actuation of the container, a preparation of ammonia oxidizing bacteria and the activator may come into contact with one another. For example, if the container is actuated to deliver the contents of the first chamber and the second chamber, the contents, upon being expelled from the container, may come into contact with one another. Coming into contact with one another may involve or comprise at least some mixing. In some embodiments, the barrier of the container may remain intact throughout actuation. In other embodiments, the barrier may be opened, e.g., ruptured, torn, broken, ripped, or pierced, upon actuation.

The container may comprise a delivery system. The delivery system may be an applicator or be configured to deliver the contents of the first chamber and the second chamber. The delivery system may be an applicator or be configured to deliver the contents of the first chamber and the second chamber simultaneously or consecutively.

The delivery system may be configured to deliver a preparation of ammonia oxidizing bacteria to a skin surface of a subject, a nasal passage or the pulmonary region of a subject, or to the gastrointestinal tract of the subject. The preparation may be in the form of a particle, or a plurality of particles having a particle size to enhance delivery or enhance positioning or contact with a desired target site (e.g., skin, nasal passage, lungs, gastrointestinal system). The preparation may be in the form of a liquid, solid, in a suspension or in a solution.

In certain embodiments, the delivery system may comprise a pump to deliver the contents of the chamber from the container to a target site, e.g., an environment, e.g., a surface of a subject, e.g., skin of a subject, gastrointestinal tract, pulmonary region, or nasal passages.

In some embodiments, the container may be a single-use container. The container may or may not be pre-loaded (e.g., loaded by a manufacturer or user) with contents, e.g., ammonia oxidizing bacteria, and ammonia, ammonium ions and urea, and may be used once by a user, e.g., a consumer or medical professional to deliver the contents of the container to a target site, e.g., an environment, e.g., a surface of a subject, e.g., skin of a subject, gastrointestinal tract, pulmonary region, or nasal passages.

In other embodiments, the container may be a multiple-use container in which the container may or may not be pre-loaded (e.g., loaded by a manufacturer or user) with contents, e.g., ammonia oxidizing bacteria, and ammonia, ammonium ions and urea, and may be used once by a user, e.g., a consumer or medical professional to deliver the contents of the container to a target site, e.g., an environment, e.g., a surface of a subject, e.g., skin of a subject, gastrointestinal tract, pulmonary region, or nasal passages. The container may be re-loaded (e.g., loaded by a manufacturer or user) with contents e.g., ammonia oxidizing bacteria, and ammonia, ammonium ions and urea, and may be used again by a same or different user, e.g., a consumer or medical professional to deliver the contents of the container to a target site, e.g., an environment, e.g., a surface of a subject, e.g., skin of a subject, gastrointestinal tract, pulmonary region, or nasal passages.

In some embodiments, the container may be in the form of a two-compartment syringe in which the contents may be dispensed by one or more plungers that may deliver contents from the container simultaneously or consecutively. The tip area of the syringe may comprise two compartment, e.g., chambers, to deliver the contents separately to a target site, e.g., an environment, e.g., a surface of a subject, e.g., skin of a subject, gastrointestinal tract, pulmonary region, or nasal passages, or may comprise one compartment, e.g., chamber, e.g., mixing chamber, that allows for mixing of the contents of the container prior to delivery to the target site.

In some embodiments, the container may comprise a two-compartment bottle. The two-compartment bottle may comprise two separate openings to deliver the contents of the container separately to a target site, e.g., an environment, e.g., a surface of a subject, e.g., skin of a subject, gastrointestinal tract, pulmonary region, or nasal passages, or may comprise an additional compartment, e.g., chamber, e.g., mixing chamber that allows for mixing of the contents of the container prior to delivery to the target site.

In some embodiments, a two-compartment ampule may be provided. The two-compartment ampule may comprise a first chamber and a second chamber having the contents described herein throughout the disclosure. The ampule may have an etched region on each of its compartments to provide for ease in opening the ampules for delivery to a target site.

In some embodiments the container is the form of an applicator, e.g., a deodorant application. This configuration may allow for a first chamber and a second chamber to be provided within the application, and a dial region to transfer contents from the chamber to an applicator region, in order to deliver the contents of the container to a target site. The contents of the container may be delivered separately, may be mixed within the container, or may be mixed in the applicator region.

A mixing chamber may be provided in one or more embodiments of the present disclosure. The mixing chamber may be provided to allow for mixing of contents of the container prior to delivery of the contents to a target site. Upon actuation of the delivery device, ammonia oxidizing bacteria and the activator may contact each other. In some embodiments, upon actuation of the delivery device, ammonia oxidizing bacteria may mix with one another.

In some embodiments, the container may be substantially free of other organisms.

The container may be disposed in a powder, cosmetic, cream, stick, aerosol, salve, wipe, or bandage. The container may be provided as a powder, cosmetic, cream, stick, aerosol, salve, wipe, or bandage.

In some embodiments, the container may comprise a mixing indicator component. The mixing indicator component may be provided in at least one of the first chamber, the second chamber, and a mixing chamber. The mixing indicator component may be present as part of the preparation of ammonia oxidizing bacteria, the activator, or both. The mixing indicator component may comprise a color marker that may develop a color upon contact of contents of the container or mixing of contents of the container.

In some embodiments, the container may comprise an activation indicator component. The activation indicator component may be provided in at least one of the first chamber, the second chamber, and a mixing chamber. The activation indicator component may be present as part of the preparation of ammonia oxidizing bacteria, the activator, or both. The mixing indicator component may comprise a color marker that may develop a color upon contact of contents of the container or mixing of contents of the container.

Crushing of the container may create contact of components of the container which may provide for an indicator of mixing through a color change of the contents of the container. Contact between the components of the container may be provided by rolling or rubbing the container, e.g., the applicator, e.g., the applicator region on a target area, e.g., a skin surface. Force, pressure, or friction may be applied between the container and the target area to induce contact of components within the container.

In some embodiments, a first color marker may be positioned in the first chamber, and the second color marker may be positioned in the second chamber. Upon mixing, or upon activation, a third color may be generated to indicate mixing or activation.

In some embodiments, the container may be configured to deliver the preparation of ammonia oxidizing bacteria from the first chamber to a surface prior to the activator of the second chamber. In other embodiments, the container may be configured to deliver the activator of the second chamber to a surface prior to the preparation of ammonia oxidizing bacteria from the first chamber. In yet other embodiments, the container may be configured to deliver the preparation of ammonia oxidizing bacteria from the first chamber and the activator of the second chamber substantially simultaneously.

The container may be constructed of any material suitable for housing the contents, e.g., ammonia oxidizing bacteria, e.g., an activator, e.g., ammonia, ammonium ions, and urea. For example the container may be constructed and arranged to be at least partially resistant to at least one of gaseous exchange, water, and light. For example, the container may be constructed of a glass or polymeric material.

In some embodiments, one or more other organisms besides ammonia oxidizing bacteria may be included in the container, e.g., in or as part of one or more of a first chamber, the second chamber, the preparation of ammonia oxidizing bacteria, and the activator. For example, an organism of the genus selected from the group consisting of *Lactobacillus, Streptococcus, Bifidobacter*, and combinations thereof, may be provided in a first chamber, a second chamber, or other chamber, the preparation of ammonia oxidizing bacteria, and the activator.

The containers described herein may be adapted to deliver one or more cosmetic products. The containers described herein may be adapted to deliver one or more therapeutic products.

The weight of the container, delivery system, or delivery device, including or not including the contents of the container may be less than about 50, 100, 200, 300, 400, 500, 600, 700, 800, 900, 1000, 1500, or 2000 grams.

In some embodiments, the container may comprise a first chamber and a second chamber, which are configured such that the barrier is not fixed relative to the first chamber and the second chamber. In some embodiments, the barrier may be fixed relative to the first chamber, but not relative to the second chamber. In other embodiments, the barrier may be fixed relative to the second chamber, but not relative to the first chamber.

In some embodiments, the first chamber and the second chamber may be configured such that the barrier is at least partially common to the first chamber and the second chamber. In other embodiments the barrier is not common to the first chamber and the second chamber.

In some embodiments the first chamber may comprise a housing and a first lumen, and the second chamber may comprise a housing and a second lumen. The first housing and the second housing may be fixed relative to each other. In some embodiments, a portion of the first housing and the second housing may be shared by the first chamber and the second chamber. The portion may comprise a barrier. In some embodiments, the first housing and the second housing are independent from one another, e.g., they may move independently from one another.

Embodiments of the disclosure are shown in FIGS. 1-8. Containers, e.g., delivery devices or systems are shown. As shown in FIG. 1, container 10 is provided. Container 10 comprises a first chamber 110 and a second chamber 120. Ammonia oxidizing bacteria may be disposed in first chamber 110, while an activator may be disposed in the second chamber 120. In some embodiments, activator may be disposed in first chamber 110, while autotrophic bacteria, e.g., ammonia oxidizing bacteria may be disposed in second chamber 120. Barrier 130 is provided to separate first chamber 110 and second chamber 120. Barrier 130 is provided to prevent fluid communication between first chamber 110 and second chamber 120. Container 10 further comprises opening 140 and opening 150. Opening 140 allows contents of first chamber 110, e.g., autotrophic bacteria, e.g., ammonia oxidizing bacteria, to be released from first chamber 110. Opening 150 allows contents of second chamber 120, e.g., an activator, to be released from second chamber 120. Plunger 160 allows for contents of first chamber 110 and second chamber 120 to be pushed through each of the chambers to be released through opening 140 and opening 150. Opening 140 and opening 150 may each have a cover to contain the contents of the container, or may jointly share a cover to contain the contents in the container. In the embodiment of FIG. 1, the contents of container 10 may be dispensed individually from container 10, and are applied to a surface or an environment simultaneously or substantially simultaneously. In this embodiment, barrier 130 is fixed relative to chamber 110 and chamber 120.

Figure 2:
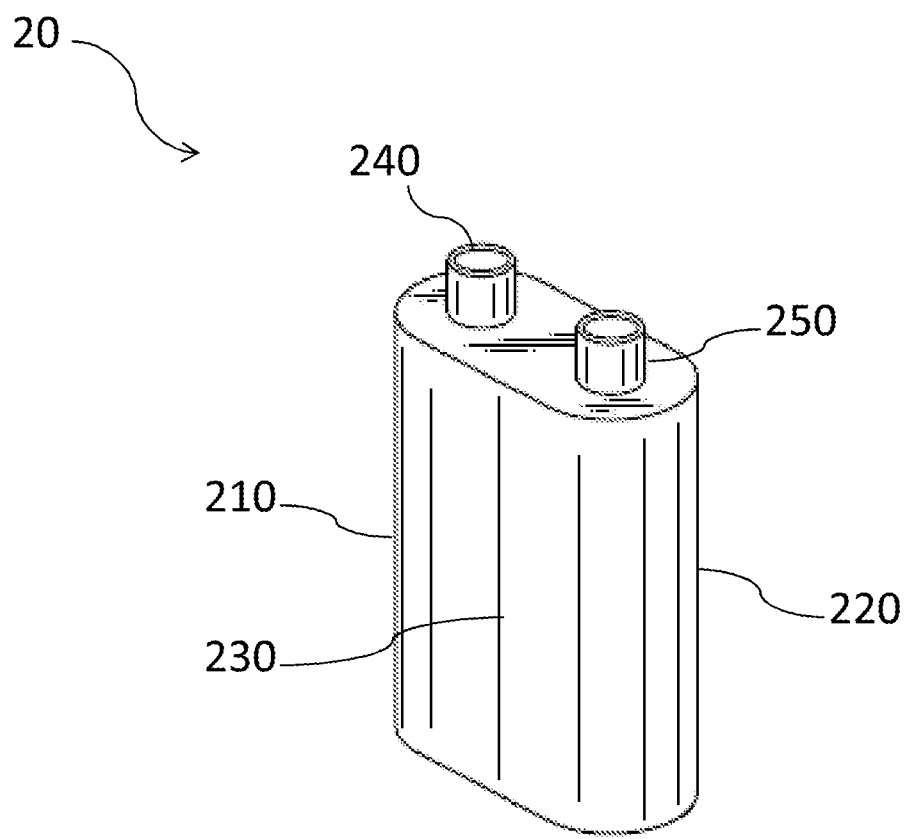
FIG. 2 shows a perspective view of a container in accordance with some embodiments of the disclosure.

As shown in FIG. 2, container 20 is provided. Container 20 comprises first chamber 210 and second chamber 220. Autotrophic bacteria, e.g., ammonia oxidizing bacteria may be disposed in first chamber 210, while an activator may be disposed in second chamber 220. In some embodiments, activator may be disposed in first chamber 210, while autotrophic bacteria, e.g., ammonia oxidizing bacteria may be disposed in second chamber 220. Barrier 230 is provided to separate first chamber 210 and second chamber 220. Barrier 230 is provided to prevent fluid communication between first chamber 210 and second chamber 220. Container 20 further comprises opening 240 and opening 250. Opening 240 allows contents of first chamber 210, e.g., autotrophic bacteria, e.g., ammonia oxidizing bacteria, to be released from first chamber 210. Opening 250 allows contents of second chamber 220, e.g., an activator, to be released from second chamber 220. Opening 240 and opening 250 may each have a cover to contain the contents of the container, or may jointly share a cover to contain the contents in the container. In the embodiment of FIG. 2, the contents of container 20 may be dispensed individually from container 20, and are applied to a surface or an environment simultaneously or substantially simultaneously. Alternatively, the contents of container 20 may be dispensed individually from container 20 consecutively, e.g., the contents of first chamber 210 may be applied to a surface or an environment prior to second chamber 220, or the contents of second chamber 220 may be applied to a surface or an environment prior to first chamber 210. In this embodiment, barrier 230 is fixed relative to chamber 210 and chamber 220.

Figure 3:
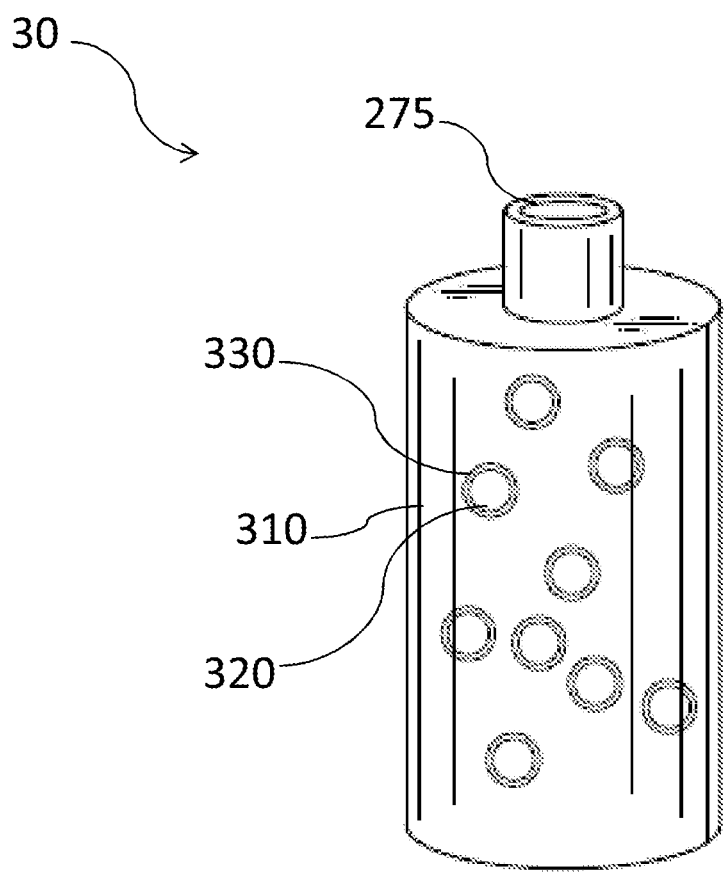
FIG. 3 shows a perspective view of a container in accordance with some embodiments of the disclosure.

As shown in FIG. 3, container 30 is provided. Container 30 comprises first chamber 310 and second chamber 320. Autotrophic bacteria, e.g., ammonia oxidizing bacteria may be disposed in first chamber 310, while an activator may be disposed in second chamber 320. In some embodiments, activator may be disposed in first chamber 310, while autotrophic bacteria, e.g., ammonia oxidizing bacteria may be disposed in second chamber 320. Chamber 320 is disposed within chamber 310. Barrier 330 is provided to separate first chamber 310 and second chamber 320. Barrier 330 is provided to prevent fluid communication between first chamber 310 and second chamber 320. Container 30 further comprises opening 275 to allow contents of first chamber 310, e.g., autotrophic bacteria, e.g., ammonia oxidizing bacteria, to be released, and contents of second chamber 320, e.g., an activator, to be released. In the embodiment of FIG. 3, the contents of container 30 may be delivered with barrier 330 intact. They may then be applied to a surface or an environment with the barrier intact. Alternatively, delivering the contents of container may disrupt or brake barrier 330 so that the contents of the container are mixed and applied to a surface or an environment.

Figure 4:
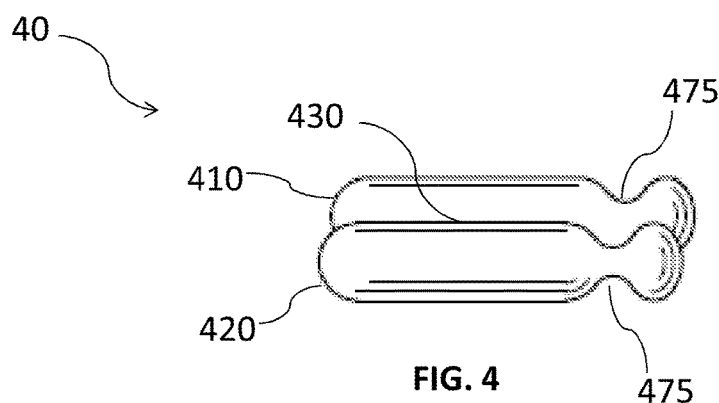
FIG. 4 shows a perspective view of a container in accordance with some embodiments of the disclosure.

As shown in FIG. 4, container 40 is provided. Container 40 comprises first chamber 410 and second chamber 420. Autotrophic bacteria, e.g., ammonia oxidizing bacteria may be disposed in first chamber 410, while an activator may be disposed in second chamber 420. In some embodiments, activator may be disposed in first chamber 410, while autotrophic bacteria, e.g., ammonia oxidizing bacteria may be disposed in second chamber 420. Barrier 430 is provided to separate first chamber 410 and second chamber 420. Barrier 430 is provided to prevent fluid communication between first chamber 410 and second chamber 420. Container 40 is typically a two-chamber ampule, which necessitates breakage in neck area 475 in order to open. The contents of container 40 may be dispensed individually from container 40, and are applied to a surface or an environment simultaneously or substantially simultaneously. Alternatively, the contents of container 40 may be dispensed individually from container 40 consecutively, e.g., the contents of first chamber 410 may be applied to a surface or an environment prior to second chamber 420, or the contents of second chamber 420 may be applied to a surface or an environment prior to first chamber 410. This may be accomplished by breaking first chamber 410 prior to second chamber 420, or second chamber 420 prior to first chamber 410. In this embodiment, barrier 430 is fixed relative to chamber 410 and chamber 420.

Figure 5:
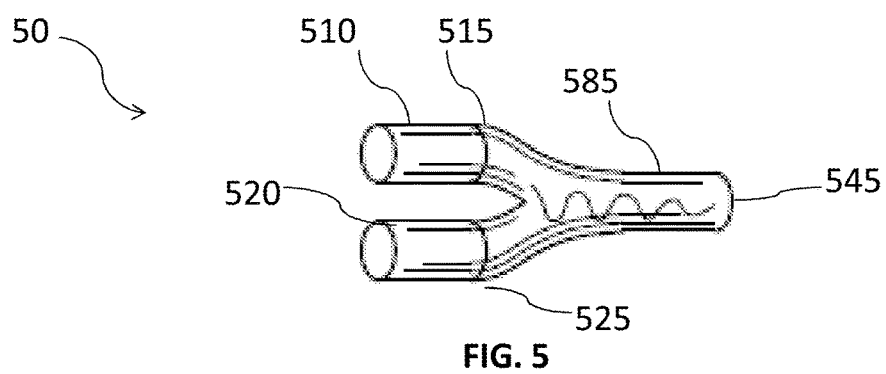
FIG. 5 shows a perspective view of a container in accordance with some embodiments of the disclosure.

As shown in FIG. 5, container 50 is provided. Container 50 comprises first chamber 510 and second chamber 520. Autotrophic bacteria, e.g., ammonia oxidizing bacteria may be disposed in first chamber 510, while an activator may be disposed in second chamber 520. In some embodiments, activator may be disposed in first chamber 510, while autotrophic bacteria, e.g., ammonia oxidizing bacteria may be disposed in second chamber 520. This Figure shows first chamber 510 and second chamber 520 as separate, i.e., not sharing a common barrier, however other embodiments can be foreseen in which first chamber 510 and second chamber 520 share a common barrier, at least partially. Container 50 further comprises first chamber barrier 515 and second chamber barrier 525 to prevent fluid communication between first chamber 510 and mixing chamber 585, and second chamber 520 and mixing chamber 585. Mixing chamber 585 allows contents of first chamber 510 and second chamber 520 to come into contact with each other, e.g., mix with each other, prior to exiting container 50 through opening 545. Prior to breaking barrier 515 and barrier 525, mixing chamber may be empty or contain other components as discussed throughout the disclosure. The contents of container 50 are dispensed from mixing chamber 585 to a surface or an environment.

Figure 6:
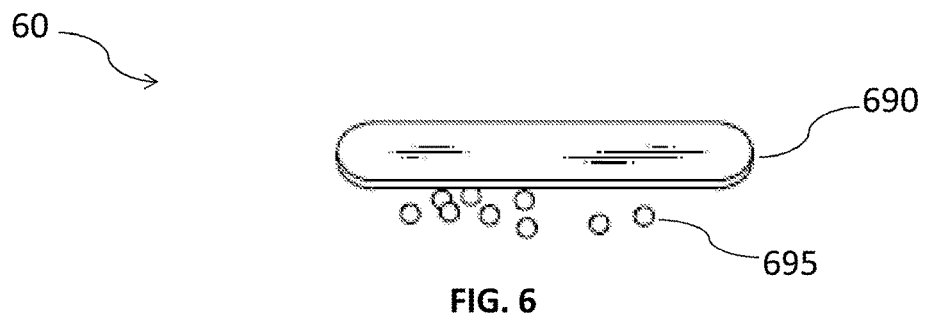
FIG. 6 shows a perspective view of a container in accordance with some embodiments of the disclosure.

As shown in FIG. 6, activator 690 may be provided as a layer that may be placed near or applied on top of, or surrounding autotrophic bacteria, e.g., ammonia oxidizing bacteria, 695. Activator 690 may be prepared in a controlled release formulation that may allow removal or exposure of activator 690 over a pre-determined period of time. This would allow it to come into contact with autotrophic bacteria, e.g., ammonia oxidizing bacteria, as needed or over a pre-determined time period.

Figure 7:
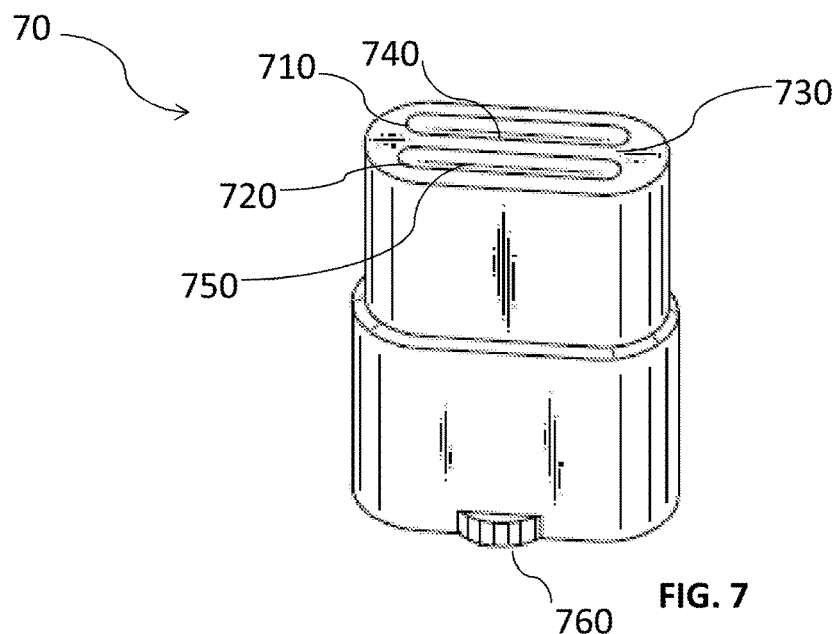
FIG. 7 shows a perspective view of a container in accordance with some embodiments of the disclosure.
Figure 8:
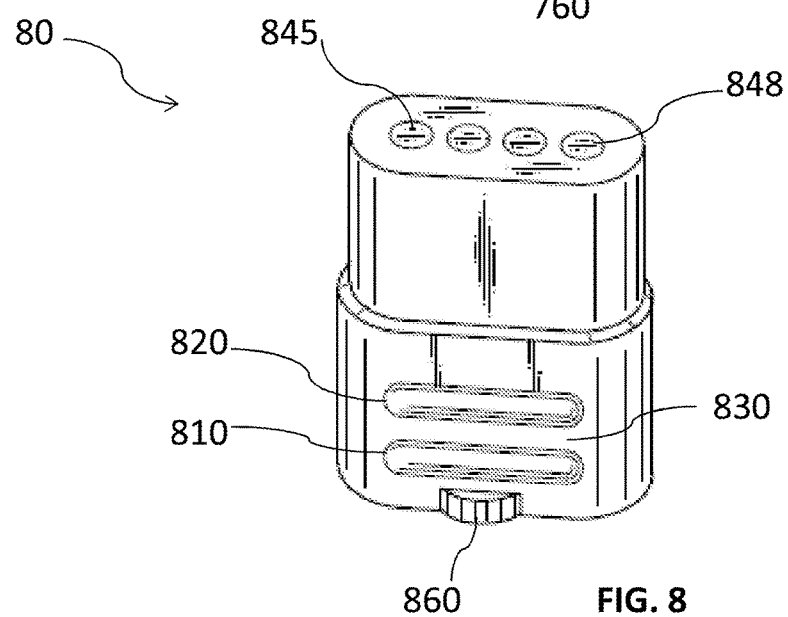
FIG. 8 shows a perspective view of a container in accordance with some embodiments of the disclosure.

As shown in FIGS. 7 and 8, container, e.g., applicator, 70 and 80 are provided, respectively. In FIG. 7, container 70 comprises first chamber 710 and second chamber 720. Autotrophic bacteria, e.g., ammonia oxidizing bacteria may be disposed in first chamber 710, while an activator may be disposed in second chamber 720. In some embodiments, activator may be disposed in first chamber 710, while autotrophic bacteria, e.g., ammonia oxidizing bacteria may be disposed in second chamber 720. Barrier 730 is provided to separate first chamber 710 and second chamber 720. Barrier 730 is provided to prevent fluid communication between first chamber 710 and second chamber 720. Container 70 further comprises opening 740 and opening 750. Opening 740 allows contents of first chamber 710, e.g., autotrophic bacteria, e.g., ammonia oxidizing bacteria, to be released from first chamber 710. Opening 750 allows contents of second chamber 720, e.g., an activator, to be released from second chamber 720. In the embodiment of FIG. 7, the contents of container 70 may be dispensed individually from container 70, and are applied to a surface or an environment simultaneously or substantially simultaneously. Alternatively, the contents of container 70 may be dispensed individually from container 70 consecutively, e.g., the contents of first chamber 710 may be applied to a surface or an environment prior to second chamber 720, or the contents of second chamber 720 may be applied to a surface or an environment prior to first chamber 710. In this embodiment, barrier 730 is fixed relative to chamber 710 and chamber 720. Dial 760 allows for contents of first chamber 710 and second chamber 720 to be pushed through each of the chambers to be released through opening 740 and opening 750. Container 70 may comprise one dial to push contents of the chamber simultaneously or substantially simultaneously, or more than one dial to push contents of the chamber consecutively.

In FIG. 8, container 80 comprises first chamber 810 and second chamber 820. Autotrophic bacteria, e.g., ammonia oxidizing bacteria may be disposed in first chamber 810, while an activator may be disposed in second chamber 820. In some embodiments, activator may be disposed in first chamber 810, while autotrophic bacteria, e.g., ammonia oxidizing bacteria may be disposed in second chamber 820. Barrier 830 is provided to separate first chamber 810 and second chamber 820. Barrier 830 is provided to prevent fluid communication between first chamber 810 and second chamber 820. Container 80 further comprises opening 845. Opening 845 allows contents of first chamber 810 and contents of second chamber 820 to be released from container 80. In the embodiment of FIG. 8, the contents of container 80 may come into contact with one another when breaking barrier 830. This may occur upon actuation of dial 860 to push components through the chambers to be released through opening 845. This would provide for contact of components within container 80. In another embodiment contents may come into contact with one another after being released through the openings, e.g., if opening 845 was available to deliver contents from first chamber 810, and opening 848 was available to deliver contents from second chamber 820.

5. Kits

Kits may be provided by the present disclosure. The kits may comprise containers and/or delivery devices. The containers, e.g., delivery devices are provided as a housing for ammonia oxidizing bacteria, e.g., a preparation of ammonia oxidizing bacteria, e.g., a composition comprising ammonia oxidizing bacteria. In some embodiments, the container, or delivery device may also serve the purpose of delivering ammonia oxidizing bacteria, e.g., a preparation of ammonia oxidizing bacteria, e.g., a composition comprising ammonia oxidizing bacteria. The ammonia oxidizing bacteria may be from a genus selected from the group consisting of *Nitrosomonas, Nitrosococcus, Nitrosospira, Nitrosocystis, Nitrosolobus, Nitrosovibrio*, and combinations thereof.

The kits may be provided with a container and/or delivery device which may be configured to store and/or deliver ammonia oxidizing bacteria. The ammonia oxidizing bacteria, preparation, or composition, may be delivered to a site, an environment, or a surface, with or without additional components. In certain embodiments, other components may be delivered simultaneously or consecutively with the delivery of ammonia oxidizing bacteria. In certain embodiments, the container or delivery device may comprise or be referred to as a delivery system.

The kits of the present disclosure may comprise a preparation of an ammonia oxidizing bacteria. The kit may also comprise an activator for activating the ammonia oxidizing bacteria. The kit may further comprise a delivery device for delivering at least one of the preparation of ammonia oxidizing bacteria and the activator to a subject. The kit may comprise a container as described throughout the disclosure. The delivery device of the kit may be the container as described throughout the disclosure.

In some embodiments, the kit may further comprise a wash solution or wipe provided to clean the surface to which the preparation of ammonia oxidizing bacteria is applied. The kit may also comprise a diluting solution to allow dilution of a component of the kit, e.g., at least one of the preparation of ammonia oxidizing bacteria and the activator.

In some embodiments, the kits may comprise assays to test various characteristics of one or more components of the container. For example, the kit may comprise an assay to determine a viability of the preparation of ammonia oxidizing bacteria.

Viability may include the ammonia oxidizing bacteria's ability to oxidize ammonia, ammonium, or urea to nitrite at a rate, e.g., a pre-determined rate. In some embodiments, the rate refers to the conversion of ammonium ions ($NH_4^+$) (e.g., at about 200 mM) to nitrite ($NO_2^-$) at a rate of at least 50, 75, 125, or 150 micromoles $NO_2^-$ per minute, e.g., about 100-150, 75-175, 75-125, 100-125, 125-150, or 125-175 micromoles/minute, e.g., about 125 micromoles $NO_2^-$ per minute.

The kit may comprise an assay to determine a characteristic of the surface to which the preparation of ammonia oxidizing bacteria is applied. The characteristic to be tested in the assay may comprise any one or more of a level of nitrite on the skin, a skin pH, or presence of Propionibacteria by 16S rRNA sequencing.

In some embodiments, the kit may be used to provide a cosmetic product. The kit may comprise a first cosmetic and a second cosmetic, wherein the first cosmetic comprises an ammonia oxidizing bacteria. In some embodiments, both the first cosmetic and the second cosmetic may comprise ammonia oxidizing bacteria. The cosmetic may be any cosmetic disclosed herein.

In some embodiments, the kit may be used to provide a therapeutic product. The kit may comprise a first therapeutic and a second therapeutic, wherein the first therapeutic comprises an ammonia oxidizing bacteria. In some embodiments, both the first therapeutic and the second therapeutic may comprise ammonia oxidizing bacteria. The therapeutic product may be any therapeutic product disclosed herein.

6. Methods of Delivering Ammonia Oxidizing Bacteria

In some embodiments, ammonia oxidizing bacteria, e.g., a preparation of ammonia oxidizing bacteria, e.g., a composition of ammonia oxidizing bacteria may be delivered to a subject. The method may comprise providing a preparation of ammonia oxidizing bacteria, and an activator. The method may further comprise combining the preparation of ammonia oxidizing bacteria and the activator. The preparation of ammonia oxidizing bacteria and the activator may be administered to the subject by way of a container, a delivery device, or a delivery system.

The combining, or mixing of the preparation of ammonia oxidizing bacteria and the activator may occur at the time of delivery, e.g., at a surface of the subject, or may occur prior to delivery at a surface of the subject.

In some embodiments, the preparation of ammonia oxidizing bacteria may be provided by providing a container, delivery device or delivery system as discussed herein. The preparation and the activator may be transferred, e.g., to a surface of a subject, to provide activated ammonia oxidizing bacteria, e.g., ammonia oxidizing bacteria in a growth state. In this process a barrier of the container, delivery device, or delivery system may be actuated. This actuation may comprise disrupting the barrier. This may allow the preparation and the activator to contact one another, or to mix with one another. The actuation may also, or in the alternative, allow deposition of the preparation and activator, simultaneously, or consecutively, to provide activated ammonia oxidizing bacteria on a surface of a subject, e.g., on a surface of a body. The surface of the body may be a portion of skin, such as a facial area, a lip, or an underarm. Other surfaces of the body may be contemplated by the present disclosure 7. Method of Preserving Ammonia Oxidizing Bacteria Methods of preserving ammonia oxidizing bacteria are provided by this disclosure. The methods may comprise providing a preparation of ammonia oxidizing bacteria. The methods may also comprise preserving a preparation of ammonia oxidizing bacteria. The methods of preserving or providing a preparation may provide for ammonia oxidizing bacteria in a polyphosphate loading state and/or a storage state.

In some embodiments, the methods may comprise culturing ammonia oxidizing bacteria in an environment having a pH of less than about 7.4. In addition, or in the alternative, the method may comprise culturing ammonia oxidizing bacteria under a carbon dioxide concentration sufficiently low, and an oxygen concentration and an amino acid concentration sufficiently high such that the ammonia oxidizing bacteria accumulate polyphosphate. This may provide the preparation of ammonia oxidizing bacteria, or preserving the preparation of ammonia oxidizing bacteria.

In some embodiments, culturing may comprise contacting a sample of ammonia oxidizing bacteria with a culture medium having a pH of about 7.4 or less. The culture medium may have a concentration of at least one of ammonia, ammonium ions, and urea of between about 10 micromolar and about 200 millimolar, in an environment having a carbon dioxide concentration of less than about 200 ppm, and an oxygen concentration of between about 5% to about 100% saturation.

In some embodiments, culturing may comprise contacting the sample of ammonia oxidizing bacteria with a culture medium having greater than 10 micromolar phosphate. In some embodiments, culturing comprises contacting the sample of ammonia oxidizing bacteria with a culture medium having between about 0.1 micromolar and 20 micromolar iron.

In some embodiments, contacting the sample may comprise contacting the sample for a pre-determined period of time. The pre-determined period of time may be the time period that allows sufficient polyphosphate accumulation in the ammonia oxidizing bacteria. This pre-determined period of time is the period of time suitable to provide for sufficient polyphosphate loading to allow for the ammonia oxidizing bacteria to be stored for an extended period of time. The pre-determined period of time may be at least partially based on a period of time of about 0.2-10 times, 0.3-5 times, 0.5-3 times, 0.5-1.5 times, or 0.5 to 1 times the doubling time for the ammonia oxidizing bacteria. The pre-determined period of time may be at least partially based on a period of time of about one doubling time for the ammonia oxidizing bacteria. In some embodiments, the pre-determined period of time is between about 8 hours and 12 hours. In some embodiments, the pre-determined period of time is about 10 hours. In some embodiments, the pre-determined period of time is about 24 hours.

In some embodiments, the sample of ammonia oxidizing bacteria to be contacted with the culture medium is in a growth state. This sample of ammonia oxidizing bacteria, through contact with the culture medium may be induced into a polyphosphate loading state.

In some embodiments, the method may comprise further contacting the sample of ammonia oxidizing bacteria with a culture medium having a pH of about 7.4 or less, a concentration of at least one of ammonia, ammonium ions, and urea of between about 10 micromolar and about 100 micromolar. The culture medium may also have an environment of a carbon dioxide concentration of less than about 400 ppm. The culture medium may further have an environment having an oxygen concentration of between about 0% to about 100% saturation. This may be provided as a "storage state." The method may comprise, after culturing in a polyphosphate loading state for a period of time, e.g., a pre-determined period of time, removing the media from the ammonia oxidizing bacteria. The method may further comprise resuspending the ammonia oxidizing bacteria in a buffer, e.g., to provide conditions of a "storage state." This may allow the ammonia oxidizing bacteria to remain in a "storage state" for a period of time, e.g., a pre-determined period of time, for example, at least 1, 2, 3, 4, 5, 6, 7, days, 1, 2, 3, 4 weeks, 1, 2, 3, 4, 5, 6, 7, 8, 9, 10, 11, 12 months, 1, 2, 3, 4, or 5 years. In some embodiments, the ammonia oxidizing bacteria may remain in a storage state for at least about 6 months to about 1 year. Upon revival, the viability of the ammonia oxidizing bacteria is at least about 50%, 60%, 70%, 80%, 90%, or 100% of the viability as of the ammonia oxidizing bacteria prior to storage e.g., in a growth state). In some embodiments, the preparation of ammonia oxidizing bacteria may be prepared, such that no more than 10%, 20%, 30%, 40%, 50%, 60%, or 70% of the ability to oxidize $NH_4^+$ is lost upon storage at selected conditions.

In some embodiments, the sample is contacted with the environment that may induce a storage state, e.g., a culture medium that may induce a storage state, e.g., a polyphosphate loading state, for a pre-determined period of time. The pre-determined period of time may at least partially based on a period time of about 0.2-10 times, 0.3-5 times, 0.5-3 times, 0.5-1.5 times, or 0.5 to 1 times the doubling time for the ammonia oxidizing bacteria. The pre-determined period of time is at least partially based on a period of time of about one doubling time for the ammonia oxidizing bacteria. The pre-determined period of time may be between about 8 hours and 12 hours. The pre-determined period of time may be about 10 hours. The pre-determined period of time may be about 24 hours, or less than about 24 hours.

In some embodiments, the sample, prior to contacting with the environment that may induce a storage state, is in a growth state.

In some embodiments, a method of reviving ammonia oxidizing bacteria from a storage state is provided. The method may comprise contacting a sample of ammonia oxidizing bacteria with an environment that may induce revival, e.g., induce a growth state. The method may comprise contacting the sample with an environment, e.g., a culture medium having a pH of greater than about 7.6. In addition or in the alternative, the method may comprise contacting the sample with an environment, e.g., a culture medium, having a concentration of at least one of ammonia, ammonium ions, and urea of between about 10 micromolar and 100 millimolar. Levels of trace materials are between about 0.1 micromolar iron and 20 micromolar iron. The method may comprise contacting the sample with an environment, e.g., a culture medium, in an environment having a carbon dioxide concentration of greater than about between about 5% and 100% oxygen saturation, and an oxygen concentration of between about 200 ppm and 5% saturation (e.g., of media).

In some embodiments, the sample is contacted with the environment that may induce a growth state, e.g., from a storage state, e.g., a culture medium that may induce a growth state, for a pre-determined period of time. The pre-determined period of time, e.g., the time it may take to achieve revival of the ammonia oxidizing bacteria, e.g., achieve viability of the ammonia oxidizing bacteria as compared to the viability of the bacteria prior to storage, e.g., at least about 10%, 20%, 30%, 40%, 50%, 60%, 70%, 80%, 90%, 95%, 97%, 98%, 99%, or 100% viability, may at least partially based on a period time of about 0.2-10 times, 0.3-5 times, 0.5-3 times, 0.5-1.5 times, or 0.5 to 1 times the doubling time for the ammonia oxidizing bacteria. The pre-determined period of time is at least partially based on a period of time of about one doubling time for the ammonia oxidizing bacteria. The pre-determined period of time may be between about 8 hours and 12 hours. The pre-determined period of time may be about 10 hours. The pre-determined time may be less than about 75 hours, 72 hours, 70 hours, 68 hours, 65 hours, 60 hours, 55 hours, 50 hours, 45 hours, 40 hours, 35 hours, 30 hours, 25 hours, 20 hours, 15 hours, 10 hours, 5 hours, 4 hours, 3, hours, 2 hours, or 1 hour.

In some embodiments, a preparation, e.g., a composition, comprising an ammonia oxidizing bacteria is provided by the methods discussed above. The preparation may be formulated such that no more than a specific percentage of the ammonia oxidizing bacteria to oxidize ammonia, ammonium ions, and urea is lost upon storage at selected conditions, e.g., conditions described herein. For example the preparation may be formulated such that no more than 10%, 20%, 30%, 40%, 50%, 60%, or 70% of the ability to oxidize $NH_4^+$ is lost upon storage at selected conditions. The preparations may be adapted for use as a product, e.g., a cosmetic product as discussed herein, or a therapeutic product, or for treatment in any one of the diseases or conditions discussed herein.

8. Compositions Comprising Ammonia Oxidizing Bacteria

The present disclosure provides, inter alfa, compositions comprising ammonia oxidizing bacteria, e.g., a preparation of ammonia oxidizing bacteria, or a purified preparation of ammonia oxidizing bacteria. The compositions comprising ammonia oxidizing bacteria, e.g., a preparation of ammonia oxidizing bacteria, or a purified preparation of ammonia oxidizing bacteria may be provided in a cosmetic product or a therapeutic product. The compositions may comprise natural products comprising ammonia oxidizing bacteria.

In some aspects, the present disclosure provides compositions, e.g., preparations, with a defined number of species. For instance, this disclosure provides a composition having ammonia oxidizing bacteria, or more specifically having one genus of ammonia oxidizing bacteria, or more specifically, having one species of ammonia oxidizing e.g., *N. eutropha*, and one other type of organism, and no other types of organism. In other examples, the composition has ammonia oxidizing bacteria, or more specifically has one genus of ammonia oxidizing bacteria, or more specifically, having one species of ammonia oxidizing e.g., *N. eutropha* and 2, 3, 4, 5, 6, 7, 8, 9, or 10 other types of organism, and no other types of organism. Suitable ammonia-oxidizing bacteria for this purpose include those in the genera *Nitrosomonas, Nitrosococcus, Nitrosospira, Nitrosocystis, Nitrosolobus,* or *Nitrosovibrio*.

In some embodiments, one or more other organisms besides ammonia oxidizing bacteria may be included in the preparation of ammonia oxidizing bacteria. For example, an organism of the genus selected from the group consisting of *Lactobacillus, Streptococcus, Bifidobacter,* and combinations thereof, may be provided in the preparation of ammonia oxidizing bacteria. In some embodiments, the preparation may be substantially free of other organisms.

In some embodiments, the composition, e.g., preparation, comprising ammonia oxidizing bacteria provides conditions that support ammonia oxidizing bacteria viability. For instance, the composition may promote ammonia oxidizing bacteria growth and metabolism or may promote a dormant state (e.g., freezing) or storage state as described herein, from which viable ammonia oxidizing bacteria can be recovered. When the composition promotes growth or metabolism, it may contain water and/or nutrients that ammonia oxidizing bacteria consumes, e.g., as ammonium ions, ammonia, urea, oxygen, carbon dioxide, or trace minerals.

Preparations of ammonia oxidizing bacteria may comprise between about between about $10^8$ to about $10^{14}$ CFU/L. The preparation may comprise at least about $10^8$, $10^9$, $10^{10}$, $10^{11}$, $2 \times 10^{11}$, $5 \times 10^{11}$, $10^{12}$, $2 \times 10^{12}$, $5 \times 10^{12}$, $10^{13}$, $2 \times 10^{13}$, $5 \times 10^{13}$, or $10^{14}$; or about $10^8$-$10^9$, $10^9$-$10^{10}$, $10^{10}$-$10^{11}$, $10^{11}$-$10^{12}$, $10^{12}$-$10^{13}$, or $10^{13}$-$10^{14}$ CFU/L.

Preparations of ammonia oxidizing bacteria may comprise between about between about $10^8$ to about $10^{14}$ CFU/ml. The preparation may comprise at least about $10^8$, $10^9$, $10^{10}$, $10^{11}$, $2 \times 10^{11}$, $5 \times 10^{11}$, $10^{12}$, $2 \times 10^{12}$, $5 \times 10^{12}$, $10^{13}$, $2 \times 10^{13}$, $5 \times 10^{13}$, or $10^{14}$; or about $10^8$-$10^9$, $10^9$-$10^{10}$, $10^{10}$-$10^{11}$, $10^{11}$-$10^{12}$, $10^{12}$-$10^{13}$, or $10^{13}$-$10^{14}$ CFU/ml.

In some embodiments, the preparation of ammonia oxidizing bacteria may comprise between about 0.1 milligrams (mg) to about 100 mg of ammonia oxidizing bacteria. In certain aspects, the preparation may comprise between about 50 mg and about 1000 mg of ammonia oxidizing bacteria. The preparation may comprise between about 0.1-0.5 mg, 0.2-0.7 mg, 0.5-1.0 mg, 0.5-2 mg, 0.5-5 mg, 2.5-5 mg, 2.5-7.0 mg, 5.0-10 mg, 7.5-15 mg, 10-15 mg, 15-20 mg, 15-25 mg, 20-30 mg, 25-50 mg, 25-75 mg, 50-75 mg, 50-100 mg, 75-100 mg, 100-200 mg, 200-300 mg, 300-400 mg, 400-500 mg, 500-600 mg, 600-700 mg, 700-800 mg, 800-900 mg, 900-1000 mg, 100-250 mg, 250-500 mg, 100-500 mg, 500-750 mg, 750-1000 mg, or 500-1000 mg.

In some embodiments, the preparation of ammonia oxidizing bacteria my comprise a mass ratio of ammonia oxidizing bacteria to an excipient, e.g., a pharmaceutically acceptable excipient or a cosmetically acceptable excipient in a range of about 0.1 grams per liter to about 1 gram per liter. The preparation may comprise a mass ratio of ammonia oxidizing bacteria to an excipent in a range of about 0.1-0.2, 0.2-0.3, 0.1-0.5, 0.2-0.7, 0.5-1.0, or 0.7-1.0 grams per liter.

In some embodiments, the preparation of ammonia oxidizing bacteria may be ammonia oxidizing bacteria in a buffer solution comprising, consisting essentially of, or consisting of disodium phosphate and magnesium chloride, for example, 50 mM $Na_2HPO_4$ and 2 mM $MgCl_2$. The preparation may be provided in a buffer at a pre-determined volume of, for example, between about 0.1 and about 100 fluid ounces, about 0.2 and about 50 fluid ounces, about 0.5 and about 25 fluid ounces, about 1.0 and about 10 fluid ounces, about 2.0 and about 7 fluid ounces, about 3 and about 5 fluid ounces. In some embodiments, the preparation may be provided in a container. The preparation may be provided in a container constructed to contain about 3.4 fluid ounces, or any other volume disclosed herein. The preparation may be in a form that may be capable of being aerosolized, sprayed or misted, i.e., in the form of a mist.

The ammonia oxidizing bacteria may be combined with one or more excipients, e.g., one or more pharmaceutically acceptable excipients or cosmetically acceptable excipients. In some embodiments, "pharmaceutically acceptable excipient" refers to a pharmaceutically-acceptable material, composition, or vehicle, such as a liquid or solid filler, diluent, solvent, or encapsulating material. In some embodiments, each excipient is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, Remington: The Science and Practice of Pharmacy, 21st ed.; Lippincott Williams & Wilkins: Philadelphia, Pa., 2005; Handbook of Pharmaceutical Excipients, 6th ed.; Rowe et al., Eds.; The Pharmaceutical Press and the American Pharmaceutical Association: 2009; Handbook of Pharmaceutical Additives, 3rd ed.; Ash and Ash Eds.; Gower Publishing Company: 2007; Pharmaceutical Preformulation and Formulation, 2nd ed.; Gibson Ed.; CRC Press LLC: Boca Raton, Fla., 2009.

In some embodiments, a cosmetically acceptable excipient refers to a cosmetically acceptable material, composition, or vehicle, such as a liquid or solid filler, diluent, solvent, or encapsulating material. In some embodiments, each excipient is cosmetically acceptable in the sense of being compatible with the other ingredients of a cosmetic formulation, and suitable for use in contact with the tissue or organ of humans and animals without excessive toxicity, irritation, allergic response, immunogenicity, or other problems or complications, commensurate with a reasonable benefit/risk ratio.

The excipient, e.g., the pharmaceutically acceptable excipient or the cosmetically acceptable excipient may be provided in the containers and kits of the present disclosure, e.g., within a preparation of ammonia oxidizing bacteria, within an activator, or within one or more chambers, e.g., a first chamber, second chamber, or mixing chamber of the container.

While it is possible for the active ingredient, e.g., ammonia oxidizing bacteria, to be administered alone, in many embodiments it is present in a pharmaceutical formulation, preparation, or composition, or a cosmetic formulation, preparation, or composition. Accordingly, this disclosure provides a pharmaceutical formulation (preparation or composition) or a cosmetic formulation (preparation or composition) comprising ammonia oxidizing bacteria and a pharmaceutically acceptable excipient or a cosmetically acceptable excipient. Pharmaceutical compositions and cosmetic compositions may take the form of a formulations as described below.

The pharmaceutical and cosmetic formulations (e.g., preparations or compositions) described herein may include those suitable for oral (e.g., by way of, or for the purposes of depositing in the gastrointestinal tract), parenteral (including subcutaneous, intradermal, intramuscular, intravenous, and intraarticular), inhalation (including fine particle dusts or mists which may be generated by means of various types of metered doses, pressurized aerosols, nebulizers or insufflators, and including intranasally (nasal) or via the lungs (pulmonary)), rectal and topical (including dermal, transdermal, transmucosal, buccal, sublingual, and intraocular) administration, although the most suitable route may depend upon, for example, the condition and disorder of the recipient.

The formulations (e.g., preparations or compositions) may conveniently be presented in unit dosage form and may be prepared by any of the methods known in the art of pharmacy or cosmetology. Typically, methods include the step of bringing the active ingredient (e.g., ammonia oxidizing bacteria) into association with a pharmaceutical or a comestic carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations may be presented as discrete units such as capsules, cachets or tablets, each containing a predetermined amount of ammonia oxidizing bacteria; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42:2 S, 1988.

The ammonia oxidizing bacteria compositions, or preparations, can, for example, be administered in a form suitable for immediate release or controlled (extended) release. Suitable examples of sustained-release systems include suitable polymeric materials, for example semi-permeable polymer matrices in the form of shaped articles, e.g., films, or microcapsules; suitable hydrophobic materials, for example as an emulsion in an acceptable oil; or ion exchange resins. Controlled (sustained)-release systems may be administered orally; rectally; parenterally; intracistemally; intravaginally; intraperitoneally; topically, for example as a powder, ointment, gel, drop or transdermal patch; bucally; or as a spray.

Preparations for administration can be suitably formulated to give controlled release of ammonia oxidizing bacteria. For example, the formulations, preparations, or compositions may be in the form of particles comprising one or more of biodegradable polymers, polysaccharide jellifying and/or bioadhesive polymers, or amphiphilic polymers. These compositions exhibit certain biocompatibility features which allow a controlled release of an active substance. See U.S. Pat. No. 5,700,486. The preparation may comprise a controlled release material.

In certain instances in this disclosure sustained-release or control-release systems may be referred to as a barrier.

Exemplary compositions, e.g., as a preparation, may include suspensions which can contain, for example, microcrystalline cellulose for imparting bulk, alginic acid or sodium alginate as a suspending agent, methylcellulose as a viscosity enhancer, dicalcium phosphate, starch, magnesium stearate and/or lactose and/or other excipients, binders, extenders, disintegrants, diluents and lubricants, mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, surfactants, glidants, flavors, coloring agents and stabilizers may also be added for ease of fabrication and use. The surfactant may be a zwitterionic surfactant, a non-ionic surfactant, or an anionic surfactant.

Surfactants that may be used with embodiments of the present disclosure may include one or more of cocamidopropyl betaine (ColaTeric COAB), polyethylene sorbitol ester (e.g., Tween 80), ethoxylated lauryl alcohol (RhodaSurf 6 NAT), sodium laureth sulfate/lauryl glucoside/cocamidopropyl betaine (Plantapon 611 L UP), sodium laureth sulfate (e.g., RhodaPex ESB 70 NAT), alkyl polyglucoside (e.g., Plantaren 2000 N UP), sodium laureth sulfate (Plantaren 200), Dr. Bronner's Castile soap, Lauramine oxide (ColaLux Lo), sodium dodecyl sulfate (SDS), polysulfonate alkyl polyglucoside (PolySufanate 160 P), sodium lauryl sulfate (Stepanol-WA Extra K). and combinations thereof. Dr. Bronner's Castile soap comprises water, organic coconut oil, potassium hydroxide, organic olive oil, organic fair deal hemp oil, organic jojoba oil, citric acid, and tocopherol In some embodiments, surfactants may be used with ammonia oxidizing bacteria in amounts that allow nitrite production to occur. In some embodiments, the preparation may have less than about 0.01% to about 10% of surfactant. In some embodiments, the concentration of surfactant used may be between about 0.0001% and about 10%. In some embodiments, the preparation may be substantially free of surfactant.

In some embodiments, the formulation, e.g., preparation, may include other components that may enhance effectiveness of ammonia oxidizing bacteria, or enhance a treatment or indication.

In some embodiments, a chelator may be included in the preparation. A chelator may be a compound that may bind with another compound, e.g., a metal. The chelator may provide assistance in removing an unwanted compound from an environment, or may act in a protective manner to reduce or eliminate contact of a particular compound with an environment, e.g., ammonia oxidizing bacteria, e.g. a preparation of ammonia oxidizing bacteria, e.g., an excipient.

Formulations (e.g., preparations) may also contain antioxidants, buffers, bacteriostats that prevent the growth of undesired bacteria, solutes, and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of a sterile liquid carrier, for example saline or water-for-injection, immediately prior to use. Extemporaneous solutions and suspensions may be prepared from powders, granules and tablets of the kind previously described. Exemplary compositions include solutions or suspensions which can contain, for example, suitable non-toxic, pharmaceutically acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor. An aqueous carrier may be, for example, an isotonic buffer solution at a pH of from about 3.0 to about 8.0, a pH of from about 3.5 to about 7.4, for example from 3.5 to 6.0, for example from 3.5 to about 5.0. Useful buffers include sodium citrate-citric acid and sodium phosphate-phosphoric acid, and sodium acetate/acetic acid buffers. The composition in some embodiments does not include oxidizing agents.

Excipients that can be included are, for instance, proteins, such as human serum albumin or plasma preparations. If desired, the pharmaceutical composition, e.g., a preparation, may also contain minor amounts of non-toxic auxiliary substances, such as wetting or emulsifying agents, surfactants, preservatives, and pH buffering agents and the like, for example sodium acetate or sorbitan monolaurate. In some embodiments, excipients, e.g., a pharmaceutically acceptable excipient or a cosmetically acceptable excipient, may comprise an anti-adherent, binder, coat, disintegrant, filler, flavor, color, lubricant, glidant, sorbent, preservative, or sweetener. In some embodiments, the preparation may be substantially free of excipients.

Exemplary compositions for aerosol administration include solutions in saline, which can contain, for example, benzyl alcohol or other suitable preservatives, absorption promoters to enhance bioavailability, and/or other solubilizing or dispersing agents. Conveniently in compositions for aerosol administration the ammonia oxidizing bacteria may be delivered in the form of an aerosol spray presentation from a pressurized pack or a nebulizer, with the use of a suitable propellant, e.g., dichlorodifluoro-methane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin can be formulated to contain a powder mix of the ammonia oxidizing bacteria and a suitable powder base, for example lactose or starch. In certain embodiments, ammonia oxidizing bacteria is administered as an aerosol from a metered dose valve, through an aerosol adapter also known as an actuator. Optionally, a stabilizer is also included, and/or porous particles for deep lung delivery are included (e.g., see U.S. Pat. No. 6,447,743). The composition or preparation may be in a form that may be capable of being aerosolized, sprayed or misted, i.e., in the form of a mist. The preparation of ammonia oxidizing bacteria may be ammonia oxidizing bacteria in a buffer solution comprising, consisting essentially of, or consisting of disodium phosphate and magnesium chloride, for example, 50 mM $Na_2HPO_4$ and 2 mM $MgCl_2$.

Formulations may be presented with carriers such as cocoa butter, synthetic glyceride esters or polyethylene glycol. Such carriers are typically solid at ordinary temperatures, but liquefy and/or dissolve at body temperature to release the ammonia oxidizing bacteria.

Exemplary compositions for topical administration include a topical carrier such as Plastibase (mineral oil gelled with polyethylene). In some aspects, the composition, e.g., preparation, and/or excipient may be in the form of one or more of a liquid, a solid, or a gel. For example, liquid suspensions may include, but are not limited to, water, saline, phosphate-buffered saline, or an ammonia oxidizing storage buffer.

Gel formulations may include, but are not limited to agar, silica, polyacrylic acid (for example Carbopol®), carboxymethul cellulose, starch, guar gum, alginate or chitosan. In some embodiments, the formulation, e.g., preparation, may be supplemented with an ammonia source including, but not limited to one or more of ammonia, ammonium ions, e.g., ammonium chloride or ammonium sulfate, and urea.

In some embodiments, an ammonia oxidizing bacteria composition, e.g., preparation, is formulated to improve NO penetration into the skin. A gel-forming material such as KY jelly or various hair gels would present a diffusion barrier to NO loss to ambient air, and so improve the skin's absorption of NO. The NO level in the skin will generally not greatly exceed 20 nM/L because that level activates GC and would cause local vasodilatation and oxidative destruction of excess NO.

It should be understood that in addition to the ingredients particularly mentioned above, the formulations, e.g., preparations, as described herein may include other agents conventional in the art having regard to the type of formulation in question.

The formulation, e.g., preparation, e.g., composition may be provided in a container, delivery system, or delivery device, having a weight, including or not including the contents of the container, that may be less than about 50, 100, 200, 300, 400, 500, 600, 700, 800, 900, 1000, 1500, or 2000 grams.

Suitable unit dosage formulations are those containing an effective dose, as hereinbefore recited, or an appropriate fraction thereof, of ammonia oxidizing bacteria.

A therapeutically effective amount of ammonia oxidizing bacteria may be administered as a single pulse dose, as a bolus dose, or as pulse doses administered over time. Thus, in pulse doses, a bolus administration of ammonia oxidizing bacteria is provided, followed by a time period wherein ammonia oxidizing bacteria is administered to the subject, followed by a second bolus administration. In specific, non-limiting examples, pulse doses are administered during the course of a day, during the course of a week, or during the course of a month.

In some embodiments, a preparation of ammonia oxidizing bacteria, e.g., a formulation, e.g., a composition, may be applied for a pre-determined number of days. This may be based, for example, at least in part, on the severity of the condition or disease, the response to the treatment, the dosage applied and the frequency of the dose. For example, the preparation may be applied for about 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days. In certain aspects, the preparation may be applied for about 16 days.

In some embodiments, a preparation of ammonia oxidizing bacteria, e.g., a formulation, e.g., a composition, may be applied a pre-determined number of times per day. This may be based, for example, at least in part, on the severity of the condition or disease, the response to the treatment, the dosage applied and the frequency of the dose. For example, the preparation may be applied 1, 2, 3, 4, 5, 6, 7, 8, 9, 10, 11, 12, 13, 14, 15, 16, 17, 18, 19, 20, 21, 22, 23, 24 times per day.

In some embodiments, the preparation may be applied one time per day. In other embodiments, the preparation may be applied two times per day. In some embodiments, the preparation may be applied a first pre-determined amount for a certain number of days, and a second pre-determined amount for a certain subsequent number of days. In some embodiments, the preparation may be applied for about 16 days.

In some embodiments, the ammonia oxidizing bacteria is administered for about 1-3, 3-5, 5-7, 7-9, 5-10, 10-14, 12-18, 12-21, 21-28, 28-35, 35-42, 42-49, 49-56, 46-63, 63-70, 70-77, 77-84, 84-91 days, e.g., for about 1 month, for about 2 months, for about 3 months. In some embodiments, the ammonia oxidizing bacteria is administered for an indefinite period of time, e.g, greater than one year, greater than 5 years, greater than 10 years, greater than 15 years, greater than 30 years, greater than 50 years, greater than 75 years.

Ammonia oxidizing bacteria may be associated with a variety of consumer and therapeutic products, and examples of such products are set out below. In some embodiments, the ammonia oxidizing bacteria associated with a product is admixed with the product, for example, spread evenly throughout the product, and in some embodiments, the ammonia oxidizing bacteria associated with a product is layered on the product.

In some embodiments, the ammonia oxidizing bacteria is associated with a powder. Powders are typically small particulate solids that are not attached to each other and that can flow freely when tilted. Exemplary powders for consumer use include talcum powder and some cosmetics (e.g., powder foundation, including pressed powders). Other powders may be contemplated for use in conjunction with ammonia oxidizing bacteria systems and methods of the present disclosure.

In some embodiments, the ammonia oxidizing bacteria is associated with a cosmetic. The cosmetic may be a substance for topical application intended to alter a person's appearance, e.g., a liquid foundation, a powder foundation, blush, or lipstick. The cosmetic may be any substance recited in the Food and Drug Administration regulations, e.g., under 21 C.F.R. § 720.4.

The preparation, e.g., cosmetic, may be provided as or disposed in at least one of a baby product, e.g., a baby shampoo, a baby lotion, a baby oil, a baby powder, a baby cream; a bath preparation, e.g., a bath oil, a tablet, a salt, a bubble bath, a bath capsule; an eye makeup preparation, e.g., an eyebrow pencil, an eyeliner, an eye shadow, an eye lotion, an eye makeup remover, a mascara; a fragrance preparation, e.g., a colognes, a toilet water, a perfume, a powder (dusting and talcum), a sachet; hair preparations, e.g., hair conditioners, hair sprays, hair straighteners, permanent waves, rinses, shampoos, tonics, dressings, hair grooming aids, wave sets; hair coloring preparations, e.g., hair dyes and colors, hair tints, coloring hair rinses, coloring hair shampoos, hair tighteners with color, hair bleaches; makeup preparations, e.g., face powders, foundations, leg and body paints, lipstick, makeup bases, rouges, makeup fixatives; manicuring preparations, e.g., basecoats and undercoats, cuticle softeners, nail creams and lotions, nail extenders, nail polish and enamel, nail polish and enamel removers; oral hygiene products, e.g., dentrifices, mouthwashes and breath fresheners; bath soaps and detergents, deodorants, douches, feminine hygiene deodorants; shaving preparations, e.g., aftershave lotions, beard softeners, talcum, preshave lotions, shaving cream, shaving soap; skin care preparations, e.g., cleansing, depilatories, face and neck, body and hand, foot powders and sprays, moisturizing, night preparations, paste masks, skin fresheners; and suntan preparations, e.g., gels, creams, and liquids, and indoor tanning preparations.

In some embodiments, preparation, e.g., cosmetic, may be provided as or disposed in at least one of a baby product, e.g., a baby shampoo, a baby lotion, a baby oil, a baby powder, a baby cream; a bath preparation, e.g., a bath oil, a tablet, a salt, a bubble bath, a bath capsule; a powder (dusting and talcum), a sachet; hair preparations, e.g., hair conditioners, rinses, shampoos, tonics, face powders, cuticle softeners, nail creams and lotions, oral hygiene products, mouthwashes, bath soaps, douches, feminine hygiene deodorants; shaving preparations, e.g., aftershave lotions, skin care preparations, e.g., cleansing, face and neck, body and hand, foot powders and sprays, moisturizing, night preparations, paste masks, skin fresheners; and suntan preparations, e.g., gels, creams, and liquids.

Other components may be added to pharmaceutical formulations, e.g., preparations, or cosmetic preparations as selected by one skilled in the art of cosmetic formulation such as, for example, water, mineral oil, coloring agent, perfume, aloe, glycerin, sodium chloride, sodium bicarbonate, pH buffers, UV blocking agents, silicone oil, natural oils, vitamin E, herbal concentrates, lactic acid, citric acid, talc, clay, calcium carbonate, magnesium carbonate, zinc oxide, starch, urea, and erythorbic acid, or any other excipient known by one of skill in the art, including those disclosed herein.

In some embodiments, the preparation may be disposed in, or provided as, a powder, cosmetic, cream, stick, aerosol, salve, wipe, or bandage.

In some embodiments, ammonia oxidizing bacteria is associated with a cream. The cream may be a fluid comprising a thickening agent, and generally has a consistency that allows it to be spread evenly on the skin. Exemplary creams include moisturizing lotion, face cream, and body lotion.

In some embodiments, the ammonia oxidizing bacteria is associated with a stick. A stick is typically a solid that, when placed in contact with a surface, transfers some of the stick contents to the surface. Exemplary sticks include deodorant stick, lipstick, lip balm in stick form, and sunscreen applicator sticks.

In some embodiments, the ammonia oxidizing bacteria is associated with an aerosol. An aerosol is typically a colloid of fine solid particles or fine liquid droplets, in a gas such as air. Aerosols may be created by placing the ammonia oxidizing bacteria (and optionally carriers) in a vessel under pressure, and then opening a valve to release the contents. The container may be designed to only exert levels of pressure that are compatible with ammonia oxidizing bacteria viability. For instance, the high pressure may be exerted for only a short time, and/or the pressure may be low enough not to impair viability. Examples of consumer uses of aerosols include for sunscreen, deodorant, perfume, hairspray, and insect repellant.

In some embodiments, the ammonia oxidizing bacteria is associated with a salve. A salve may be a topically applied agent with a liquid or cream-like consistency, intended to protect the skin or promote healing. Examples of salves include burn ointments and skin moisturizers.

In some embodiments, the ammonia oxidizing bacteria is associated with a wipe. A wipe may be a flexible material suitable for topically applying a liquid or cream onto skin. The wipe may be, e.g., paper-based or cloth based. Exemplary wipes include tissues and wet wipes.

The compositions comprising ammonia oxidizing bacteria may also comprise one or more of a moisturizing agent, deodorizing agent, scent, colorant, insect repellant, cleansing agent, or UV-blocking agent.

For instance, the moisturizing agent may be an agent that reduces or prevents skin dryness. Exemplary moisturizing agents include humectants (e.g., urea, glycerin, alpha hydroxy acids and dimethicone) and emollients (e.g., lanolin, mineral oil and petrolatum). Moisturizing agents may be included, e.g., in ammonia oxidizing bacteria-containing creams, balms, lotions, or sunscreen.

A deodorizing agent may be an agent that reduces unwanted odors. A deodorizing agent may work by directly neutralizing odors, preventing perspiration, or preventing the growth of odor-producing bacteria. Exemplary deodorizing agents include aluminum ions (e.g., aluminum chloride or aluminum chlorohydrate), cyclomethicone, talc, baking soda, essential oils, mineral ions, hops, and witch hazel. Deodorizing agents are typically present in spray or stick deodorants, and can also be found in some soaps and clothing.

An insect repellant may be an agent that can be applied to surfaces (e.g., skin) that discourage insects and other arthropods from lighting on the surface. Insect repellants include DEET (N,N-diethyl-m-toluamide), p-menthane-3,8-diol (PMD), icaridin, nepetalactone, citronella oil, neem oil, bog myrtle, dimethyl carbate, Tricyclodecenyl allyl ether, and IR3535 (3-[N-Butyl-N-acetyl]-aminopropionic acid, ethyl ester).

A cleansing agent may be an agent that removes dirt or unwanted bacteria from a surface like skin. Exemplary cleansing agents include bar soaps, liquid soaps, and shampoos.

A UV-blocking agent may be an agent that can be applied to a surface to reduce the amount of ultraviolet light the surface receives. A UV-blocking agent may block UV-A and/or UV-B rays. A UV blocking agent can function by absorbing, reflecting, or scattering UV. Exemplary UV-blocking agents include absorbers, e.g., homosalate, octisalate (also called octyl salicylate), octinoxate (also called octyl methoxycinnamate or OMC), octocrylene, oxybenzone, and avobenzone, and reflectors (e.g., titanium dioxide and zinc oxide). UV-blocking agents are typically presenst in sunscreens, and can also be found in skin creams and some cosmetics.

In some embodiments, ammonia oxidizing bacteria is associated with a conditioner. Conditioner generally refers to a substance with cream-like consistency that can be applied to hair to improve its appearance, strength, or manageability.

In some embodiments, ammonia oxidizing bacteria is associated with cloth. Cloth generally refers to a flexible material suitable to be made into clothing, e.g., having enough material strength to withstand everyday motion by a wearer. Cloth can be fibrous, woven, or knit; it can be made of a naturally occurring material or a synthetic material. Exemplary cloth materials include cotton, flax, wool, ramie, silk, denim, leather, nylon, polyester, and spandex, and blends thereof.

In some embodiments, ammonia oxidizing bacteria is associated with yarn. Yarn generally refers to a long, thin spun flexible material that is suitable for knitting or weaving. Yarn can be made of, e.g., wool, cotton, polyester, and blends thereof.

In some embodiments, ammonia oxidizing bacteria is associated with thread. Thread generally refers to a long, thin spun flexible material that is suitable for sewing. Thread generally has a thinner diameter than yarn. Thread can be made of, e.g., cotton, polyester, nylon, silk, and blends thereof.

Articles of clothing such as, for example, shoes, shoe inserts, pajamas, sneakers, belts, hats, shirts, underwear, athletic garments, helmets, towels, gloves, socks, bandages, and the like, may also be treated with ammonia oxidizing bacteria. Bedding, including sheets, pillows, pillow cases, and blankets may also be treated with ammonia oxidizing bacteria. In some embodiments, areas of skin that cannot be washed for a period of time may also be contacted with ammonia oxidizing bacteria. For example, skin enclosed in orthopedic casts which immobilize injured limbs during the healing process, and areas in proximity to injuries that must be kept dry for proper healing such as stitched wounds may benefit from contact with the ammonia oxidizing bacteria.

In some aspects, the present disclosure provides a wearable article comprising an ammonia oxidizing bacterium or ammonia oxidizing bacteria as described herein. A wearable article may be a light article that can be closely associated with a user's body, in a way that does not impede ambulation. Examples of wearable articles include a wristwatch, wristband, headband, hair elastic, hair nets, shower caps, hats, hairpieces, and jewelry. The wearable article comprising ammonia oxidizing bacteria described herein may provide, e.g., at a concentration that provides one or more of a treatment or prevention of a skin disorder, a treatment or prevention of a disease or condition associated with low nitrite levels, a treatment or prevention of body odor, a treatment to supply nitric oxide to a subject, or a treatment to inhibit microbial growth.

In some embodiments, the ammonia oxidizing bacteria is associated with a product intended to contact the hair, for example, a brush, comb, shampoo, conditioner, headband, hair elastic, hair nets, shower caps, hats, and hairpieces. Nitric oxide formed on the hair, away from the skin surface, may be captured in a hat, scarf or face mask and directed into inhaled air.

Articles contacting the surface of a human subject, such as a diaper, may be associated with ammonia oxidizing bacteria. Because diapers are designed to hold and contain urine and feces produced by incontinent individuals, the urea in urine and feces can be hydrolyzed by skin and fecal bacteria to form free ammonia which is irritating and may cause diaper rash. Incorporation of bacteria that metabolize urea into nitrite or nitrate, such as ammonia oxidizing bacteria, may avoid the release of free ammonia and may release nitrite and ultimately NO which may aid in the maintenance of healthy skin for both children and incontinent adults. The release of nitric oxide in diapers may also have anti-microbial effects on disease causing organisms present in human feces. This effect may continue even after disposable diapers are disposed of as waste and may reduce the incidence of transmission of disease through contact with soiled disposable diapers.

In some embodiments, the product comprising ammonia oxidizing bacteria is packaged. The packaging may serve to compact the product or protect it from damage, dirt, or degradation. The packaging may comprise, e.g., plastic, paper, cardboard, or wood. In some embodiments the packaging is impermeable to bacteria. In some embodiments the packaging is permeable to oxygen and/or carbon dioxide.

9. Methods of Treatment with Ammonia Oxidizing Bacteria

The present disclosure provides various methods of treating diseases and conditions using ammonia oxidizing bacteria, e.g., by administering ammonia oxidizing bacteria, e.g., a preparation of ammonia oxidizing bacteria, e.g., a natural product or a fortified natural product (a fortified natural product being fortified with ammonia oxidizing bacteria, e.g., exogenous ammonia oxidizing bacteria), or compositions, preparations, or formulations comprising a natural product or a fortified natural product.

The ammonia oxidizing bacteria that may be used to treat diseases and conditions include all the ammonia oxidizing bacteria compositions described in this application, e.g. a preparation of ammonia oxidizing bacteria, a natural product or a fortified natural product, or compositions, preparations, or formulations comprising a natural product or a fortified natural product.

For instance, the disclosure provides uses, for treating a condition or disease (e.g., inhibiting microbial growth on a subject's skin), a composition of ammonia oxidizing bacteria. In embodiments, the ammonia oxidizing bacteria may be used to treat ulcers or infections in ulcers, e.g., venous ulcer, e.g., leg ulcer, e.g., venous leg ulcer, e.g., diabetic ulcers, e.g., diabetic foot ulcers, chronic wounds, acne, e.g., acne vulgaris, rosacea, eczema, uticaria, or psoriasis.

The container and kits of the present disclosure may provide for, or contain contents, to be useful for treating or preventing a skin disorder, treating or preventing a disease or condition associated with low nitrite levels, a treating or preventing body odor, treating to supply nitric oxide to a subject, or treating to inhibit microbial growth.

The container and kits of the present disclosure may provide for, or contain contents, to be useful in a treatment of at least one of HIV dermatitis, infection in an ulcer, e.g., venous ulcer, e.g., leg ulcer, e.g., venous leg ulcer, e.g. infection in a diabetic foot ulcer, atopic dermatitis, acne, e.g., acne vulgaris, eczema, contact dermatitis, allergic reaction, psoriasis, uticaria, rosacea, skin infections, vascular disease, vaginal yeast infection, a sexually transmitted disease, heart disease, atherosclerosis, baldness, leg ulcers secondary to diabetes or confinement to bed, angina, particularly chronic, stable angina pectoris, ischemic diseases, congestive heart failure, myocardial infarction, ischemia reperfusion injury, laminitis, hypertension, hypertrophic organ degeneration, Raynaud's phenomenon, fibrosis, fibrotic organ degeneration, allergies, autoimmune sensitization, end stage renal disease, obesity, impotence, pneumonia, primary immunodeficiency, epidermal lysis bulosa, or cancer. In embodiments, the condition is a venous leg ulcer.

In some embodiments, ammonia oxidizing bacteria are used to treat a subject. Subjects may include an animal, a mammal, a human, a non-human animal, a livestock animal, or a companion animal.

In some embodiments, ammonia oxidizing bacteria described herein are used to inhibit the growth of other organisms. For instance, ammonia oxidizing bacteria may be well-adapted for long-term colonization of human skin, and in some embodiments it out-competes other bacteria that are undesirable on the skin. Undesirable skin bacteria include, e.g., those that can infect wounds, raise the risk or severity of a disease, or produce odors. Undesirable bacteria may be referred to as pathogenic bacteria. Certain undesirable skin bacteria, e.g., potentially pathogenic bacteria, e.g., pathogenic bacteria, include *Staphylococcus aureus* (*S. aureus*), e.g., methicillin resistant *Staphylococcus aureus Psuedomomas aeruginosa* (*P. aeruginosa*), *Streptococcus pyogenes* (*S. pyogenes*), *Acinetobacter baumannii* (*A. baumannii*), *Propionibacteria*, and *Stenotrophomonas*. The ammonia oxidizing bacteria described herein may out-compete other organisms by, e.g., consuming scarce nutrients, or generating byproducts that are harmful to other organisms, e.g., changing the pH of the skin to a level that is not conducive to the undesirable organism's growth.

Accordingly, the present disclosure provides, inter alia, a method of inhibiting microbial growth on a subject's skin, comprising topically administering to a human in need thereof an effective dose of ammonia oxidizing bacteria as described herein. Similarly, the present disclosure provides ammonia oxidizing bacteria as described herein for use in inhibiting microbial growth on a subject's skin. Likewise, the present disclosure provides a use of ammonia oxidizing bacteria in the manufacture of a medicament for inhibiting microbial growth on a subject's skin.

The present disclosure also provides a method of supplying nitric oxide to a subject, comprising positioning an effective dose of ammonia oxidizing bacteria described herein in close proximity to the subject. Similarly, the present disclosure provides ammonia oxidizing bacteria as described herein for use in supplying nitric oxide to a subject. Likewise, the present disclosure provides a use of ammonia oxidizing bacteria in the manufacture of a medicament or composition suitable for position in close proximity to a subject.

The present disclosure also provides a method of reducing body odor, comprising topically administering to a subject in need thereof an effective dose of ammonia oxidizing bacteria described herein. Similarly, the present disclosure provides ammonia oxidizing bacteria as described herein for use in reducing body odor in a subject. Likewise, the present disclosure provides a use of ammonia oxidizing bacteria as described herein in the manufacture of a medicament or composition for reducing body odor.

The present disclosure also provides a method of treating or preventing a disease associated with low nitrite levels, comprising topically administering to a subject in need thereof a therapeutically effective dose of ammonia oxidizing bacteria described herein. Similarly, the present disclosure provides a topical formulation of ammonia oxidizing bacteria as described herein for use in treating a disease associated with low nitrite levels. Likewise, the present disclosure provides a use of ammonia oxidizing bacteria as described herein in the manufacture of a topical medicament for treating a disease associated with low nitrite levels.

The present disclosure also provides a method of treating or preventing a skin disorder or skin infection, comprising topically administering to a subject in need thereof a therapeutically effective dose of ammonia oxidizing bacteria as described herein. Similarly, the present disclosure provides ammonia oxidizing bacteria as described herein for use in treating a skin disorder in a subject. Likewise, the present disclosure provides a use of ammonia oxidizing bacteria as described herein in the manufacture of a medicament for treating skin disorder. In embodiments, the skin disorder is acne, e.g., acne vulgaris, rosacea, eczema, psoriasis, or urticaria; the skin infection is impetigo.

While not wishing to be bound by theory, it is proposed that treatment of acne, e.g., acne vulgaris, with a therapeutically effective dose of ammonia oxidizing bacteria; and/or limiting and/or inhibiting the spread and proliferation of *Propionibacterium acnes* associated with acne vulgaris through acidified nitrite and NO production.

While not wishing to be bound by theory, it is proposed that treatment of rosacea with a therapeutically effective dose of ammonia oxidizing bacteria as described herein may involve downregulation due to NO generation. This may be due to expression of Kazal-type KLK5/KLK7 inhibitor(s) that may reduce formation of the human cathelicidin peptide LL-37 from its precursor propeptide hCAP18.

While not wishing to be bound by theory, it is proposed that treatment of eczema and/or atopic dermatitis with a therapeutically effective dose of as described herein may involve donwregulation of inflammation due to NO generation; and/or limiting and/or inhibiting the spread and proliferation of *S. aureus* and other skin pathogens often associated with very high colonization rates and skin loads in atopic dermatitis through acidified nitrite and NO production.

While not wishing to be bound by theory, it is proposed that treatment of psoriasis with a therapeutically effective dose of ammonia oxidizing bacteria described herein may involve downregulation of inflammation due to NO generation and reduction in formation of human cathelicidin peptide LL-37.

While not wishing to be bound by theory, it is proposed that treatment of psoriasis with a therapeutically effective dose of ammonia oxidizing bacteria as described herein may involve downregulation of inflammation due to NO generation.

While not wishing to be bound by theory, it is proposed that treatment of impetigo or other skin and soft tissue infections with a therapeutically effective dose of ammonia oxidizing bacteria as described herein may involve limiting and/or inhibiting the spread and proliferation of *Staphylococcus aureus* (*S. aureus*), *Psuedomomas aeruginosa* (*P. aeruginosa*), *Streptococcus pyogenes* (*S. pyogenes*), *Acinetobacter baumannii* (*A. baumannii*), *Propionibacteria*, and *Stenotrophomonas*.

The present disclosure also provides a method of promoting wound healing, comprising administering to a wound an effective dose of ammonia oxidizing bacteria as described herein. Similarly, the present disclosure provides ammonia oxidizing bacteria as described herein for use in treating a wound. Likewise, the present disclosure provides a use of ammonia oxidizing bacteria as described herein in the manufacture of a medicament or a composition for treating a wound.

Ammonia oxidizing bacteria as described herein may be used to promote wound healing in a patient that has an impaired healing ability, e.g., a diabetic patient.

In some embodiments, this disclosure provides methods of using ammonia oxidizing bacteria as described herein to prevent a disease or disorder, e.g., a skin disorder. Prevention, in certain embodiments, means reducing the risk of a subject developing a disease, compared to a similar untreated subject. The risk need not be reduced to zero.

In some embodiments, a method of changing a composition of a skin microbiome of a subject is provided. The method may comprise administering, e.g., applying, a preparation comprising ammonia oxidizing bacteria to a surface of the skin. The amount and frequency of administration, e.g., application, is sufficient to reduce the proportion of pathogenic bacteria on the surface of the skin. The subject may be selected on the basis of the subject being in need of a reduction in the proportion of pathogenic bacteria on the surface of the skin. This may be provided using any one of the containers, delivery devices, delivery systems, or kits of the present disclosure.

Individuals having a reduced bathing frequency, such as astronauts, submarine crew members, military personnel during a campaign, civilian workers in remote locations, refugees, bedridden individuals and many others may maintain healthier skin by maintaining ammonia oxidizing bacteria on the skin. With regard to bedridden individuals, the ammonia oxidizing bacteria in some embodiments reduces the frequency or severity of bed sores by augmenting inadequate circulation.

It is appreciated that many modern degenerative diseases may be caused by a lack of NO species, and that ammonia oxidizing bacteria on the external skin can supply those species by diffusion, and that application of ammonia oxidizing bacteria to the skin resolves long standing medical conditions. In certain embodiments, ammonia oxidizing bacteria are applied to a subject to offset modern bathing practices, especially with anionic detergents remove ammonia oxidizing bacteria from the external skin.

One suitable method of topical application to apply sufficient ammonia oxidizing bacteria and then wear sufficient clothing so as to induce sweating. However, many people will want to derive the benefits of ammonia oxidizing bacteria while maintaining their current bathing habits, in which case, a culture of the bacteria can be applied along with sufficient substrate for them to produce NO. A nutrient solution approximating the inorganic composition of human sweat can be used for this purpose. Using bacteria adapted to media approximating human sweat minimizes the time for them to adapt when applied. Since sweat evaporates once excreted onto the skin surface, using a culture media that has a higher ionic strength is desirable. A concentration approximately twice that of human sweat is suitable, but other conditions are also contemplated Ammonia oxidizing bacteria's nutritional needs are typically met with $NH_3$ or urea, $O_2$, $CO_2$, and minerals. In some embodiments, the substrate comprises trace minerals including iron, copper, zinc, cobalt, molybdenum, manganese, sodium, potassium, calcium, magnesium, chloride, phosphate, sulfate, or any combination thereof.

In some embodiments, the present disclosure provides a method of treating a wound by applying a bandage comprising ammonia oxidizing bacteria to the wound. Also provided are methods of producing such a bandage. The bandage may comprise, for example, an adhesive portion to affix the bandage to undamaged skin near the wound and a soft, flexible portion to cover or overlay the wound. In some embodiments, the bandage contains no other organisms but ammonia oxidizing bacteria. The bandage may made of a permeable material that allows gasses like oxygen and carbon dioxide to reach the ammonia oxidizing bacteria when the bandage is applied to the wound. In certain embodiments, the bandage comprises nutrients for ammonia oxidizing bacteria such as ammonium, ammonia, urea, or trace minerals. In certain embodiments, the bandage comprises an antibiotic to which the ammonia oxidizing bacteria is resistant. The antibiotic resistance may arise from one or more endogenous resistance gene or from one or more transgenes.

In some embodiments, the ammonia oxidizing bacteria e.g., a preparation of ammonia oxidizing bacteria, is administered at a dose of about $10^8$-$10^9$ CFU, $10^9$-$10^{10}$ CFU, $10^{10}$-$10^{11}$ CFU, $10^{11}$-$10^{12}$ CFU, $10^{12}$-$10^{13}$ CFU, or $10^{13}$-$10^{14}$ CFU per application. In some embodiments, the ammonia oxidizing bacteria is administered topically at a dose of about $10^9$-$10^{10}$ CFU, about $1\times10^9$-$5\times10^9$, $1\times10^9$-$3\times10^9$, or $1\times10^9$-$10\times10^9$ CFU; or about $10^{10}$-$10^{11}$ CFU, e.g., about $1\times10^{10}$-$5\times10^{10}$, $1\times10^{10}$-$3\times10^{10}$, or $1\times10^{10}$-$2\times10^{10}$ CFU; or about $10^{11}$-$10^{12}$ CFU, e.g., about $1\times10^{11}$-$5\times10^{11}$, $1\times10^{11}$-$3\times10^{11}$, or $1\times10^{11}$-$2\times10^{11}$ CFU; or about $10^{12}$-$10^{13}$ CFU, e.g., about $1\times10^{12}$-$5\times10^{12}$, $1\times10^{12}$-$3\times10^{12}$, or $1\times10^{12}$-$2\times10^{12}$ CFU; or about $10^{13}$-$10^{14}$ CFU, e.g., about $1\times10^{13}$-$5\times10^{13}$, $1\times10^{13}$-$3\times10^{13}$, or $1\times10^{13}$-$2\times10^{13}$ CFU.

In some embodiments, the ammonia oxidizing bacteria is administered in a volume of about 1-2, 2-5, 5-10, 10-15, 12-18, 15-20, 20-25, or 25-50 ml per dose. In some embodiments, the solution is at a concentration of about $10^8$-$10^9$, $10^9$-$10^{10}$, or $10^{10}$-$10^{11}$ CFUs/ml. In some embodiments, the ammonia oxidizing bacteria is administered as two 15 ml doses per day, where each dose is at a concentration of $10^9$ CFU/ml.

In some embodiments, the ammonia oxidizing bacteria is administered once, twice, three, or four times per day. In some embodiments, the ammonia oxidizing bacteria is administered once, twice, three, four, five, or six times per week. In some embodiments, the ammonia oxidizing bacteria is administered shortly after bathing. In some embodiments, the ammonia oxidizing bacteria is administered shortly before sleep.

In certain aspects, the present disclosure provides combination therapies comprising ammonia oxidizing bacteria and a second therapeutic. For instance, the disclosure provides physical admixtures of the two (or more) therapies are physically admixed. In other embodiments, the two (or more) therapies are administered in combination as separate formulation. The second therapy may be, e.g., a pharmaceutical agent, surgery, or any other medical approach that treats the relevant disease or disorder. The following paragraphs describe combination therapies capable of treating an ulcer, e.g., venous ulcer, e.g., leg ulcer, e.g., venous leg ulcer, e.g. diabetic ulcers, chronic wounds, acne, e.g., acne vulgaris, rosacea, eczema, and psoriasis. The combination therapy may be included in the containers or delivery devices as described herein, or may be delivered using a separate delivery device. The combination therapy may be included in the first chamber, the second chamber, or a third chamber of the container or delivery device. The combination therapy may treat a venous leg ulcer.

For instance, in a combination therapy capable of treating ulcers, e.g., venous ulcer, e.g., leg ulcer, e.g., venous leg ulcer, e.g. diabetic ulcers, the second therapy may comprise, e.g., a wound dressing (e.g., absorptive fillers, hydrogel dressings, or hydrocolloids), angiotensin, angiotensin analogues, platelet-rich fibrin therapy, hyperbaric oxygen therapy, negative pressure wound therapy, debridement, drainage, arterial revascularization, hyperbaric oxygen therapy, low level laser therapy, and gastrocnemius recession. The combination therapy may comprise one or more of the above-mentioned treatments.

In a combination therapy capable of treating chronic wounds, the second therapy may comprise, e.g., an antibiotic (e.g., topical or systemic, and bacteriocidal or bacteriostatic) such as Penicillins, cephalosporins, polymyxins, rifamycins, lipiarmycins, quinolones, sulfonamides, macrolides, lincosamides, tetracyclines, cyclic lipopeptides, glycylcyclines, oxazolidinones, and lipiarmycins; angiotensin, angiotensin analogues; debridement; drainage; wound irrigation; negative pressure wound therapy; application of heat; arterial revascularization; hyperbaric oxygen therapy; antioxidants such as ascorbic acid, glutathione, lipoic acid, carotenes, α-tocopherol, or ubiquinol; low level laser therapy; gastrocnemius recession; growth factors such as vascular endothelial growth factor, insulin-like growth factor 1-2, platelet derived growth factor, transforming growth factor-β, or epidermal growth factor; application of autologous platelets such as those that secrete one or more growth factors such as vascular endothelial growth factor, insulin-like growth factor 1-2, platelet derived growth factor, transforming growth factor-β, or epidermal growth factor; implantation of cultured keratinocytes; allograft; collagen, for instance a dressing comprising collagen; or protease inhibitors such as SLPI. The combination therapy may comprise one or more of the above-mentioned treatments.

In a combination therapy capable of treating acne, e.g., acne vulgaris, the second therapy may comprise, e.g., a medication (e.g., systemic or topical) such as Benzoyl peroxide, antibiotics (such as erythromycin, clindamycin, or a tetracycline), Salicylic acid, hormones (e.g., comprising a progestin such as desogestrel, norgestimate or drospirenone), retinoids such as tretinoin, adapalene, tazarotene, or isotretinoin. The second therapy may also be a procedure such as comedo extraction, corticosteroid injection, or surgical lancing. The combination therapy may comprise one or more of the above-mentioned treatments.

In a combination therapy capable of treating rosacea, the second therapy may comprise, e.g., an antibiotic, e.g., an oral tetracycline antibiotic such as tetracycline, doxycycline, or minocycline, or a topical antibiotic such as metronidazole; azelaic acid; alpha-hydroxy acid; isotretinoin can be prescribed; sandalwood oil; clonidine; beta-blockers such as nadolol and propranolol; antihistamines (such as loratadine); mirtazapine; methylsulfonylmethane or silymarin, optionally in combination with each other; lasers such as dermatological vascular laser or $CO_2$ laser; or light therapies such as intense pulsed light, low-level light therapy or photorejuvenation. The combination therapy may comprise one or more of the above-mentioned treatments.

In a combination therapy capable of treating eczema, the second therapy may comprise, e.g., a corticosteroid such as hydrocortisone or clobetasol propionate, immunosuppressants (topical or systemic) such as pimecrolimus, tacrolimus, ciclosporin, azathioprine or methotrexate, or light therapy such as with ultraviolet light. The combination therapy may comprise one or more of the above-mentioned treatments.

In a combination therapy capable of treating psoriasis, the second therapy may comprise, e.g., a corticosteroid such as desoximetasone; a retinoid; coal tar; Vitamin D or an analogue thereof such as paricalcitol or calcipotriol; moisturizers and emollients such as mineral oil, vaseline, calcipotriol, decubal, or coconut oil; dithranol; or fluocinonide. The combination therapy may comprise one or more of the above-mentioned treatments.

10. Experimental Models for Refining Ammonia Oxidizing Bacteria Treatments

Treatments comprising ammonia oxidizing bacteria as described herein (optionally in combination with another therapy) can be refined using a number of model systems. These model systems can be used to determine suitable doses and timing of administration.

For instance, with respect to chronic wounds and ulcers, e.g., venous ulcers, e.g., diabetic ulcers, or other ulcers disclosed herein, one may use the mouse skin puncture model. Other models for these disorders include controlled cutaneous ischemia in a guinea pig model, rabbit ear ulcer model, application of calcium to a wound, or topical application of doxorubicin.

With respect to acne, e.g., acne vulgaris, one may use (for example) the Mexican hairless dog model, the Rhino mouse model, or the rabbit ear assay. With respect to rosacea, one may use (for example) intradermal injection of LL-37 into mouse skin or the Syrian hamster model. With respect to eczema, one may use (for example) application of a crude extract of Dermatophagoides farina, application of dinitrochlorobenzene to the ears of sensitized guinea pigs, or NC/Nga mice. With respect to psoriasis, one may use (for example) xenograft models in which involved and uninvolved psoriatic skin are transplanted onto immunodeficient mice, application of an antibody directed against interleukin 15 to the skin of SCID mice, and the Sharpin$^{cpdm}$/Sharpin$^{cpdm}$ mouse model.

11. Mechanism of Therapeutic Benefit

While not wishing to be bound by theory, it is believed that one or more of the following mechanisms contributes to the beneficial effect of ammonia oxidizing bacteria are found in International Application WO/2005/030147, which is herein incorporated by reference in its entirety.

In order to understand the beneficial aspects of these bacteria, it is helpful to understand angiogenesis. All body cells, except those within a few hundred microns of the external air, receive all metabolic oxygen from the blood supply. The oxygen is absorbed by the blood in the lung, is carried by red blood cells as oxygenated hemoglobin to the peripheral tissues, where it is exchanged for carbon dioxide, which is carried back and exhaled from the lung. Oxygen must diffuse from the erythrocyte, through the plasma, through the endothelium and through the various tissues until it reached the mitochondria in the cell which consumes it. The human body contains about 5 liters of blood, so the volume of the circulatory system is small compared to that of the body. Oxygen is not actively transported. It passively diffuses down a concentration gradient from the air to the erythrocyte, from the erythrocyte to the cell, and from the cell to cytochrome oxidase where it is consumed. The concentration of oxygen at the site of consumption is the lowest in the body, and the $O_2$ flux is determined by the diffusion resistance and the concentration gradient. Achieving sufficient oxygen supply to all the peripheral tissues requires exquisite control of capillary size and location. If the spacing between capillaries were increased, achieving the same flux of oxygen would require a larger concentration difference and hence a lower $O_2$ concentration at cytochrome oxidase. With more cells between capillaries, the $O_2$ demand would be greater. If the spacing between capillaries were decreased, there would be less space available for the cells that perform the metabolic function of the organ.

In certain aspects, it is appreciated that NO from ammonia oxidizing bacteria is readily absorbed by the outer skin and converted into S-nitrosothiols since the outer skin is free from hemoglobin. M. Stucker et al. have shown that the external skin receives all of its oxygen from the external air in "The cutaneous uptake of atmospheric oxygen contributes significantly to the oxygen supply of human dermis and epidermis. (Journal of Physiology (2002), 538.3, pp. 985-994.) This is readily apparent, because the external skin can be seen to be essentially erythrocyte free. There is circulation of plasma through these layers because they are living and do require the other nutrients in blood, just not the oxygen. S-nitrosothiols formed are stable, can diffuse throughout the body, and constitute a volume source of authentic NO and a source of NO to transnitrosate protein thiols.

In some aspects, it is appreciated that capillary rarefaction may be one of the first indications of insufficient levels of NO. F. T. Tarek et al. have shown that sparse capillaries, or capillary rarefaction, is commonly seen in people with essential hypertension. (Structural Skin Capillary Rarefaction in Essential Hypertension. Hypertension. 1999; 33:998-1001

A great many conditions are associated with the capillary density becoming sparser. Hypertension is one, and researchers reported that sparse capillaries are also seen in the children of people with essential hypertension, and also in people with diabetes. Significant complications of diabetes are hypertension, diabetic nephropathy, diabetic retinopathy, and diabetic neuropathy. R. Candido et al. have found that the last two conditions are characterized by a reduction in blood flow to the affected areas prior to observed symptoms. (Haemodynamics in microvascular complications in type 1 diabetes. Diabetes Metab Res Rev 2002; 18: 286-304.) Reduced capillary density is associated with obesity, and simple weight loss increases capillary density as shown by A Philip et al. in "Effect of Weight Loss on Muscle Fiber Type, Fiber Size, Capilarity, and Succinate Dehydrogenase Activity in Humans. The Journal of Clinical Endocrinology & Metabolism Vol. 84, No. 11 4185-4190, 1999.

Researchers have shown that in primary Raynaud's phenomena (PRP), the nailfold capillaries are sparser (slightly) than in normal controls, and more abundant than in patients that have progressed to systemic sclerosis (SSc). M. Bukhari, Increased Nailfold Capillary Dimensions In Primary Raynaud's Phenomenon And Systemic Sclerosis. British Journal of Rheumatology, Vol. 24 No 35: 1127-1131, 1996. They found that the capillary density decreased from 35 loops/mm$^2$ (normal controls) to 33 (PRP), to 17 (SSc). The average distance between capillary limbs was 18μ, 18μ, and 30μ for controls, PRP and SSc, respectively.

In certain aspects, it is appreciated that the mechanism that the body normally uses to sense "hypoxia" may affect the body's system that regulates capillary density. According to this aspect of the disclosure, a significant component of "hypoxia" is sensed, not by a decrease in O2 levels, but rather by an increase in NO levels. Lowering of basal NO levels interferes with this "hypoxia" sensing, and so affects many bodily functions regulated through "hypoxia." For Example, anemia is commonly defined as "not enough hemoglobin," and one consequence of not enough hemoglobin is "hypoxia", which is defined as "not enough oxygen." According to some aspects, these common definitions do not account for the nitric oxide mediated aspects of both conditions.

At rest, acute isovolemic anemia is well tolerated. A ⅔ reduction in hematocrit has minimal effect on venous return PvO2, indicating no reduction in either $O_2$ tension or delivery throughout the entire body. Weiskopf et al. Human cardiovascular and metabolic response to acute, severe isovolemic anemia. JAMA 1998, vol 279, No. 3, 217-221. At 50% reduction (from 140 to 70 g Hb/L), the average PvO2 (over 32 subjects) declined from about 77% to about 74% (of saturation). The reduction in $O_2$ capacity of the blood is compensated for by vasodilatation and tachycardia with the heart rate increasing from 63 to 85 bpm. That the compensation is effective is readily apparent, however, the mechanism is not. A typical explanation is that "hypoxia" sensors detected "hypoxia" and compensated with vasodilatation and tachycardia. However, there was no "hypoxia" to detect. There was a slight decrease in blood lactate (a marker for anaerobic respiration) from 0.77 to 0.62 mM/L indicating less anaerobic respiration and less "hypoxia." The 3% reduction in venous return PvO2 is the same level of "hypoxia" one would get by ascending 300 meters in altitude (which typically does not produce tachycardia). With the $O_2$ concentration in the venous return staying the same, and the $O_2$ consumption staying the same, there is no place in the body where there is a reduction in $O_2$ concentration. Compensation during isovolemic anemia may not occur because of $O_2$ sensing.

Thus the vasodilatation that is observed in acute isovolemic anemia may be due to the increased NO concentration at the vessel wall. NO mediates dilatation of vessels in response to shear stress and other factors. No change in levels of NO metabolites would be observed, because the production rate of NO is unchanged and continues to equal the destruction rate. The observation of no "hypoxic" compensation with metHb substitution can be understood because metHb binds NO just as Hb does, so there is no NO concentration increase with metHb substitution as there is with Hb withdrawal.

Nitric oxide plays a role in many metabolic pathways. It has been suggested that a basal level of NO exerts a tonal inhibitory response, and that reduction of this basal level leads to a dis-inhibition of those pathways. Zanzinger et al. have reported that NO has been shown to inhibit basal sympathetic tone and attenuate excitatory reflexes. (Inhibition of basal and reflex-mediated sympathetic activity in the RVLM by nitric oxide. Am. J. Physiol. 268 (Regulatory Integrative Comp. Physiol. 37): R958-R962, 1995.)

In some aspects, it is appreciated that one component of a volume source of NO is low molecular weight S-nitrosothiols produced in the erythrocyte free skin from NO produced on the external skin by ammonia oxidizing bacteria. These low molecular weight S-nitrosothiols are stable for long periods, and can diffuse and circulate freely in the plasma. Various enzymes can cleave the NO from various S-nitrosothiols liberating NO at the enzyme site. It is the loss of this volume source of NO from AOB on the skin that leads to disruptions in normal physiology. The advantage to the body of using S-nitrosothiols to generate NO far from a capillary is that $O_2$ is not required for NO production from S-nitrosothiols. Production of NO from nitric oxide synthase (NOS) does require $O_2$. With a sufficient background of S-nitrosothiols, NO can be generated even in anoxic regions. Free NO is not needed either since NO only exerts effects when attached to another molecule, such as the thiol of a cysteine residue or the iron in a heme, so the effects of NO can be mediated by transnitrosation reactions even in the absence of free NO provided that S-nitrosothiols and transnitrosation enzymes are present.

Frank et al. have shown that the angiogenesis that accompanies normal wound healing is produced in part by elevated VEGF which is induced by increased nitric oxide. (Nitric oxide triggers enhanced induction of vascular endothelial growth factor expression in cultured keratinocytes (HaCaT) and during cutaneous wound repair. FASEB J. 13, 2002-2014 (1999).)

NO has a role in the development of cancer, indicating that the bacteria described herein may be used in methods of cancer treatment and prevention. According to certain aspects, it is appreciated that the presence of NO during hypoxia may prevent cells from dividing while under hypoxic stress, when cells are at greater risk for errors in copying DNA. One relevant cell function is the regulation of the cell cycle. This is the regulatory program which controls how and when the cell replicates DNA, assembles it into duplicate chromosomes, and divides. The regulation of the cell cycle is extremely complex, and is not fully understood. However, it is known that there are many points along the path of the cell cycle where the cycle can be arrested and division halted until conditions for doing so have improved. The p53 tumor suppressor protein is a key protein in the regulation of the cell cycle, and it serves to initiate both cell arrest and apoptosis from diverse cell stress signals including DNA damage and p53 is mutated in over half of human cancers as reported by Ashcroft et al. in "Stress Signals Utilize Multiple Pathways To Stabilize p53." (Molecular And Cellular Biology, May 2000, p. 3224-3233.) Hypoxia does initiate accumulation of p53, and while hypoxia is important in regulating the cell cycle, hypoxia alone fails to induce the downstream expression of p53 mRNA effector proteins and so fails to cause arrest of the cell cycle. Goda et al. have reported that hypoxic induction of cell arrest requires hypoxia-inducing factor-1 (HIF-1α). (Hypoxia-Inducible Factor 1α Is Essential for Cell Cycle Arrest during Hypoxia. Molecular And Cellular Biology, January 2003, p. 359-369.) Britta et al. have reported that NO is one of the main stimuli for HIF-1α. (Accumulation of HIF-1a under the influence of nitric oxide. Blood, 15 Feb. 2001, Volume 97, Number 4.) In contrast, NO does cause the accumulation of transcriptionally active p53 and does cause arrest of the cell cycle and does cause apoptosis. Wang et al., P53 Activation By Nitric Oxide Involves Down-Regulation Of Mdm2. THE JOURNAL OF BIOLOGICAL CHEMISTRY Vol. 277, No. 18, Issue Of May 3, Pp. 15697-15702, 2002.

In certain aspect of the disclosure, it is appreciated that preventing the necrotic death of cells by preventing the capillary rarefaction that leads to their hypoxic death may prevent autoimmune disorders. When cells are exposed to chronic hypoxia, the production of reactive oxygen species (ROS) is increased, and there is increased damage to the cells metabolic machinery and ultimately to the cells' DNA. Decreased metabolic capacity will decrease capacity for repair of damage due to ROS and due to exogenous carcinogen exposure. Over time, the damage accumulates and increases the chance of three events: the cell will undergo deletion of cancer-preventing genes and the cell will become cancerous, the cell will die through necrosis, or the cell will die through apoptosis. When cells die, either through necrosis or apoptosis, the cell debris must be cleared from the site. Dead cells are phagocytosed by immune cells, including dendritic cells and macrophages. When these cells phagocytose a body, it is digested by various proteolytic enzymes into antigenic fragments, and then these antigens are attached to the major histocompatability complex (MHC1, MHC2) and the antigen-MHC complex is moved to the surface of the cell where it can interact with T cells and activate the T cells in various ways. Any cell injury releases adjuvants which stimulate the immune system in various ways. In general, cells that undergo necrosis stimulate a greater immune response than cells that undergo apoptosis. Chronic exposure of immune cells to dead and dying cells is therefore likely to lead to autoimmune disorders.

In certain aspects, it is appreciated that low basal NO leads to fibrotic hypertrophy. Once a dead cell has been cleared, a new cell cannot easily take its place, because there is insufficient $O_2$ to support it. Any such new cell would suffer the same fate. The space can remain empty, in which case the organ shrinks, the capillaries draw closer together, new cells are now deprived of the VEGF formerly produced by the now-missing cell, so capillaries ablate and the hypoxic zone reforms. This could result in a general shrinkage of the affected tissues. In tissues that support fibrosis, relatively inert collagen fibers can fill the space. Since the metabolic requirements of the body for the particular organ in question are not reduced, the organ may attempt to grow larger, but now with a significant fibrous content. This may result in fibrotic hypertrophy, such as of the heart and liver. Some organs, such as the brain, cannot grow larger or smaller because the three-dimensional connectivity of nerves and blood vessels are important, and cannot be continuously and simultaneously mapped onto an asymmetrically shrinking brain. The space must be filled with something, and β-amyloid might be the (not so inert) space filler. The kidney cannot grow larger because of the renal capsule, so the number of living cells becomes smaller and they are replaced with fibrotic tissue. If the dead cells are cleared, the tissue shrinks, and the ratio of $NO/O_2$ goes down again, and the capillaries again become sparser. This may set up the vicious circle of end stage renal disease, congestive heart failure/cardiac hypertrophy, primary biliary cirrhosis, Alzheimer's disease, atherosclerosis, inflammatory bowel disease, hypertrophic scar formation, and the multiple connective tissue diseases starting with Raynaud's phenomena and ending with Systemic Sclerosis and primary Sjogren's syndrome where capillary rarefaction is also observed. Ferrini et al, have shown that a reduction in basal NO levels through chronic inhibition of NOS with L-NAME leads to generalized fibrosis of the heart and kidneys. (Antifibrotic Role of Inducible Nitric Oxide Synthase. Nitirc Oxide: Biology and Chemistry Vol. 6, No. 3, pp. 283-294 (2002).) It may be that low basal NO leads to fibrotic hypertrophy.

In certain aspects, it is appreciated that capillary rarefaction affects a subject's ability to control their appetite. Capillary rarefaction is observed in the brains of aged humans and animals. Capillary rarefaction is associated with declines in circulating growth factors including insulin like growth factor-1. Neurogenesis in the adult brain is coordinated with angiogenesis. Since the brain regulates many homeostatic functions, increased diffusion lengths between capillaries to control elements of the brain might be "interpreted" as inadequate blood concentrations of those species. The flux of glucose in the brain is quite close to normal metabolic needs, where glucose flux is only 50 to 75% greater than glucose consumption and the glucose transporters across the blood brain barrier are saturable, steriospecific and independent of energy or ion gradients. A large part of the regulation of appetite is mediated through the brain, and capillary rarefaction may cause an adequate blood concentration of "nutrients" (or marker compounds proportional to "nutrients") to be interpreted as insufficient. This may be one cause of obesity.

According to certain aspects, it is appreciated that capillary rarefaction may be a cause of non-insulin dependent diabetes. Non-insulin dependent diabetes (NIDDM) is also known as the Metabolic Syndrome or Diabetes type 2, and is characterized by insulin resistance. The sensitivity of the body to insulin is reduced, and insulin levels increase People with NIDDM have high blood glucose, high blood triglycerides, are typically obese, hypertensive, and typically have significant visceral fat.

Other symptoms accompany NIDDM, which may point to capillary rarefaction as the cause. In a study of 40 men, with and without NIDDM, obese (BMI 29) and lean (BMI 24) (10 of each), Konrad et al. report that blood lactate levels at rest were 1.78, 2.26, 2.42, and 2.76 (mM/L) for lean men without, obese men without, lean men with NIDDM, obese men with NIDDM respectively. (A-Lipoic acid treatment decreases serum lactate and pyruvate concentrations and improves glucose effectiveness in lean and obese patients with type 2 diabetes. Diabetes Care 22:280-287, 1999.) Lactate is a measure of anaerobic glycolysis. When $O_2$ is insufficient to generate ATP through oxidative phosphorylation, cells can produce ATP through anaerobic glycolysis.

One of the products of anaerobic glycolysis is lactate, which must be exported from the cells, otherwise the pH drops and function is compromised. Blood lactate is commonly measured in exercise studies, where an increase indicates the work load at which maximum oxidative work can be done. Higher levels of lactate at rest would indicate increased anaerobic glycolysis at rest, which is consistent with capillary rarefaction.

Primary biliary cirrhosis is associated with Raynaud's phenomena, pruritus, sicca syndrome, osteoporosis, portal hypertension, neuropathy, and pancreatic insufficiency, and liver abnormalities are associated with rheumatic diseases. Elevated liver enzymes are a symptom of liver inflammation, and elevated liver enzymes are observed as an early symptom of "asymptomatic" primary biliary cirrhosis. Accordingly, the bacteria described herein may be used to treat liver inflammation.

Tone et al have reported that Alzheimer's disease (AD) is a microvascular disorder with neurological degeneration secondary to hypoperfusion, resulting in part from insufficient nitric oxide. (Review: Evidence that Alzheimer's disease is a microvascular disorder: the role of constitutive nitric oxide, Brain Research Reviews 34 (2000) 119-136.) Accordingly, the bacteria described herein may be used to treat AD.

Adverse health effects that are associated with hypertension may also be consequences of low basal NO. The decreased response to vasodilatation is also consistent with low basal NO. NO is a diffusible molecule that diffuses from a source to a sensor site where it has the signaling effect. With low NO levels, every NO source must produce more NO to generate an equivalent NO signal of a certain intensity a certain distance away. NO diffuses in three dimensions and the whole volume within that diffusion range must be raised to the level that will give the proper signal at the sensor location. This may result in higher NO levels at the source and between the source and the sensor. Adverse local effects of elevated NO near a source may then arise from too low a NO background. There is some evidence that this scenario actual occurs. In rat pancreatic islets, Henningsson et al have reported that inhibition of NOS with L-NAME increases total NO production through the induction of iNOS. (Chronic blockade of NO synthase paradoxically increases islet NO production and modulates islet hormone release. Am J Physiol Endocrinol Metab 279: E95-E107, 2000.) Increasing NO by increasing NOS activity will only work up to some limit. When NOS is activated but is not supplied with sufficient tetrahydrobiopterin (BH4) or L-arginine, it becomes "uncoupled" and generates superoxide (O2-) instead of NO. This $O_2^-$ may then destroy NO. Attempting to produce NO at a rate that exceeds the supply of BH4 or L-arginine may instead decrease NO levels. This may result in positive feedback where low NO levels are made worse by stimulation of NOS, and uncoupled NOS generates significant $O_2^-$ which causes local reactive oxygen species (ROS) damage such as is observed in atherosclerosis, end stage renal disease, Alzheimer's, and diabetes.

The bacteria described herein may also be used to delay the signs of aging. Caloric restriction extends lifespan, and Holloszy reported that restricting food intake to 70% of ad lib controls, prolongs life in sedentary rats from 858 to 1,051 days, almost 25%. (Mortality rate and longevity of food restricted exercising male rats: a reevaluation. J. Appl. Physiol. 82(2): 399-403, 1997.) The link between calorie restriction and prolonged life is well established, however, the causal mechanism is not. Lopez-Tones et al. reported that the examination of liver mitochondrial enzymes in rats indicates a reduction in $H_2O_2$ production due to reduced complex I activity associated with calorie restriction. (Influence Of Aging And Long-Term Caloric Restriction On Oxygen Radical Generation And Oxidative DNA Damage In Rat Liver Mitochondria. Free Radical Biology & Medicine Vol. 32 No 9 pp 882-8899, 2002.) $H_2O_2$ is produced by dismutation of $O_2^-$, which is a major ROS produced by the mitochondria during respiration. The main source of $O_2^-$ has been suggested by Kushareva et al. and others to be complex I which catalyzes the NAD/NADH redox couple by reverse flow of electrons from complex III, the site of succinate reduction. The free radical theory, proposed by Beckman, of aging postulates, that free radical damage to cellular DNA, antioxidant systems and DNA repair systems accumulates with age and when critical systems are damaged beyond repair, death ensues. (The Free Radical Theory of Aging Matures. Physiol. Rev. 78: 547-581, 1998.)

As an additional mechanism, NO has been demonstrated by Vasa et al. to activate telomerase and to delay senescence of endothelial cells. (Nitric Oxide Activates Telomerase and Delays Endothelial Cell Senescence. Circ Res. 2000; 87:540-542.) Low basal NO will increase basal metabolic rate by disinhibition of cytochrome oxidase. Increased basal metabolism will also increase cell turn-over and growth rate. Capillary rarefaction, by inducing chronic hypoxia may increase free radical damage and may also increase cell turn-over, and so accelerate aging by both mechanisms.

In some aspects, it is appreciated that autotrophic ammonia-oxidizing bacteria may produce protective aspects for allergies and autoimmune disorders. The best known autoimmune disease is perhaps Diabetes Type 1, which results from the destruction of the insulin producing cells in the pancreas by the immune system. Recurrent pregnancy loss is also associated with autoimmune disorders where the number of positive autoimmune antibodies correlated positively with numbers recurrent pregnancy losses. Systemic Sclerosis, Primary Biliary Cirrhosis, autoimmune hepatitis, and the various rheumatic disorders are other examples of autoimmune disorders. Application of AOB was observed to reduce an allergy, hay fever, as described in WO/2005/030147.

One mechanism by which AOB may exert their protective effect on allergies and autoimmune disorders is through the production of nitric oxide, primarily through the regulatory inhibition of NF-$\kappa$B and the prevention of activation of immune cells and the induction of inflammatory reactions. NF-$\kappa$B is a transcription factor that up-regulates gene expression and many of these genes are associated with inflammation and the immune response including genes which cause the release of cytokines, chemokines, and various adhesion factors. These various immune factors cause the migration of immune cells to the site of their release resulting in the inflammation response. Constitutive NO production has been shown to inhibit NF-$\kappa$B by stabilizing I$\kappa$B$\alpha$ (an inhibitor of NF-KB) by preventing IKB$\alpha$ degradation.

Administration of an NO donor has been shown by Xu et al. to prevent the development of experimental allergic encephalomyelitis in rats. (SIN-1, a Nitric Oxide Donor, Ameliorates Experimental Allergic Encephalomyelitis in Lewis Rats in the Incipient Phase: The Importance of the Time Window. The Journal of Immunology, 2001, 166: 5810-5816.) In this study, it was demonstrated that administering an NO donor, reduced the infiltration of macrophages into the central nervous system, reduced the proliferation of blood mononuclear cells, and increased apoptosis of blood mononuclear cells. All of these results are expected to reduce the extent and severity of the induced autoimmune response.

Low basal NO may lead to autism via the mechanism that new connections in the brain are insufficiently formed as a result of insufficient basal nitric oxide. While not wishing to be bound in theory, in some embodiments, formation of neural connections is modulated by NO. In these cases, any condition that lowers the range of NO diffusion may decrease the volume size of brain elements that can undergo connections. A brain which developed under conditions of low basal NO levels may be arranged in smaller volume elements because the reduced effective range of NO.

Additional symptoms exhibited in autistic individuals may also point to low NO as a cause, including increased pitch discrimination, gut disturbances, immune system dysfunction, reduced cerebral blood flow, increased glucose consumption of the brain, increased plasma lactate, attachment disorders, and humming. Each of these symptoms may be attributed to a low basal NO level.

Takashi Ohnishi et al. have reported that autistic individuals show decreased blood flow. Takashi Ohnishi et al., Abnormal regional cerebral blood flow in childhood autism. Brain (2000), 123, 1838-1844. J. M. Rumsey et al. have reported that autistic individuals have increased glucose consumption. Rumsey J M, Duara R, Grady C, Rapoport J L, Margolin R A, Rapoport S I, Cutler N R. Brain metabolism in autism. Resting cerebral glucose utilization rates as measured with positron emission tomography. Arch Gen Psychiatry, 1985 May; 42(5):448-55 (abstract). D. C. Chugani has reported that autistic individuals have an increased plasma lactate levels. Chugani D C, et al., Evidence of altered energy metabolism in autistic children. Prog Neuropsychopharmacol Biol Psychiatry. 1999 May; 23(4): 635-41. The occurrence of these effects may be a result of capillary rarefaction in the brain, which may reduce blood flow and $O_2$ supply, such that some of the metabolic load of the brain may be produced through glycolysis instead of oxidative phosphorylation.

Nitric oxide has been demonstrated by B. A. Klyachko et al. to increase the excitability of neurons by increasing the after hyperpolarization through cGMP modification of ion channels. Vitaly A. Klyachko et al., cGMP-mediated facilitation in nerve terminals by enhancement of the spike after hyperpolarization. Neuron, Vol. 31, 1015-1025, Sep. 27, 2001. C. Sandie et al. have shown that inhibition of NOS reduces startle. Carmen Sandi et al., Decreased spontaneous motor activity and startle response in nitric oxide synthase inhibitor-treated rats. European journal of pharmacology 277 (1995) 89-97. Attention-Deficit Hyperactivity Disorder (ADHD) has been modeled using the spontaneously hypertensive rat (SHR) and the Naples high-excitability (NHE) rat. Both of these models have been shown by Raffaele Aspide et al, to show increased attention deficits during periods of acute NOS inhibition. Raffaele Aspide et al., Non-selective attention and nitric oxide in putative animal models of attention-deficit hyperactivity disorder. Behavioral Brain Research 95 (1998) 123-133. Accordingly, the bacteria herein may be used in the treatment of ADHD.

Inhibition of NOS has also been shown by M. R. Dzoljic to inhibit sleep. M. R. Dzoljic, R. de Vries, R. van Leeuwen. Sleep and nitric oxide: effects of 7-nitro indazole, inhibitor of brain nitric oxide synthase. Brain Research 718 (1996) 145-150. G. Zoccoli has reported that a number of the physiological effects seen during sleep are altered when NOS is inhibited, including rapid eye movement and sleep-wake differences in cerebral circulation. G. Zoccoli, et al., Nitric oxide inhibition abolishes sleep-wake differences in cerebral circulation. Am. J. Physiol. Heart Circ Physiol 280: H2598-2606, 2001. NO donors have been shown by L. Kapas et al. to promote non-REM sleep, however, these increases persisted much longer than the persistence of the NO donor, suggesting perhaps a rebound effect. Levente Kapas et al. Nitric oxide donors SIN-1 and SNAP promote nonrapid-eye-movement sleep in rats. Brain Research Bullitin, vol 41, No 5, pp. 293-298, 1996. M. Rosaria et al., Central NO facilitates both penile erection and yawning. Maria Rosaria Melis and Antonio Argiolas. Role of central nitric oxide in the control of penile erection and yawning. Prog Neuro-Psychopharmacol & Biol. Phychiat. 1997, vol 21, pp 899-922. P. Tani et al, have reported that insomnia is a frequent finding in adults with Asperger's. Pekka Tani et al., Insomnia is a frequent finding in adults with Asperger's syndrome. BMC Psychiatry 2003, 3:12. Y. Hoshino has also observed sleep disturbances in autistic children. Hoshino Y, Watanabe H, Yashima Y, Kaneko M, Kumashiro H. An investigation on sleep disturbance of autistic children. Folia Psychiatr Neurol Jpn. 1984; 38(1):45-51. (abstract) K. A. Schreck et al. has observed that the severity of sleep disturbances correlates with severity of autistic symptoms. Schreck K A, et al., Sleep problems as possible predictors of intensified symptoms of autism. Res Dev Disabil. 2004 January-February; 25(1):57-66. (abstract). Accordingly, the bacteria herein may be used in the treatment of insomnia.

W. D. Ratnasooriya et al reported that inhibition of NOS in male rats reduces pre-coital activity, reduces libido, and reduces fertility. W. D. Ratnasooriya et al., Reduction in libido and fertility of male rats by administration of the nitric oxide (NO) synthase inhibitor N-nitro-L-arginine methyl ester. International journal of andrology, 23: 187-191 (2000).

It may be that a number of seemingly disparate disorders, characterized by ATP depletion and eventual organ failure are actually "caused" by nitropenia, caused by a global deficiency in basal nitric oxide. When this occurs in the heart, the result is dilative cardiomyopathy. When this occurs in the brain, the result is white matter hyperintensity, Alzheimer's, vascular depression, vascular dementia, Parkinson's, and the Lewy body dementias. When this occurs in the kidney, the result is end stage renal disease, when this occurs in the liver, the result is primary biliary cirrhosis. When this occurs in muscle, the consequence is fibromyaligia, Gulf War Syndrome, or chronic fatigue syndrome. When this occurs in the bowel, the consequence is ischemic bowel disease. When this occurs in the pancreas, the consequence is first type 2 diabetes, followed by chronic inflammation of the pancreas, followed by autoimmune attack of the pancreas (or pancreatic cancer), followed by type 1 diabetes. When this occurs in the connective tissue, the consequence is systemic sclerosis.

In the remnant kidney model of end stage renal disease, part of the kidney is removed, (either surgically or with a toxin) which increases the metabolic load on the remainder. Superoxide is generated to decrease NO and increase $O_2$ diffusion to the kidney mitochondria. Chronic overload results in progressive kidney capillary rarefaction and progressive kidney failure. In acute kidney failure, putting people in dialysis can give the kidney a "rest", and allows it to recover. In acute renal failure induced by rhabdomyolysis (muscle damage which releases myoglobin into the blood stream) kidney damage is characterized by ischemic damage. Myoglobin scavenges NO, just as hemoglobin does, and would cause vasoconstriction in the kidney leading to ischemia. Myoglobin would also induce local nitropenia and the cascade of events leading to further ATP depletion.

In some aspects, low NO levels lead to reduced mitochondrial biogenesis. Producing the same ATP at a reduced mitochondria density will result in an increase in $O_2$ consumption, or an accelerated basal metabolic rate. An accelerated basal metabolic rate is observed in a number of conditions, including: Sickle cell anemia, Congestive heart failure, Diabetes, Liver Cirrhosis, Crohn's disease, Amyotrophic lateral sclerosis, Obesity, End stage renal disease, Alzheimer's, and chronic obstructive pulmonary disease.

While some increased $O_2$ consumption might be productively used, in many of these conditions uncoupling protein is also up-regulated, indicating that at least part of the increased metabolic rate is due to inefficiency. Conditions where uncoupling protein is known to be up-regulated include obesity and diabetes.

With fewer mitochondria consuming $O_2$ to a lower $O_2$ concentration, the $O_2$ gradient driving $O_2$ diffusion is greater, so the $O_2$ diffusion path length can increase resulting in capillary rarefaction, which is observed in dilative cardiomyopathy, hypertension, diabetes type 2, and renal hypertension.

Copper, either as Cu2+ or as ceruloplasmin (CP) (the main Cu containing serum protein which is present at 0.38 g/L in adult sera and which is 0.32% Cu and contains 94% of the serum copper) catalyzes the formation of S—NO-thiols from NO and thiol containing groups (RSH). The Cu content of plasma is variable and is increased under conditions of infection. Berger et al. reported that the Cu and Zn content of burn-wound exudates is considerable with patients with ⅓ of their skin burned, losing 20 to 40% of normal body Cu and 5 to 10% of Zn content in 7 days. (Cutaneous copper and zinc losses in burns. Burns. 1992 October; 18(5):373-80.) If the patients skin were colonized by AOB, wound exudates which contains urea and Fe, Cu, and Zn that AOB need, would be converted into NO and nitrite, greatly supplementing the local production of NO by iNOS, without consuming resources (such as $O_2$ and L-arginine) in the metabolically challenged wound. A high production of NO and nitrite by AOB on the surface of a wound would be expected to inhibit infection, especially by anaerobic bacteria such as the Clostridia which cause tetanus, gas gangrene, and botulism.

The practice of the present disclosure may employ, unless otherwise indicated, conventional methods of immunology, molecular biology, and recombinant DNA techniques within the skill of the art. Such techniques are explained fully in the literature. See, e.g., Sambrook, et al. Molecular Cloning: A Laboratory Manual (Current Edition); and Current Protocols in Molecular Biology (F. M. Ausubel, et al. eds., current edition).

EXAMPLES

Surfactant Experiments

For the purposes of these experiments a 1× *N. eutropha* D23 cell refers to $10^9$ CFU/ml. Thus, it follows that a 0.1× *N. eutropha* D23 cells is $0.1×10^9$ CFU/ml and 0.001 1× *N. eutropha* D23 cells is $0.001×10^9$ CFU/ml/

Recovery of *N. Eutropha* D23 Cells After Incubation of $10^9$ CFU/ml Cells (1×) with Cola®Terric COAB Surfactant for Different Time Periods.

1× *N. eutropha* D23 cells were incubated in 10 ml ammonia oxidizing bacteria (AOB) media containing 0%, 0.01%, 0.1% & 1% non-ionic surfactant Cola®Terric. Samples of 1 ml were taken at the end of 1 minute, 10 minutes, 60 minutes, and 1 day incubations. Samples were centrifuged, and the supernatant was used for nitrite measurements.

Figure 9A:
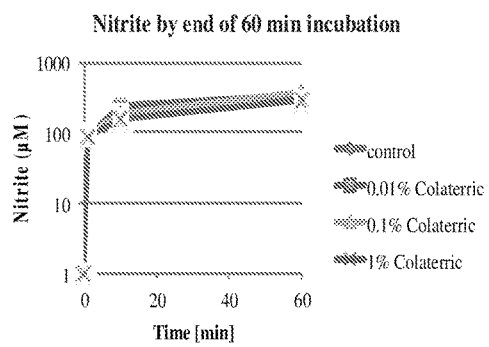
FIG. 9A shows the nitrite production of *N. eutropha* D23 with various concentrations of Cola®Terric COAB. The nitrite concentration is plotted relative to time.
Figure 9B:
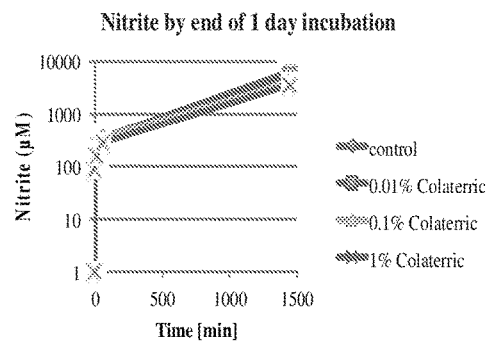
FIG. 9B shows the nitrite production of *N. eutropha* D23 with various concentrations of Cola®Terric COAB. The nitrite concentration is plotted relative to time.
Figure 9C:
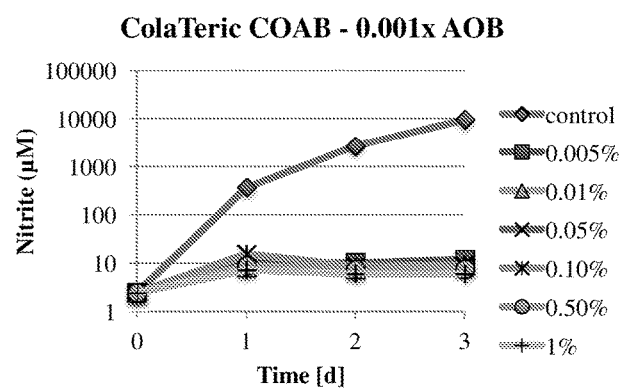
FIG. 9C shows the nitrite production of *N. eutropha* D23 with various concentrations of Cola®Terric COAB. The nitrite concentration is plotted relative to time.
Figure 9D:
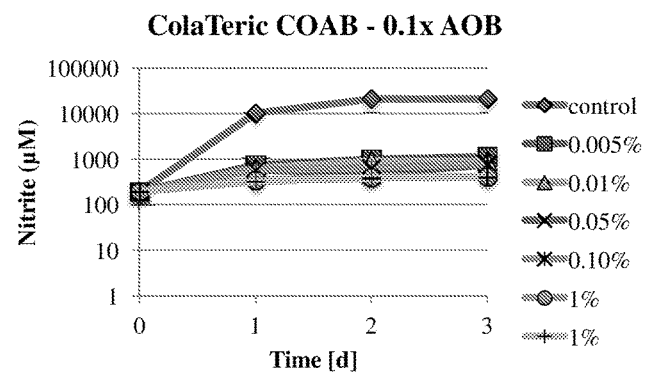
FIG. 9D shows the nitrite production of *N. eutropha* D23 with various concentrations of Cola®Terric COAB. The nitrite concentration is plotted relative to time.
Figure 10A:
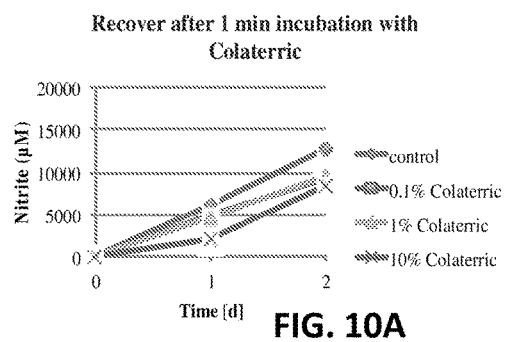
FIG. 10A shows the nitrite production of *N. eutropha* D23 after incubation with Cola®Terric COAB. The nitrite concentration is plotted relative to time.
Figure 10B:
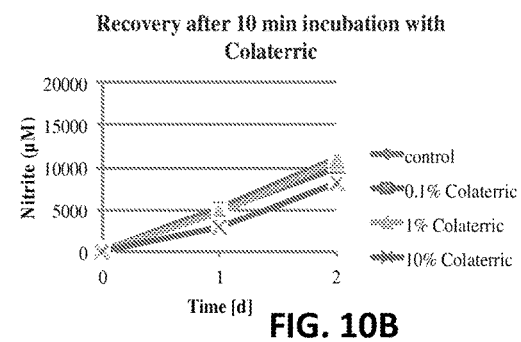
FIG. 10B shows the nitrite production of *N. eutropha* D23 after incubation with Cola®Terric COAB. The nitrite concentration is plotted relative to time.
Figure 10C:
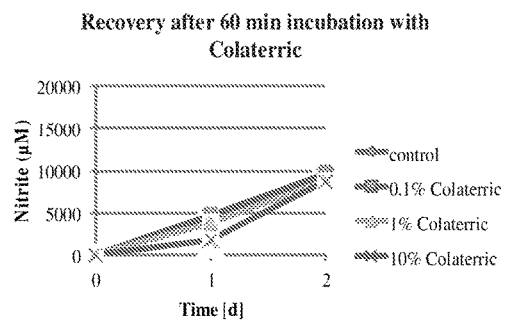
FIG. 10C shows the nitrite production of *N. eutropha* D23 after incubation with Cola®Terric COAB. The nitrite concentration is plotted relative to time.
Figure 10D:
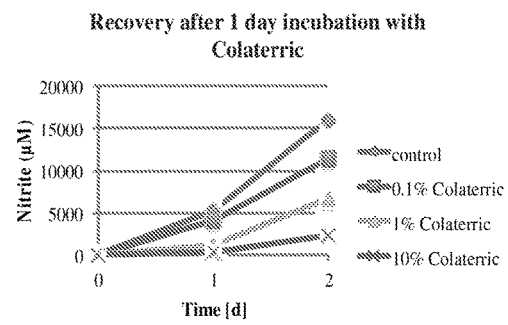
FIG. 10D shows the nitrite production of *N. eutropha* D23 after incubation with Cola®Terric COAB. The nitrite concentration is plotted relative to time.

As shown in FIGS. 9A and 9B, nitrite accumulation was observed in the presence of 0.01%, 0.11%, and 1% Cola®Terric. As shown in FIGS. 9C and 9D, longer incubations with 0.001× ammonia oxidizing bacteria, and 0.1× ammonia oxidizing bacteria resulted in less nitrite accumulation as compared to a control.

Cell pellets obtained after centrifugation were washed once with AOB media and suspended in 10 ml fresh AOB media containing 50 mM $NH_4^+$. Recovery of *N. eutropha* D23 cells was studies by measuring nitrites.

As shown in FIGS. 10A-10D, *N. eutropha* D23 cells incubated with 0.1% to 10% Cola®Terric for up to 60 minutes recovered similar to *N. eutropha* D23 control cells. *N. eutropha* D23 cells incubated with 1% and 10% Cola®Terric for 1 day recovered slower compared to *N. eutropha* D23 control cells.

Recovery of *N. Eutropha* D23 Cells After Incubation of 1× Cells with Dr. Bronner's Castille Soap (0.1-10%) for Different Time Periods.

*N. eutropha* D23 incubations with, and recovery from, Dr. Bronner's Castille Soap ("Dr. Bronner's") were done as indicated above with regard to the Cola®Terrric surfactant.

Figure 11A:
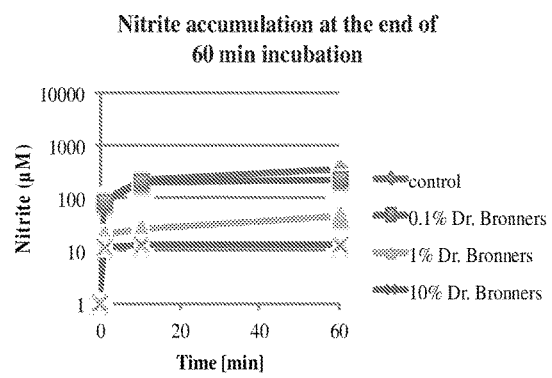
FIG. 11A shows the nitrite production of *N. eutropha* D23 with various concentrations of Dr. Bronner's Castille soap. The nitrite concentration is plotted relative to time.
Figure 11B:
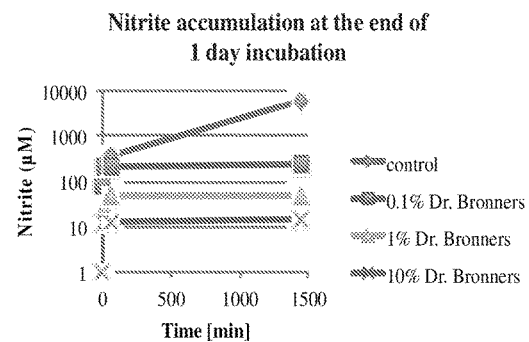
FIG. 11B shows the nitrite production of *N. eutropha* D23 with various concentrations of Dr. Bronner's Castille soap. The nitrite concentration is plotted relative to time.

As shown in FIGS. 11A through 12D, nitrite accumulation data during incubation with Dr. Bronner's and during recovery from Dr. Bronner's was measured. As shown in FIGS. 11A and 11B, nitrite accumulation was reduced by the presence of Dr. Bronner's at the end of 60 minutes for the 1% and 10% Dr. Bronner's samples. After 60 minutes, there appeared to be very little, if any reduction in nitrite accumulation for the 0.1% sample when compared to the control. After 1 day, each sample containing Dr. Bronner's did not have as high of a nitrite accumulation as the control.

Figure 12A:
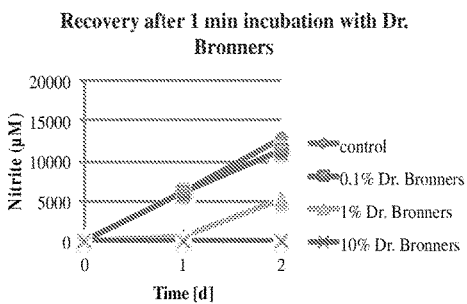
FIG. 12A shows the nitrite production of *N. eutropha* D23 after incubation with Dr. Bronner's Castille soap. The nitrite concentration is plotted relative to time.
Figure 12B:
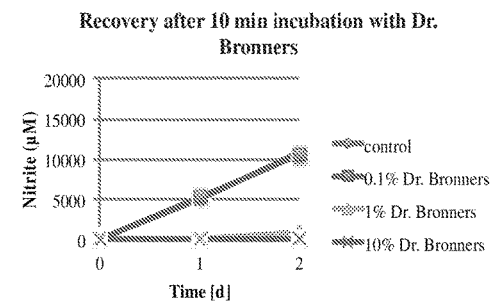
FIG. 12B shows the nitrite production of *N. eutropha* D23 after incubation with Dr. Bronner's Castille soap. The nitrite concentration is plotted relative to time.
Figure 12C:
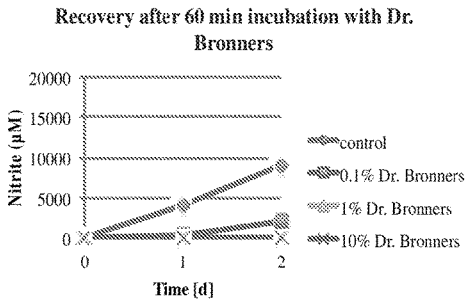
FIG. 12C shows the nitrite production of *N. eutropha* D23 after incubation with Dr. Bronner's Castille soap. The nitrite concentration is plotted relative to time.
Figure 12D:
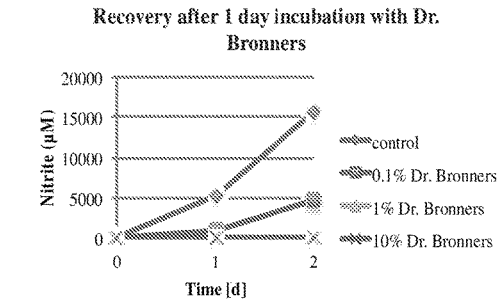
FIG. 12D shows the nitrite production of *N. eutropha* D23 after incubation with Dr. Bronner's Castille soap. The nitrite concentration is plotted relative to time.
Figure 13A:
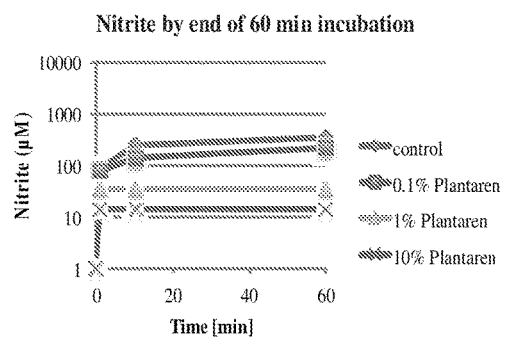
FIG. 13A shows the nitrite production of *N. eutropha* D23 with various concentrations of Plantaren 2000 N UP. The nitrite concentration is plotted relative to time.
Figure 13B:
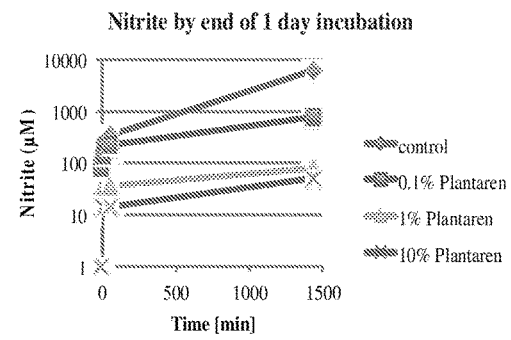
FIG. 13B shows the nitrite production of *N. eutropha* D23 with various concentrations of Plantaren 2000 N UP. The nitrite concentration is plotted relative to time.

As shown in FIGS. 12A and 12B, recovery after a 1 minute and a 10 minute incubation with Dr. Bronners Castille soap allowed comparable recovery as the control for the sample in 0.1% Dr. Bronners. After 60 minutes and 1 day, as shown in FIGS. 13A and 13B, the recovery of this sample decreased. For the samples containing higher concentrations of Dr. Bronner's (1% and 10%), recovery was either not as high or not possible at 1 minute, 10 minute, 60 minute, and 1 day incubations.

Recovery of *N. Eutropha* D23 Cells After Incubation of 1× Cells with Plantaren 2000 N UP (0.1-1%) for Different Time Periods.

*N. eutropha* D23 incubations with and recovery from Plantaren 2000 N UP ("Plantaren") were done as indicated above with regard to the Cola®Terrric surfactant. Nitrite accumulation data during incubation with Plantaren and during recovery from Plantaren are shown in FIGS. 13A-13B and FIGS. 14A-14D.

As shown in FIGS. 13A and 13B, nitrite accumulation was reduced as compared to the control by the presence of Plantaren at the end of 60 minutes for the 1% and 10% Plantaren samples, and there was a very minimal reduction in nitrite accumulation in the 0.1% sample. After 1 day, each sample containing Plantaren did not have as high of a nitrite accumulation as the control.

Figure 14A:
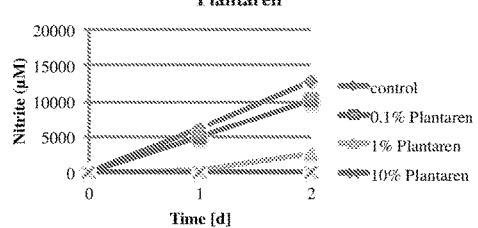
FIG. 14A shows the nitrite production of *N. eutropha* D23 after incubation with Plantaren 2000 N UP. The nitrite concentration is plotted relative to time.
Figure 14B:
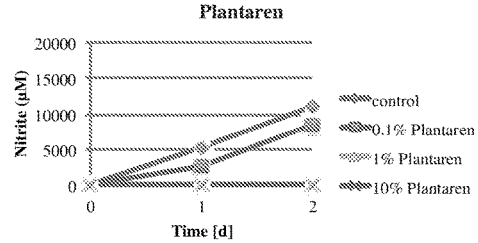
FIG. 14B shows the nitrite production of *N. eutropha* D23 after incubation with Plantaren 2000 N UP. The nitrite concentration is plotted relative to time.
Figure 14C:
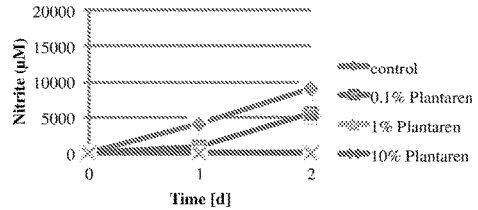
FIG. 14C shows the nitrite production of *N. eutropha* D23 after incubation with Plantaren 2000 N UP. The nitrite concentration is plotted relative to time.
Figure 14D:
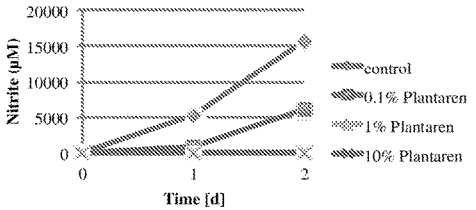
FIG. 14D shows the nitrite production of *N. eutropha* D23 after incubation with Plantaren 2000 N UP. The nitrite concentration is plotted relative to time.

As shown in FIGS. 14A and 14B, recovery after a 1 minute and a 10 minute incubation with Plantaren allowed only a slight reduction in recovery as compared to the control for the sample in 0.1% Plantaren. After 60 minutes and 1 day, shown in FIGS. 14C and 14D, the recovery of this sample decreased. For the samples containing higher concentrations of Plantaren (1% and 10%), recovery was either not as high or not possible at 1 minute, 10 minute, 60 minute, and 1 day incubations.

Figure 15A:
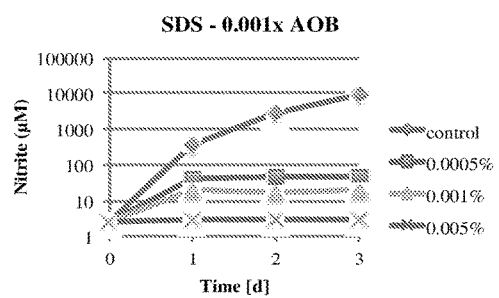
FIG. 15A shows the nitrite production of *N. eutropha* D23 with various concentrations of Sodium Dodecyl Sulfate. The nitrite concentration is plotted relative to time.
Figure 15B:
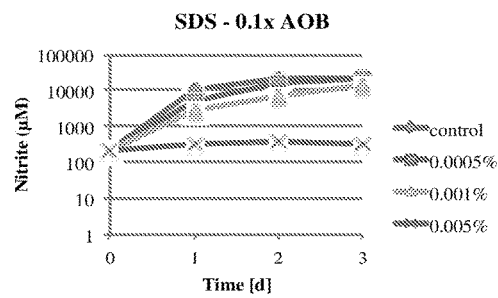
FIG. 15B shows the nitrite production of *N. eutropha* D23 with various concentrations of Sodium Dodecyl Sulfate. The nitrite concentration is plotted relative to time.

*N. Eutropha* D23 Cultures in Various Concentrations of SDS and Other Surfactants Two different densities of *N. eutropha* D23 cells (0.001× and 0.1×) were incubated in various concentrations of surfactants: Plantapon 611 L UP (FIGS. 21C-21D), Stepanol WA-Extra K (FIGS. 19C-19D), Tween 80 (FIGS. 23A-23B) ColaLux LO (FIGS. 24A-24B), Plantaren 200 (FIGS. 25A-25B), RhodaSurf 6 (FIGS. 26A-26B), ColaTerric COAB (FIGS. 9C and 9D), and SDS (FIGS. 15A-15B).

Cell densities of 0.001× and 0.1× cell represent the *N. eutropha* D23 cell densities at the beginning and end of a batch culture experiment. Except for incubation with Tween 80 (FIGS. 23A-23B), there is very little nitrite accumulation when 0.001× *N. eutropha* D23 cell densities were incubated with 6 different surfactants (Plantapon 611 L UP (FIGS. 21C-21D), Stepanol WA-Extra K (FIGS. 19C-19D), Tween 80 (FIGS. 23A-23B) ColaLux LO (FIGS. 24A-24B), Plantaren 200 (FIGS. 25A-25B), RhodaSurf 6 (FIGS. 26A-26B)).

Figure 16A:
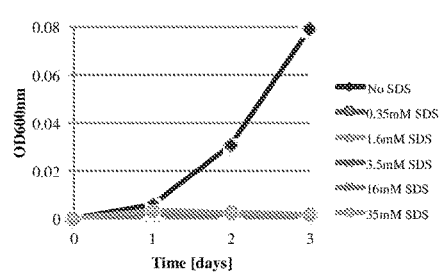
FIG. 16A shows the OD600 of *N. eutropha* D23 after incubation with Sodium Dodecyl Sulfate. The OD600 is plotted relative to time.
Figure 16B:
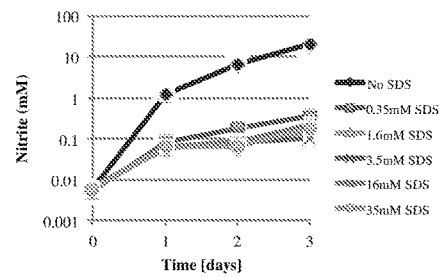
FIG. 16B shows the nitrite production of *N. eutropha* D23 after incubation with Sodium Dodecyl Sulfate. The nitrite concentration is plotted relative to time.

Increase in nitrite accumulation was observed when 0.1× cell densities were incubated with Tween 80, ColaLux and Stepanol WA-Extra K. Incubation of 0.001× cell densities with 0.01% to 1% (0.35 mM to 35 mM) SDS resulted in no increase in nitrite. Incubation of both 0.001× and 0.1× cell densities in the presence of 0.0005% to 0.005% SDS resulted in nitrite accumulation at lower SDS concentrations with 0.1× cell densities, as shown in FIGS. 15A and 15B. FIGS. 16A and 16B show the response of *N. eutropha* D23 to various concentrations of SDS depicted in plots of OD600 nm versus time and nitrite versus time.

Recovery of *N. Eutropha* D23 Cells After Incubation of 1× Cells with PolySufanate 160P Surfactant for Different Time Periods

Figure 17A:
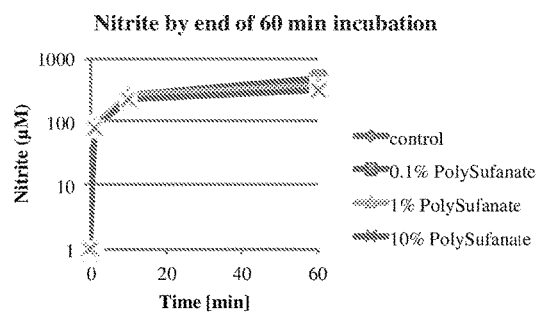
FIG. 17A shows the nitrite production of *N. eutropha* D23 with various concentrations of PolySufanate 160P. The nitrite concentration is plotted relative to time.
Figure 17B:
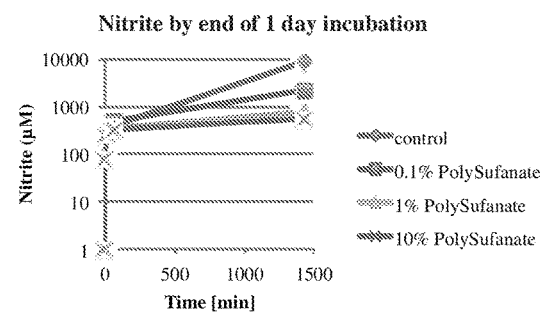
FIG. 17B shows the nitrite production of *N. eutropha* D23 with various concentrations of PolySufanate 160P. The nitrite concentration is plotted relative to time.
Figure 18A:
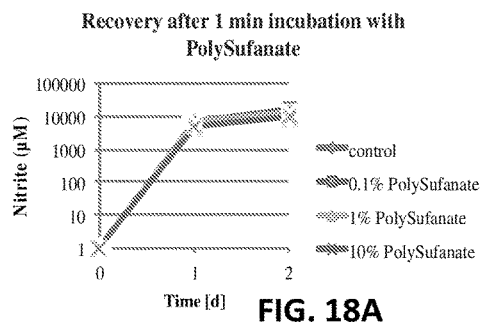
FIG. 18A shows the nitrite production of *N. eutropha* D23 after incubation with PolySufanate 160P. The nitrite concentration is plotted relative to time.
Figure 18B:
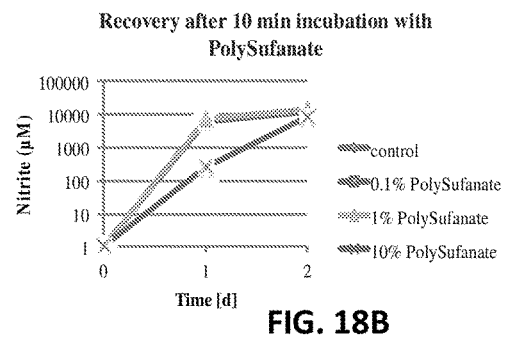
FIG. 18B shows the nitrite production of *N. eutropha* D23 after incubation with PolySufanate 160P. The nitrite concentration is plotted relative to time.
Figure 18C:
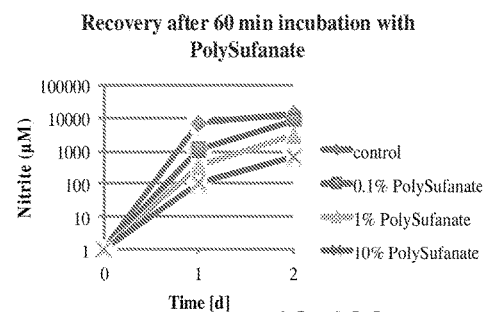
FIG. 18C shows the nitrite production of *N. eutropha* D23 after incubation with PolySufanate 160P. The nitrite concentration is plotted relative to time.
Figure 18D:
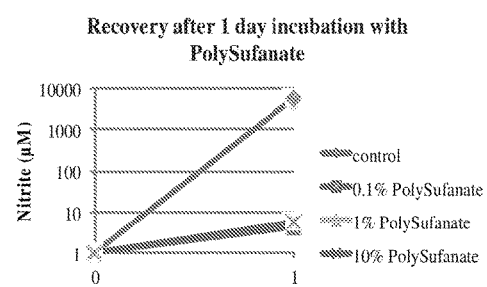
FIG. 18D shows the nitrite production of *N. eutropha* D23 after incubation with PolySufanate 160P. The nitrite concentration is plotted relative to time.

*N. eutropha* D23 cells were incubated in 10 ml ammonia oxidizing bacteria media containing 0%, 0.1%, 1%, and 10% surfactant PolySufanate 160P. Samples of 1 ml were taken at the end of 1 minunte, 10 minutes, 60 minutes, and 1 day incubations. Samples were centrifuged, and the supernatant was used for nitrite measurements. As shown in FIGS. 17A and 17B, nitrite accumulation was observed in the presence of 0.1%, 1%, and 10% PolySufanate. Cell pellets obtained after centrifugation were washed once with ammonia oxidizing bacteria media and suspended in 10 ml fresh media containing 50 mM $NH_4^+$. Recovery of *N. eutropha* D23 cells was studied by measuring nitrites. As shown in FIGS. 18A-18D, recovery was achieved after 1 minute, 10 minutes, and 60 minutes, as compared to the control. Very little recovery was achieved after 1 day, as compared to the control.

Recovery of *N. Eutropha* D23 Cells After Incubation of 1× Cells with Stepanol WA-Extra K (0.1-10%) Surfactant for Different Time Periods

Figure 19A:
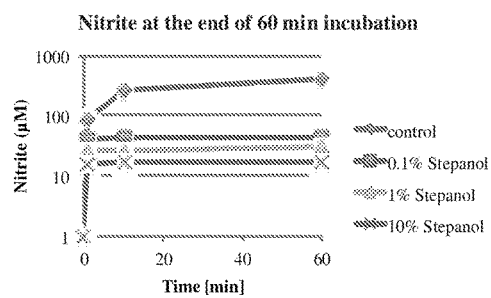
FIG. 19A shows the nitrite production of *N. eutropha* D23 with various concentrations of Stepanol WA-Extra K. The nitrite concentration is plotted relative to time.
Figure 19B:
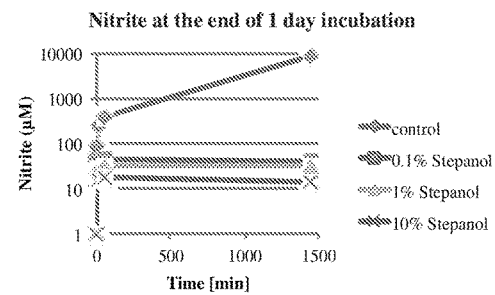
FIG. 19B shows the nitrite production of *N. eutropha* D23 with various concentrations of Stepanol WA-Extra K. The nitrite concentration is plotted relative to time.
Figure 19C:
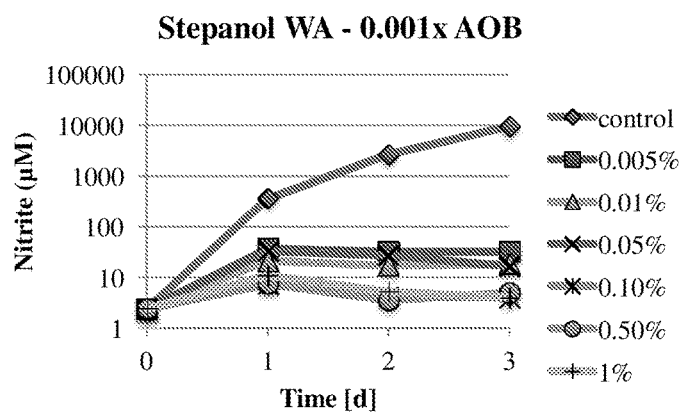
FIG. 19C shows the nitrite production of *N. eutropha* D23 with various concentrations of Stepanol WA-Extra K. The nitrite concentration is plotted relative to time.
Figure 19D:
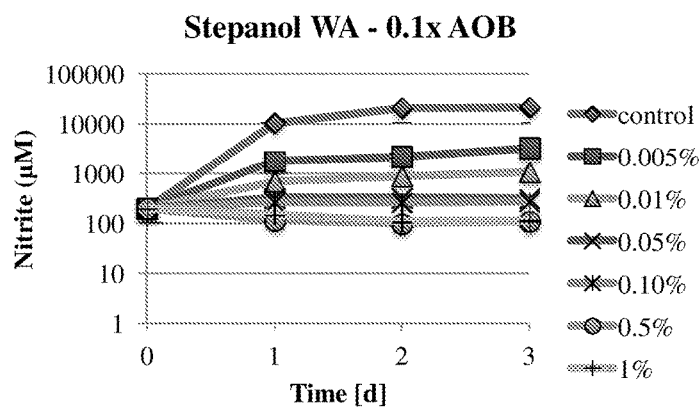
FIG. 19D shows the nitrite production of *N. eutropha* D23 with various concentrations of Stepanol WA-Extra K. The nitrite concentration is plotted relative to time.
Figure 20A:
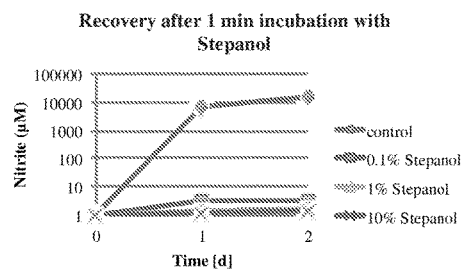
FIG. 20A shows the nitrite production of *N. eutropha* D23 after incubation with Stepanol WA-Extra K. The nitrite concentration is plotted relative to time.
Figure 20B:
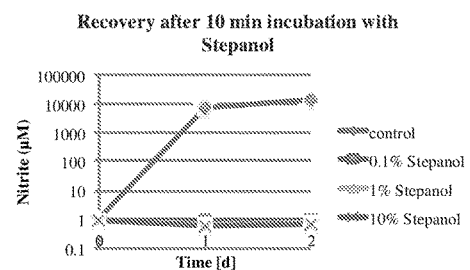
FIG. 20B shows the nitrite production of *N. eutropha* D23 after incubation with Stepanol WA-Extra K. The nitrite concentration is plotted relative to time.
Figure 20C:
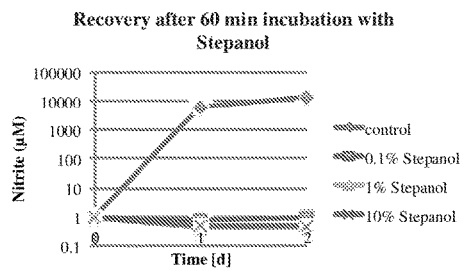
FIG. 20C shows the nitrite production of *N. eutropha* D23 after incubation with Stepanol WA-Extra K. The nitrite concentration is plotted relative to time.
Figure 20D:
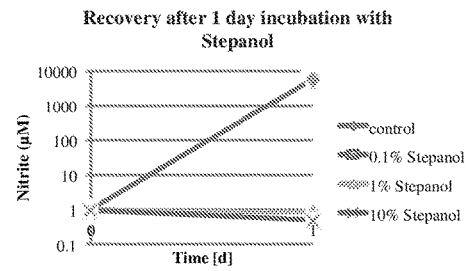
FIG. 20D shows the nitrite production of *N. eutropha* D23 after incubation with Stepanol WA-Extra K. The nitrite concentration is plotted relative to time.

*N. eutropha* D23 cells were incubated with and recovered from Stepanol WA-Extra K surfactant were done as indicated above with regard to PolySufanate 160P. Nitrite accumulation data during incubation with Stepanol are shown in FIGS. 19A-19B. All samples with surfactant did not accumulate nitrite at the same levels as the control sample at 60 minutes and 1 day of incubation, as well as 3 day incubations. As shown in FIGS. 20A-20D, recovery of samples in Stepanol was not achieved to any significant degree.

Recovery of *N. Eutropha* D23 Cells After Incubation of 1× with Plantapon 611 L UP (0.1-1%) for Different Time Periods

Figure 21A:
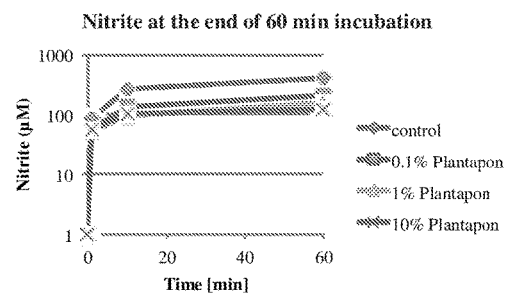
FIG. 21A shows the nitrite production of *N. eutropha* D23 with various concentrations of Plantapon 611 L UP. The nitrite concentration is plotted relative to time.
Figure 21B:
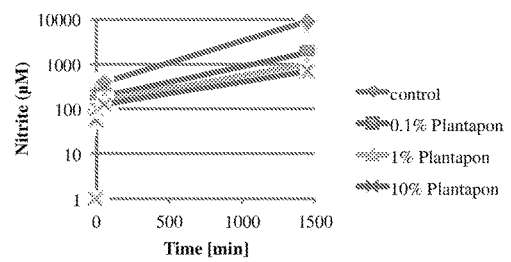
FIG. 21B shows the nitrite production of *N. eutropha* D23 with various concentrations of Plantapon 611 L UP. The nitrite concentration is plotted relative to time.
Figure 21C:
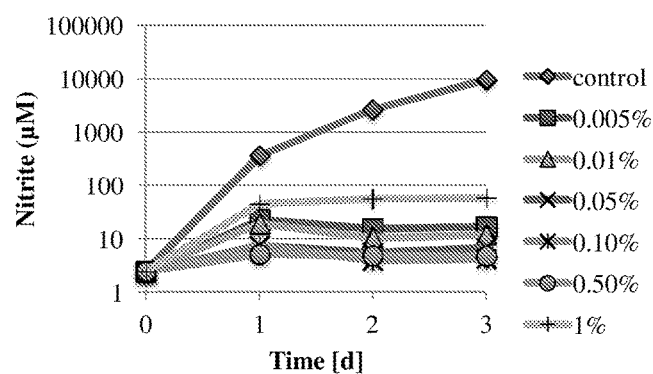
FIG. 21C shows the nitrite production of *N. eutropha* D23 with various concentrations of Plantapon 611 L UP. The nitrite concentration is plotted relative to time.
Figure 21D:
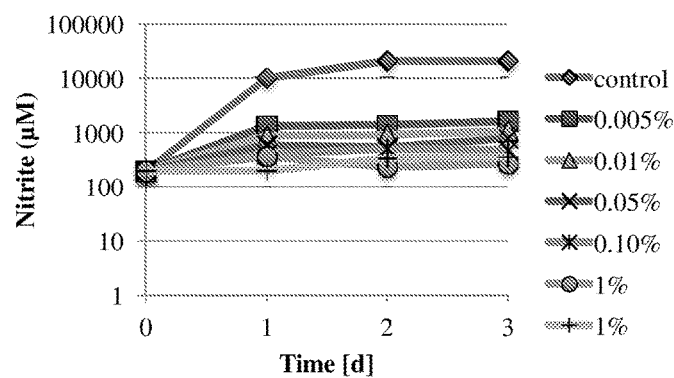
FIG. 21D shows the nitrite production of *N. eutropha* D23 with various concentrations of Plantapon 611 L UP. The nitrite concentration is plotted relative to time.
Figure 22A:
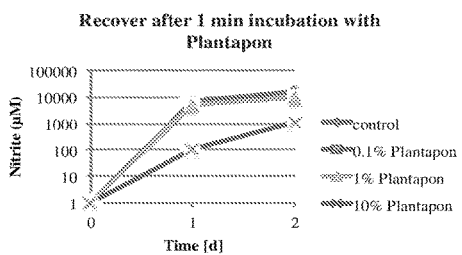
FIG. 22A shows the nitrite production of *N. eutropha* D23 after incubation with Plantapon 611 L UP. The nitrite concentration is plotted relative to time.
Figure 22B:
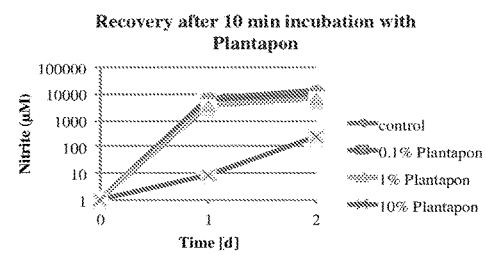
FIG. 22B shows the nitrite production of *N. eutropha* D23 after incubation with Plantapon 611 L UP. The nitrite concentration is plotted relative to time.
Figure 22C:
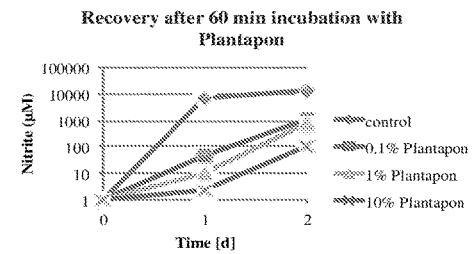
FIG. 22C shows the nitrite production of *N. eutropha* D23 after incubation with Plantapon 611 L UP. The nitrite concentration is plotted relative to time.
Figure 22D:
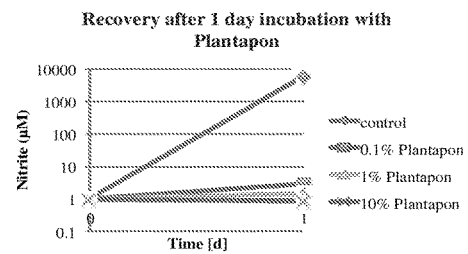
FIG. 22D shows the nitrite production of *N. eutropha* D23 after incubation with Plantapon 611 L UP. The nitrite concentration is plotted relative to time.

*N. eutropha* D23 cells were incubated with and recovered from Plantapon 611 L UP were done as indicated above. As shown in FIGS. 21A-21B, nitrite accumulation of samples with surfactant was slightly less than nitrite accumulation of the controls at 60 minute and 1 day incubations with 1× ammonia oxidizing bacteria cell solutions. FIGS. 21C and 21D show incubation of 0.001× and 0.1× ammonia oxidizing bacteria cell solutions at various concentrations of surfactant. As shown in FIGS. 22A-22D, recovery of samples occurred after 1 minute, 10 minutes, and 60 minutes of incubation, but indicated very little recovery after 1 day of incubation, as compared to the control sample.

Figure 23A:
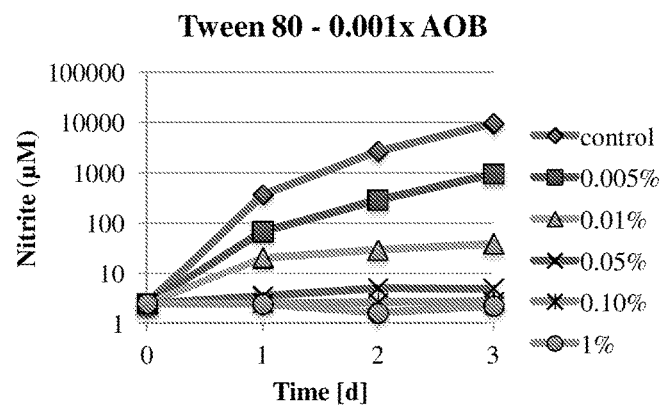
FIG. 23A shows the nitrite production of *N. eutropha* D23 with various concentrations of Tween 80. The nitrite concentration is plotted relative to time.
Figure 23B:
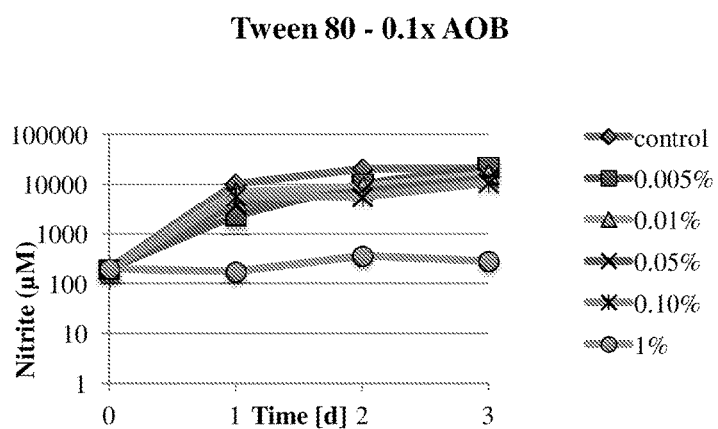
FIG. 23B shows the nitrite production of *N. eutropha* D23 with various concentrations of Tween 80. The nitrite concentration is plotted relative to time.
Figure 24A:
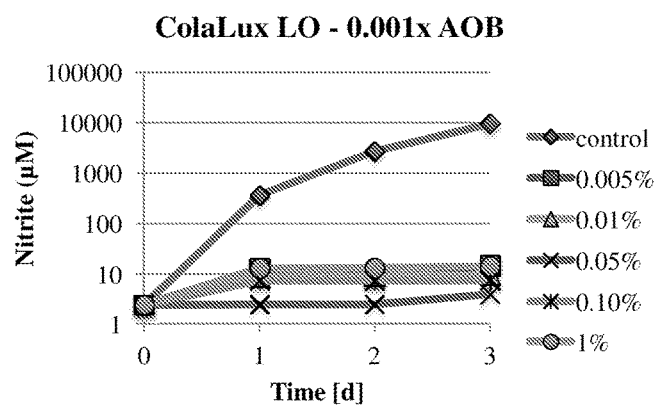
FIG. 24A shows the nitrite production of *N. eutropha* D23 with various concentrations of ColaLux LO. The nitrite concentration is plotted relative to time.
Figure 24B:
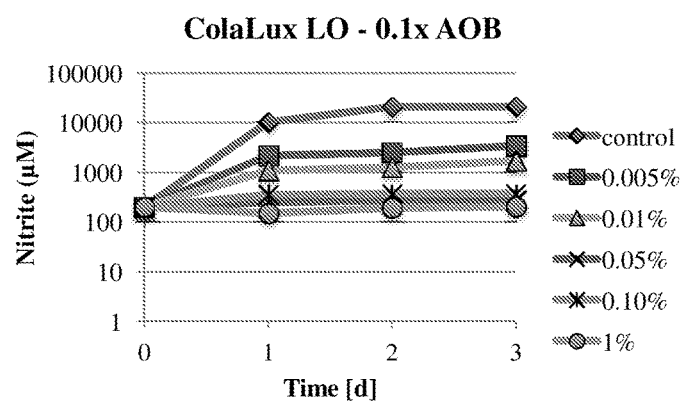
FIG. 24B shows the nitrite production of *N. eutropha* D23 with various concentrations of ColaLux LO. The nitrite concentration is plotted relative to time.
Figure 25A:
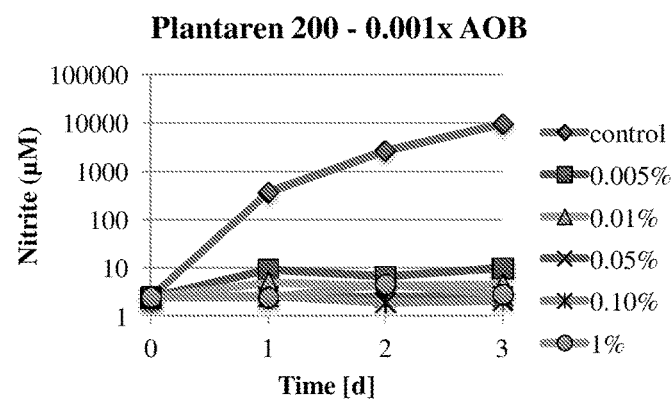
FIG. 25A shows the nitrite production of *N. eutropha* D23 with various concentrations of Plantaren 200. The nitrite concentration is plotted relative to time.
Figure 25B:
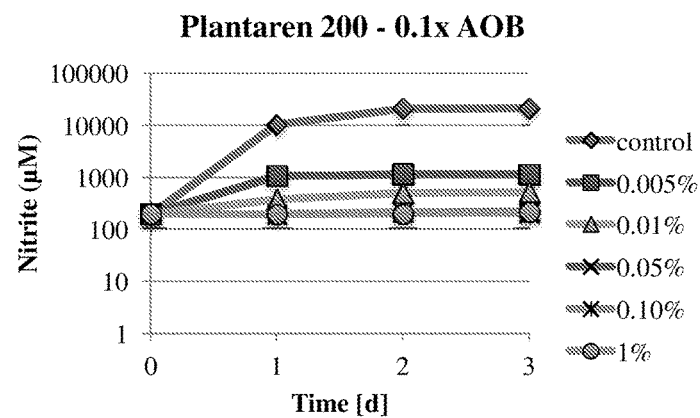
FIG. 25B shows the nitrite production of *N. eutropha* D23 with various concentrations of Plantaren 200. The nitrite concentration is plotted relative to time.
Figure 26A:
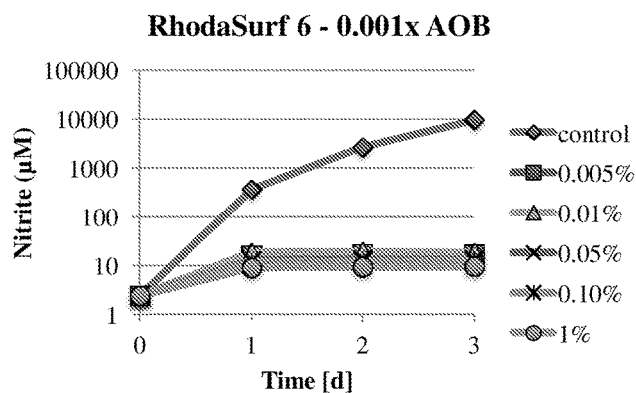
FIG. 26A shows the nitrite production of *N. eutropha* D23 with various concentrations of RhodaSurf 6. The nitrite concentration is plotted relative to time.
Figure 26B:
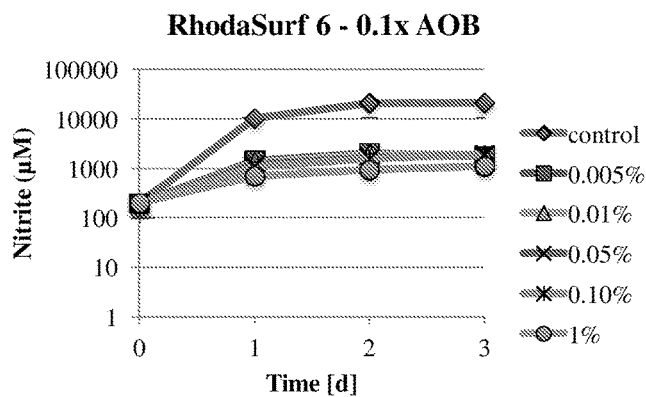
FIG. 26B shows the nitrite production of *N. eutropha* D23 with various concentrations of RhodaSurf 6. The nitrite concentration is plotted relative to time.

FIGS. 23A through 26B show further results of nitrite accumulation versus time for various surfactants including Tween 80 (FIGS. 23A-23B); ColaLux LO (FIGS. 24A-24B); Plantaren 200 (FIGS. 25A-25B); and RhodaSurf 6 (FIGS. 26A-26B), as discussed above.

Figure 27:
FIG. 27 is a summary table of surfactant recovery of *N. eutropha* D23.
Figure 27:
Figure 27:
Figure 27:

FIG. 27 is a summary chart of recovery of *N. eutropha* D23 with a 1× cell density, after 1 minute, 10 minute, 60 minutes, and 1 day incubations in various surfactants. Good recovery is indicative of nitrite production comparable to the control. Slow recovery is indicative of a reduced recovery as compared to the control. Very slow recovery is indicative of a greater reduced recovery as compared to the control. No recovery is indicative of none or substantially no nitrite production measured.

INCORPORATION BY REFERENCE

All publications and patents mentioned herein are hereby incorporated by reference in their entirety as if each individual publication or patent was specifically and individually indicated to be incorporated by reference.

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

Certain embodiments are within the following claims.

The invention claimed is:

1. A kit comprising:
   a preparation of live ammonia oxidizing bacteria in a media having a carbon dioxide concentration of less than about 400 ppm and a phosphate concentration of greater than about 1 micromolar;
   an activator for activating the ammonia oxidizing bacteria having at least one of ammonia, ammonium ions, and urea at a concentration of between about 10 micromolar to about 100 millimolar; and
   a delivery device for delivering at least one of the preparation of ammonia oxidizing bacteria and the activator to a subject.

2. The kit of claim 1, wherein the delivery device comprises a first chamber and a second chamber, wherein the first chamber and the second chamber are separated by a barrier provided to prevent fluid communication between the first chamber and the second chamber.

3. The kit of claim 1, further comprising a wash solution or wipe provided to clean the surface to which the preparation of ammonia oxidizing bacteria is applied.

4. The kit of claim 1, further comprising a diluting solution to allow dilution of at least one of the preparation of ammonia oxidizing bacteria and the activator.

5. The kit of claim 1, further comprising an assay to determine a viability of the preparation of ammonia oxidizing bacteria.

6. The kit of claim 1, further comprising an assay to determine a characteristic of the surface to which the preparation of ammonia oxidizing bacteria is applied.

7. The kit of claim 2, wherein the second chamber comprises a controlled release material, e.g., slow release material, and the activator comprising at least one of ammonia, ammonium ions, and urea, to provide a controlled release, e.g., slow release, of the at least one of ammonia, ammonium ions, and urea to the preparation of ammonia oxidizing bacteria upon delivery.

8. The kit of claim 1, wherein the delivery device comprises a multiple-use delivery device.

9. The kit of claim 2, wherein the first chamber, or the preparation of ammonia oxidizing bacteria, further comprising an excipient, e.g., one of a pharmaceutically acceptable excipient and a cosmetically acceptable excipient.

10. The kit of claim 1, wherein the preparation of ammonia oxidizing bacteria comprises about $10^{10}$ to about $10^{13}$ CFU/L.

11. The kit of claim 1, wherein the preparation of ammonia oxidizing bacteria comprises between about 0.1 milligrams (mg) and about 1000 mg of ammonia oxidizing bacteria.

12. The kit of claim 9, wherein the mass ratio of ammonia oxidizing bacteria to the excipient, e.g., the pharmaceutically acceptable excipient or the cosmetically acceptable excipient is in a range of about 0.1 grams per liter to about 1 gram per liter.

13. The kit of claim 1, further comprising at least one activation indicator component to indicate activation of the preparation of ammonia oxidizing bacteria and the activator.

14. The kit of claim 1, wherein the delivery device is configured to deliver the preparation of ammonia oxidizing bacteria and the activator substantially simultaneously.

15. The kit of claim 1, wherein the ammonia oxidizing bacteria is selected from the group consisting of *Nitrosomonas, Nitrosococcus, Nitrosospira, Nitrosocystis, Nitrosolobus, Nitrosovibrio*, and combinations thereof.

16. The kit of claim 1, further comprising instructions for delivering at least one of the preparation of ammonia oxidizing bacteria and the activator to the subject.

17. The kit of claim 1, wherein the media has a carbon dioxide concentration of less than about 200 ppm.

18. The kit of claim 1, wherein the media has a phosphate concentration of greater than about 10 micromolar.

* * * * *